US011219236B2

(12) United States Patent
Astrup et al.

(10) Patent No.: US 11,219,236 B2
(45) Date of Patent: Jan. 11, 2022

(54) METHODS OF INDUCING WEIGHT LOSS

(71) Applicants: GELESIS LLC, Boston, MA (US);
UNIVERSITY OF COPENHAGEN,
Copenhagen (DK)

(72) Inventors: Arne Astrup, Klampenborg (DK);
Christian Ritz, Bronshoj (DK); **Mads
Fiil Hjorth, Rodovre (DK); Yishai
Zohar**, Brookline, MA (US)

(73) Assignees: Gelesis LLC, Boston, MA (US);
University of Copenhagen,
Copenhagen (DK)

( * ) Notice: Subject to any disclaimer, the term of this patent is extended or adjusted under 35 U.S.C. 154(b) by 0 days.

(21) Appl. No.: 16/214,694

(22) Filed: Dec. 10, 2018

(65) Prior Publication Data

US 2019/0254331 A1    Aug. 22, 2019

Related U.S. Application Data

(63) Continuation of application No. PCT/US2017/035537, filed on Jun. 1, 2017.

(60) Provisional application No. 62/357,441, filed on Jul. 1, 2016, provisional application No. 62/403,946, filed on Oct. 4, 2016.

(30) Foreign Application Priority Data

Jun. 10, 2016  (DK) .............................. PA201670419

(51) Int. Cl.
A23L 33/00       (2016.01)
A23L 33/21       (2016.01)
(52) U.S. Cl.
CPC ............... *A23L 33/30* (2016.08); *A23L 33/21* (2016.08); *A23V 2002/00* (2013.01)
(58) Field of Classification Search
CPC ..................................................... A23L 33/30
See application file for complete search history.

(56) References Cited

U.S. PATENT DOCUMENTS

| | | |
|---|---|---|
| 2003/0007996 A1 | 1/2003 | Graham et al. |
| 2008/0193603 A1 | 8/2008 | Hayes et al. |
| 2008/0275728 A1 | 11/2008 | Ordovas et al. |
| 2012/0058094 A1 | 3/2012 | Blaser et al. |
| 2013/0079612 A1 | 3/2013 | Hunt et al. |
| 2014/0052722 A1 | 2/2014 | Bertsimas et al. |
| 2014/0128289 A1 | 5/2014 | Gordon et al. |
| 2015/0284779 A1 | 10/2015 | Le Chatelier et al. |
| 2015/0366898 A1 | 12/2015 | Ron et al. |
| 2019/0062811 A1 | 2/2019 | Hjorth et al. |

FOREIGN PATENT DOCUMENTS

| | | |
|---|---|---|
| WO | 02/11562 A2 | 2/2002 |
| WO | 2016/020119 A1 | 2/2016 |
| WO | 2016/078944 A1 | 5/2016 |

OTHER PUBLICATIONS

Fujioka et al., "Weight loss with sibutramine improves glycaemic control and other metabolic parameters in obese patient with type 2 diabetes mellitus", Diabetes, Obesity and Metabolism, vol. 2, No. 3, pp. 175-187 (2000).*
Racette et al., "Modest weight loss improves insulin action in obese African Americans", Metabolism, Clinical and Experimental, vol. 54, No. 7, pp. 960-965 (2005).*
Wikipedia, Hyperglycemia, May 27, 2016; p. 1/5, Retrieved on Aug. 2, 2017, from https://en.wikipedia.org/wiki/Hyperglycemia>.
Wikipedia, Nordic race, May 23, 2016; p. 1-18, Retrieved on Aug. 2, 2017, from <https://en.wikipedia.org/wiki/Nordic_race>.
Greenberg, R. "Glycemic Load and Glycemic Index: What's the Difference and Why Does it Matter?", HuffPost, Aug. 29, 2011; p. 3-6, highlight; Retrieved on Aug. 2, 2017, from <http://www.huffingtonpost.com/riva-greenberg/gl-and-gi_b_863126.html>.
Panagiotakos, et al. "The Relationship between Dietary Habits, Blood Glucose and Insulin Levels among People without Cardiovascular Disease and Type 2 Diabetes," Rev. Diabetic Stud., 2: 208-215 (2005).
Egshatyan, L., et al., "Gut microbiota and diet in patients with different glucose tolerance," Endocrine Connections, 5: 1-9 (2016).
Roager, H. M., et al., "Microbial Enterotypes, Inferred by the Prevotella-to-Bacteroides Ratio, Remained Stable during a 6-Month Randomized Controlled Diet Intervention with the New Nordic Diet," Applied and Environmental Microbiology, 80(3): 1142-1149 (2014).
Roager, H. M., et al., Supplemental Material for "Microbial Enterotypes, Inferred by the Prevotella to Bacteroides Ratio, Remain Stable during a 6-Month Randomized Controlled Diet Intervention with the New Nordic Diet," pp. 1-13 (2014).
Kovatcheva-Datchary, P., et al., "Dietary Fiber-Induced Improvement in Glucose Metabolism Is Associated with Increased Abundance of Prevotella," Cell Metabolism 22: 971-982 (2015).
Menni, C., et al., "Gut microbiome diversity and high-fibre intake are related to lower long-term weight gain," International Journal of Obesity, pp. 1-7 (2017).

(Continued)

*Primary Examiner* — Kevin E Weddington
(74) *Attorney, Agent, or Firm* — Elmore Patent Law Group, P.C.; Edgar Harlan; Carolyn Elmore

(57) ABSTRACT

The present disclosure relates to a method of inducing weight loss and/or preventing weight gain in a subject affected by administering certain diets selected based on the fasting blood glucose and/or the fasting insulin of the subject. The present disclosure further provides personalized dietary instruction, based on the fasting blood glucose and/or the fasting insulin of a subject, with the potential to improve the weight loss and prevent weight regain. The present disclosure further relates to methods for predicting weight loss success and classifying responsiveness of a subject to a certain diet as well as methods for selecting a weight loss or a weight gain diet for a subject based on the fasting blood glucose and/or the fasting insulin of the subject.

21 Claims, 20 Drawing Sheets

(56) References Cited

OTHER PUBLICATIONS

Kang, C. et al., "Healthy Subjects Differentially Respond to Dietary Capsaicin Correlating with Specific Gut Enterotypes," J Clin Endocrinol Metab, 101(12): 4681-4689 (2016).

F. de Moraes, A. C., et al., "Enterotype May Drive the Dietary-Associated Cardiometabolic Risk Factors," Frontiers in Cellular and Infection Microbiology, 7(47): 1-9 (2017).

Kjølboek, L., et al., "Protein supplements after weight loss do not improve weight maintenance compared with recommended dietary protein intake despite beneficial effects on appetite sensation and energy expenditure: a randomized, controlled, double-blinded trial," Am J Clin Nutr., pp. 1-14 (2017).

Arumugam, M., et al., "Enterotypes of the human gut microbiome," Nature, 473: 174-180 (2011).

Gorvitovskaia, A., et al., "Interpreting Prevotella and Bacteroides as biomarkers of diet and lifestyle," Microbiome, 4(15): 1-12 (2016).

Hong, P.-Y., et al., "Relative Abundance of *Bacteroides* spp. in Stools and Wastewaters as Determined by Hierarchical Oligonucleotide Primer Extension," Applied and Environmental Microbiology, 74(9): 2882-2893 (2008).

Due, A., et al., "Comparison of 3 ad libitum diets for weight-loss maintenance, risk of cardiovascular disease, and diabetes: a 6-mo randomized, controlled trial," Am J Clin Nutr., 88: 1232-1241 (2008).

"Understanding Pre-Diabetes", Diseases & Conditions Diabetes-Prevention, Jan. 1, 2013 (Jan. 1, 2013), p. 1, XP055397977, US Retrieved from the Internet: URL:https://web.archive.org/web/20141109232149/http://my.clevelandclinic.org/health/diseases_conditions/hicDiabetes_Basics/hicUnderstandingPre-Diabetes[retrieved on Aug. 10, 2017].

Wu, G. D. et al., "Linking long-term dietary patterns with gut microbial enterotypes", Science, vol. 334, No. 605, Oct. 7, 2011, 105-108.

Poulsen, S. et al., "Health effect of the New Nordic Diet in adults with increased waist circumference: a 6-mo randomized controlled trial", Amer. J. of Clinical Nutrition, vol. 99, No. 1, published online Nov. 20, 2013, Jan. 2014, 35-45.

* cited by examiner

METHODS OF INDUCING WEIGHT LOSS

RELATED APPLICATIONS

This application is a continuation of International Application No. PCT/US17/35537, which designated the United States and was filed on Jun. 1, 2017, published in English, which claims the benefit of U.S. Provisional Application No. 62/357,441, filed on Jul. 1, 2016 and U.S. Provisional Application No. 62/403,946, filed on Oct. 4, 2016.

This application claims priority under 35 U.S.C. § 119 or 365 to Denmark, Application No. PA 201670419, filed Jun. 10, 2016. The entire teachings of the above applications are incorporated herein by reference.

FIELD OF INVENTION

The present disclosure relates to a method of inducing weight loss and/or preventing weight gain in a subject effected by administering certain diets selected based on the fasting blood glucose and/or the fasting insulin of the subject. The present disclosure further provides personalized dietary instruction, based on the fasting blood glucose and/or the fasting insulin of a subject, with the potential to improve the weight loss and prevent weight regain. The present disclosure further relates to methods for predicting weight loss success and classifying responsiveness of a subject to a certain diet as well as methods for selecting a weight loss or a weight gain diet for a subject based on the fasting blood glucose and/or the fasting insulin of the subject.

BACKGROUND OF INVENTION

The causes of the wide variation in weight loss achieved by obese patients during a prescribed energy reduction are poorly understood. Differences in metabolic efficiency and adaptive reductions in energy expenditure cannot account for much of the variability, and most of the variability is supposed to be due to lack of adherence to the prescribed dietary energy deficit. The lack of adherence may well be due to biological factors with adverse influence on hunger, satiety, cravings and rewarding effects. Several lines of evidence have shown that insulin resistance per se is a trait that reduces the weight loss outcome on an energy restricted diet, but also in response to various weight loss compounds. For any given treatment obese patients with prediabetes and type 2 diabetes lose less weight than matched non-diabetics. Recently, a number of studies have shown that the 30-min insulin response to an oral glucose tolerance test (OGTT) is predictive of subsequent weight loss success, particularly if the diet has a low carbohydrate content (i.e. glycemic load=GL) and/or low glycemic index (GI) value (Ebbeling et al. 2007). The key finding is that those obese subjects with a high 30-min insulin response are successful on a diet with a low glycemic load, which means a diet with low carbohydrate content and/or a low glycemic index (GI) diet, or the combination of a reduced carbohydrate content and a low GI of the carbohydrate-rich foods in the diet (low GL diet). However, the studies demonstrating the interaction between 30-min insulin response and carbohydrate content/GI of the diet are generally small, and confirmation in larger trials is needed. Moreover, to measure insulin 30 min after a standardized OGGT is not easy, fast, cheap or easily available, so there is also a need for more simple predictors.

While the insulin concentrations in blood following an oral glucose tolerance test is a scientific interesting method to characterize individuals into insulin sensitive and insulin resistant phenotypes it is far too demanding and costly to have any major clinical relevance.

SUMMARY OF INVENTION

The present inventors have found that a simple fasting blood glucose (FPG) and/or fasting insulin (f-insulin) measurement can predict the dietary weight loss success of a subject to a higher degree than any insulin measurement after an OGTT. They also found that the correlation between FPG and 8 week weight loss on a low-energy diet providing 800-1,000 kcal/day is highly significant, and it also predicts loss of fat mass. They further found that combining measurements of FPG with measurements of f-insulin and/or 30-minutes insulin response may improve the predictive power of the method. It was surprisingly found that non-diabetic overweight or obese people with high FPG lose more weight than non-diabetic overweight or obese people with a low FPG during a low GI/low GL diet, such as on a high fiber diet rich in whole grain. Even more importantly, overweight or obese people with high FPG lose less weight and regain more weight than non-diabetic overweight or obese people with a low FPG during a high GI/high GL diet.

These findings represent a major break-through in individualized diet management, and will have major implications for the prevention and management of weight gain, overweight and obesity.

The present disclosure relates to a method for predicting dietary weight loss success of a subject comprising:
  determining the fasting blood glucose (FPG) and/or the fasting insulin (f-insulin) of said subject,
  classifying the subject with respect to the level of FPG and/or f-insulin, and
  predicting the dietary weight loss success of said subject in view of a predetermined diet.

The present disclosure further relates to a method for classifying responsiveness of a subject to a predetermined diet comprising determining the FPG and/or the f-insulin of said subject and classifying the subject with respect to the level of FPG and/or f-insulin.

The present disclosure further relates to a method for selecting a weight loss and/or a maintenance diet for a subject comprising:
  determining the FPG and/or the f-insulin of said subject; and
  selecting a diet based on the level of FPG and/or f-insulin of said subject.

The present disclosure further relates to a method for maintaining weight or preventing weight re-gain of a subject comprising determining the FPG and/or the f-insulin of said subject and providing to said subject a predetermined diet, thereby maintaining weight or preventing weight re-gain of said subject.

The present disclosure further relates to a method for selecting a weight gain diet for a subject comprising:
  determining the FPG and/or the f-insulin of said subject;
  optionally determining the BMI of said subject; and
  selecting a diet based on the level of FPG and/or f-insulin and optionally based on the BMI of said subject,
  thereby selecting a weight gain diet for said subject.

The present disclosure further relates to method of inducing weight loss in a subject in need thereof, the method comprising administering a predetermined diet to said subject, wherein the diet is chosen based on the FPG and/or f-insulin of said subject, thereby inducing weight loss in said subject.

The present disclosure further relates to method of treating overweight or obesity in a subject in need thereof, the method comprising administering a predetermined diet to said subject, wherein the diet is chosen based on the FPG and/or f-insulin of said subject, thereby treating overweight or obesity in said subject.

The present disclosure relates to a method for predicting dietary weight loss success of a subject comprising determining the FPG of said subject and classifying the subject as high FPG or low FPG:
  wherein a subject having a high FPG is prone to lose more weight on a low GL/low GI diet than a subject having a normal FPG;
  wherein a subject having a high FPG is prone to lose more weight on a low GL/low GI diet than on a high GL/high GI diet, thereby predicting the dietary weight loss success of said subject.

The present disclosure further relates to a method for classifying responsiveness of a subject to a low GL/low GI diet comprising determining the FPG of said subject and classifying the subject as high FPG or low FPG:
  wherein a subject having a high FPG is prone to gain weight on an ad libitum diet with high GL/high GI;
  wherein a subject having a high FPG is prone to maintain or lose weight on an ad libitum diet with low GL/low GI;
  thereby classifying responsiveness of said subject to said low GL/low GI diet.

The present disclosure further relates to a method for selecting a weight loss diet for a subject comprising:
  determining the FPG of said subject, and
  selecting ad libitum diet with low GL/low GI when said subject has a high FPG.

Preferably, in all the above-described methods of the invention, an ad libitum diet may be replaced with a calorie restricted diet for further improvement in weight loss.

The present disclosure further relates to a method for maintaining weight or preventing weight re-gain of a subject comprising determining the fasting blood glucose of said subject and administering to said subject a low GL/low GI ad libitum diet if the FPG of said subject is high.

The present disclosure further relates to a method for selecting a weight gain diet for a subject comprising:
  determining the FPG of said subject;
  determining the BMI of said subject; and
  selecting ad libitum diet with high GL/high GI when said subject has a high FPG.

DESCRIPTION OF DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

Figure 8:
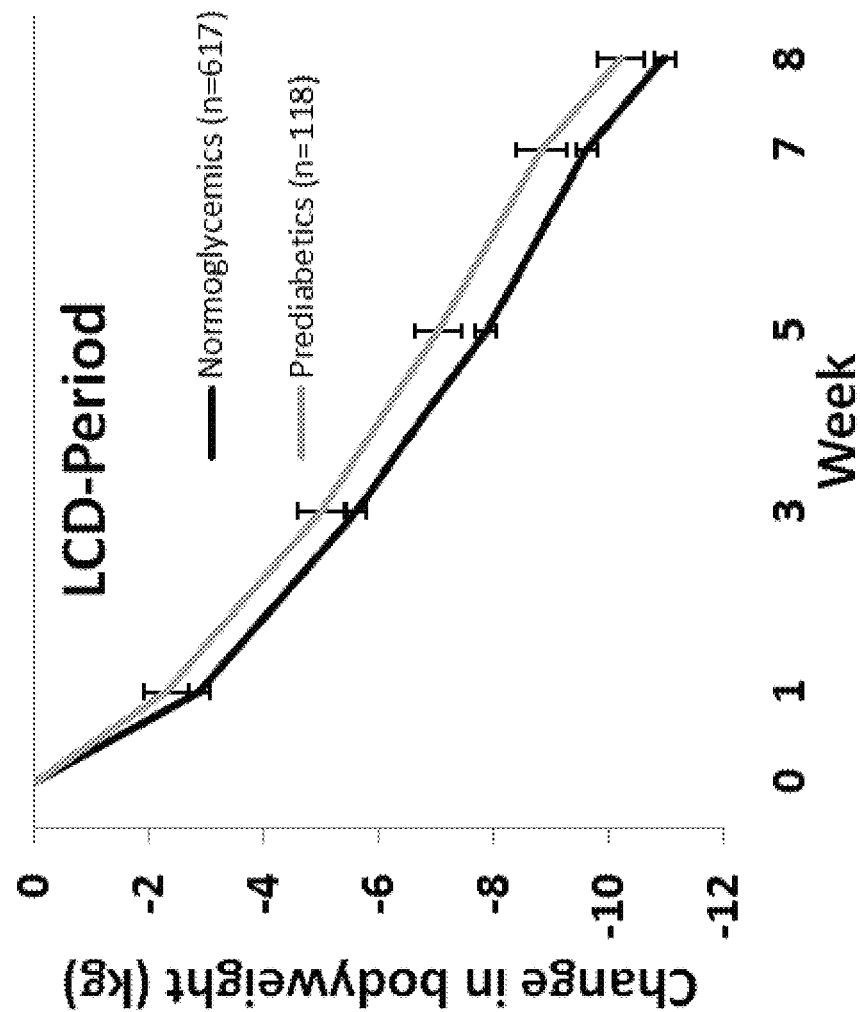

FIG. 8 is a line graph showing the change in bodyweight during 8 weeks of low calorie diet (LCD) in prediabetic and normoglycemic obese subjects. Data are presented as unstandardized regression coefficients (β) and 95% confidence intervals (CI) using a linear mixed model adjusted for age, gender, baseline BMI as fixed effects and subject, family and study centre as random effect.

Figure 9:
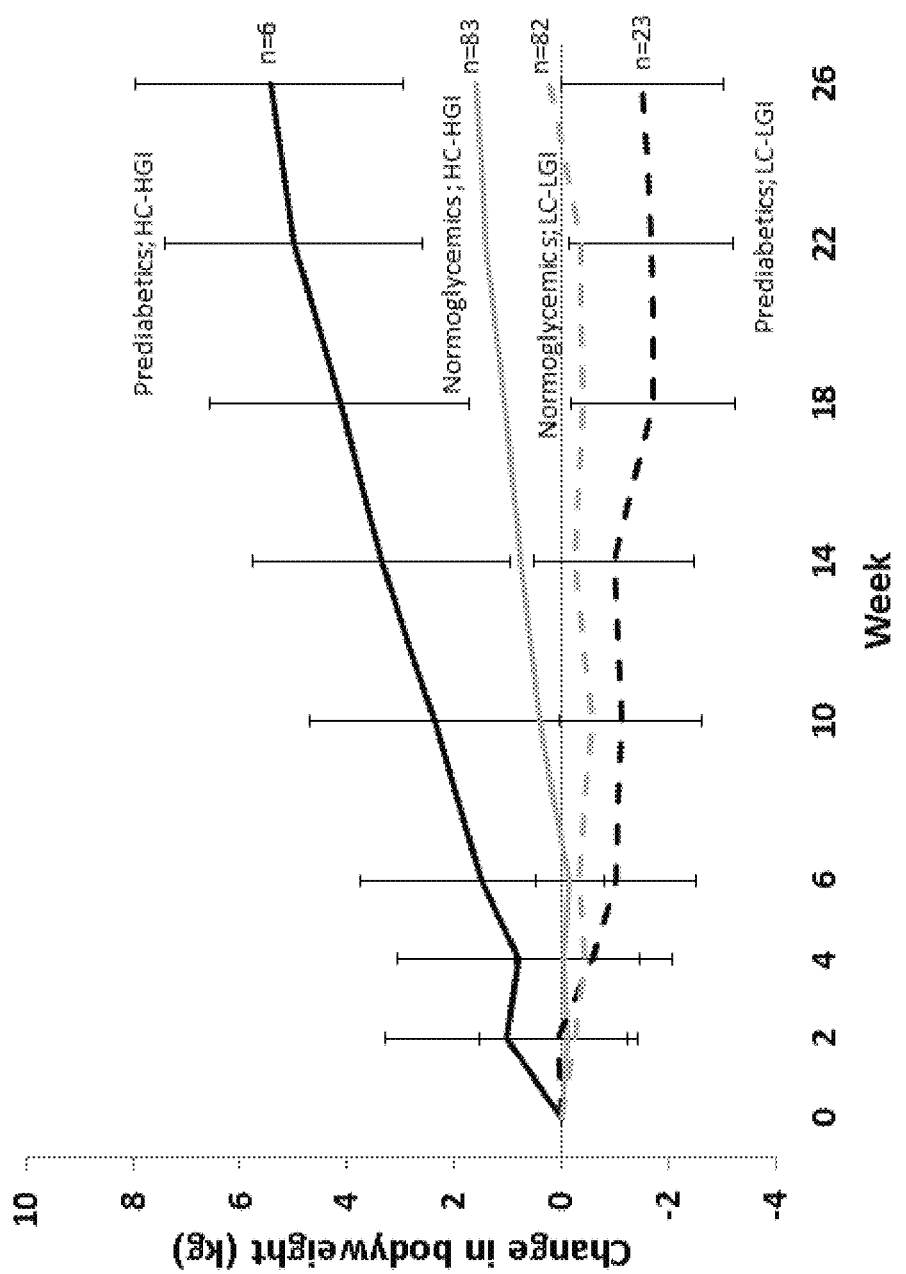

FIG. 9 is a line graph showing the change in bodyweight among individuals with prediabetes and normal fasting blood glucose (normoglycemic) 6 month ad libitum diet phase. HC-HGI, high carbohydrate-high glycemic index; LC-LGI, low carbohydrate-low glycemic index. Data are presented as unstandardized regression coefficients (β) and 95% confidence intervals (CI) using a linear mixed model adjusted for age, gender, baseline BMI and LCD-weight loss as fixed effects and subject, family and study center as random effect. Number of observations (n) on the figure is at week 26.

Figure 10:
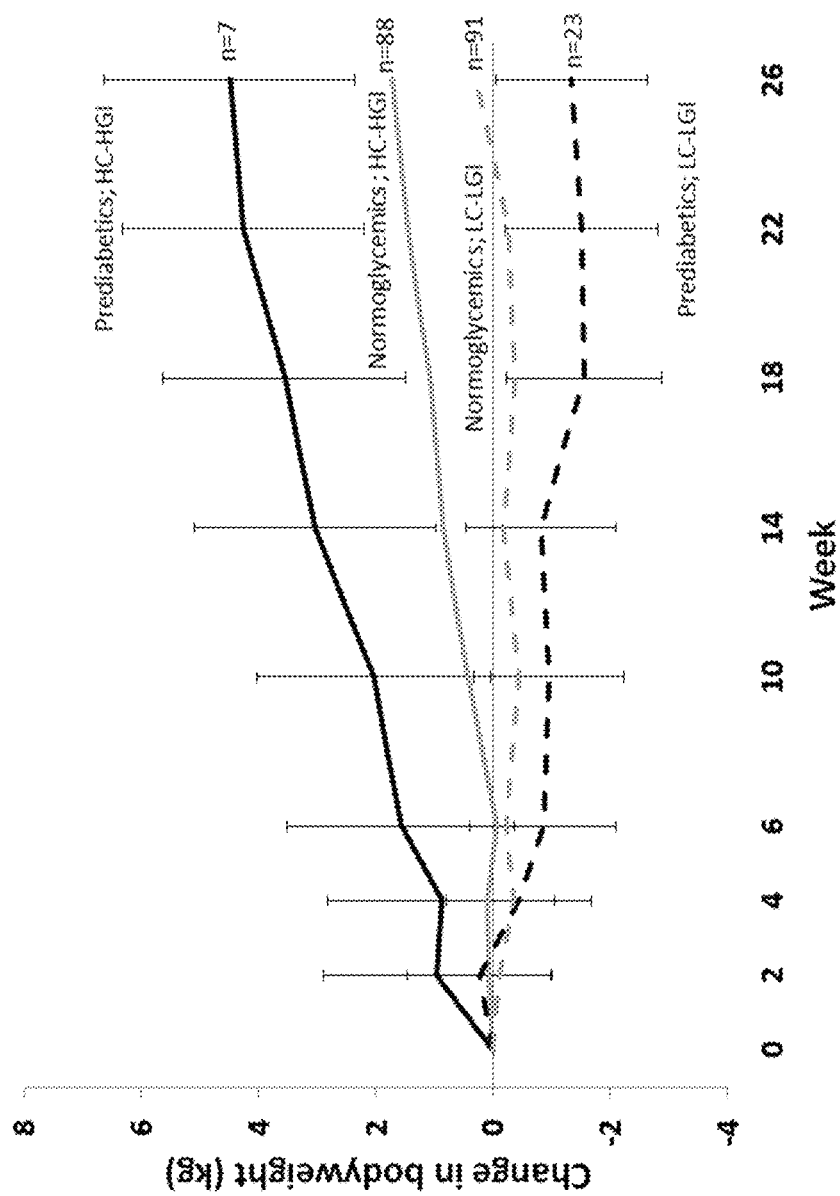

FIG. 10 is a line graph showing the change in bodyweight among individuals with prediabetes and normal fasting blood glucose measured before the LCD-period on high and low glycemic load. HC-HGI, high carbohydrate-high glycemic index; LC-LGI, low carbohydrate-low glycemic index. Data are presented as unstandardized regression coefficients (β) and 95% confidence intervals (CI) using a linear mixed model adjusted for age, gender, baseline BMI and LCD-weight loss as fixed effects and subject, family and study center as random effect. Number of observations (n) on the figure is at week 26.

Figure 11:
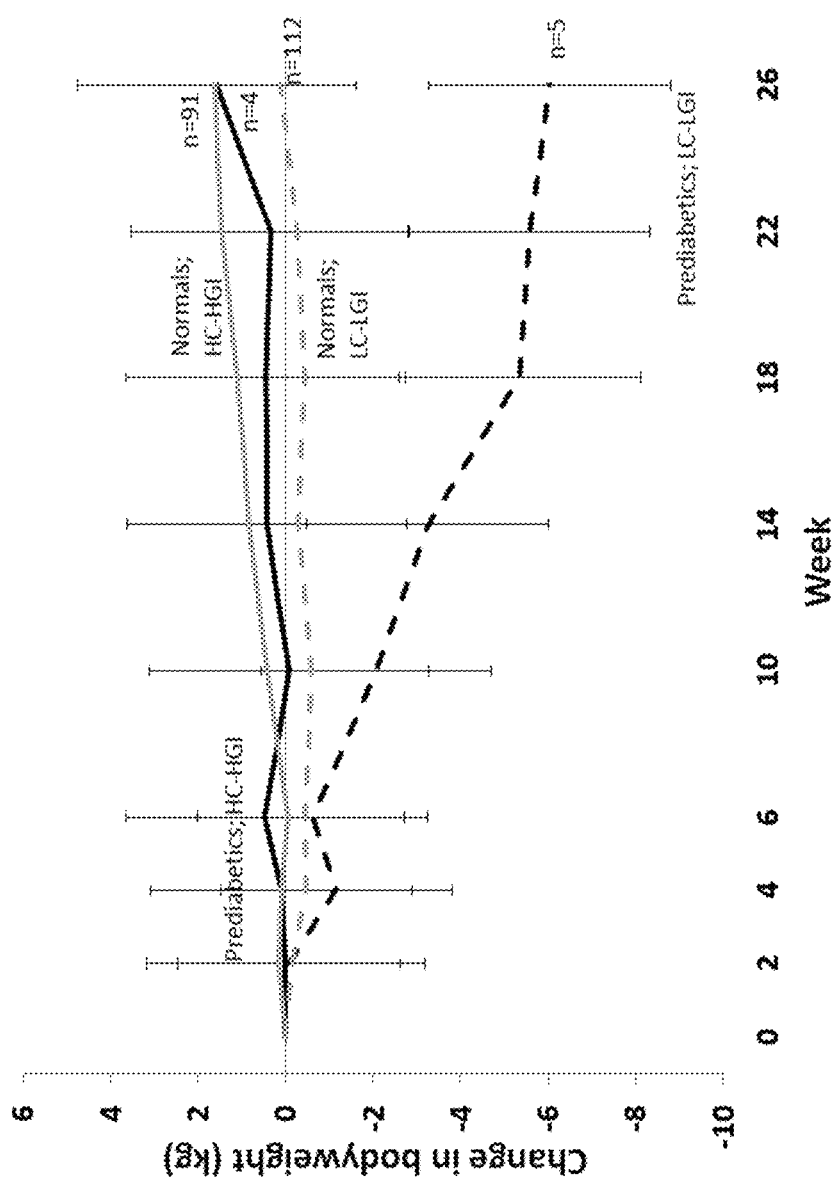

FIG. 11 is a line graph showing change in bodyweight among individuals with prediabetes and normal fasting blood glucose measured before randomization on high and low glycemic load. HC-HGI, high carbohydrate-high glycemic index; LC-LGI, low carbohydrate-low glycemic index. Data are presented as unstandardized regression coefficients (β) and 95% confidence intervals (CI) using a linear mixed model adjusted for age, gender, baseline BMI and LCD-weight loss as fixed effects and subject, family and study center as random effect. Number of observations (n) on the figure is at week 26.

Figure 12:
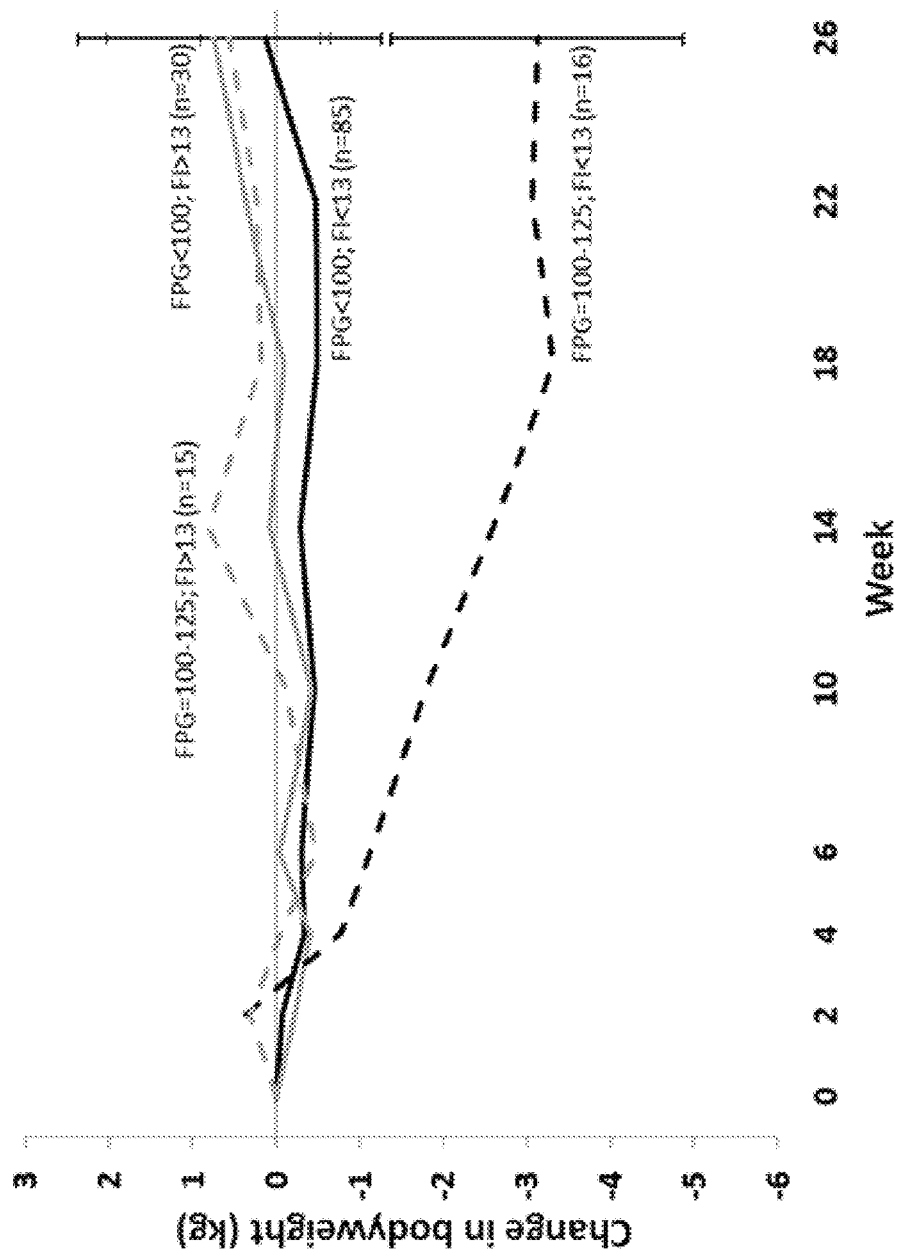

FIG. 12 is a line graph showing change in bodyweight among individuals with different combinations of Fasting plasma glucose and Fasting Insulin measured before the LCD-period on a low glycemic load diet. Data are presented as unstandardized regression coefficients (β) and 95% confidence intervals (CI) using a linear mixed model adjusted for age, gender, baseline BMI and LCD-weight loss as fixed effects and subject, family and study center as random effect. Number of observations (n) on the figure is at week 26.

Figure 13:
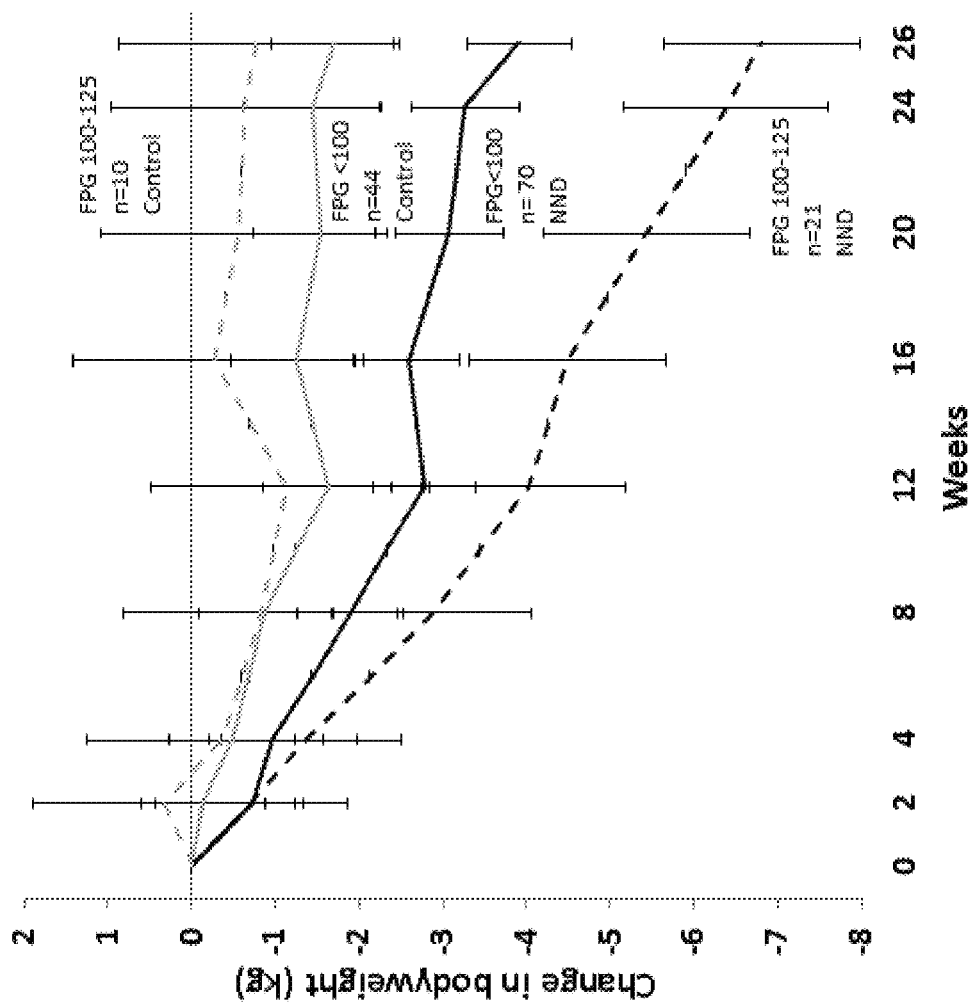

FIG. 13 is a line graph showing bodyweight change in the control (ADD) and New Nordic Diet (NND) arm of the SHOPUS trial stratified on Fasting Plasma Glucose. Abbreviation: FPG, Fasting plasma glucose; NND, New Nordic Diet. Data are presented as estimated means and 95% confidence intervals using a linear mixed model adjusted for age, gender, baseline BMI as fixed effects and subject as random effect.

Figure 14:
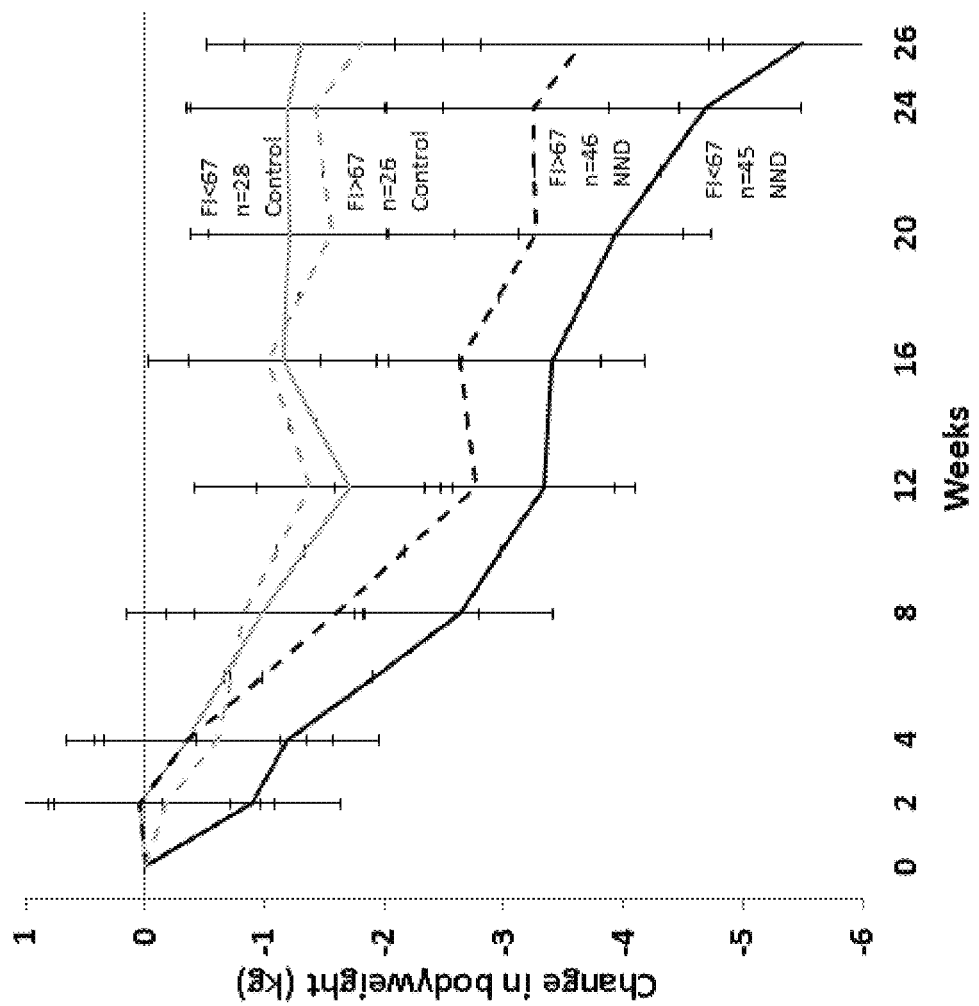

FIG. 14 is a line graph showing bodyweight change in the control (ADD) and New Nordic Diet (NND) arm of the SHOPUS trial stratified on Fasting Insulin. Abbreviation: FI, Fasting Insulin; NND, New Nordic Diet. Data are presented as estimated means and 95% confidence intervals using a linear mixed model adjusted for age, gender, baseline BMI as fixed effects and subject as random effect.

Figure 15:
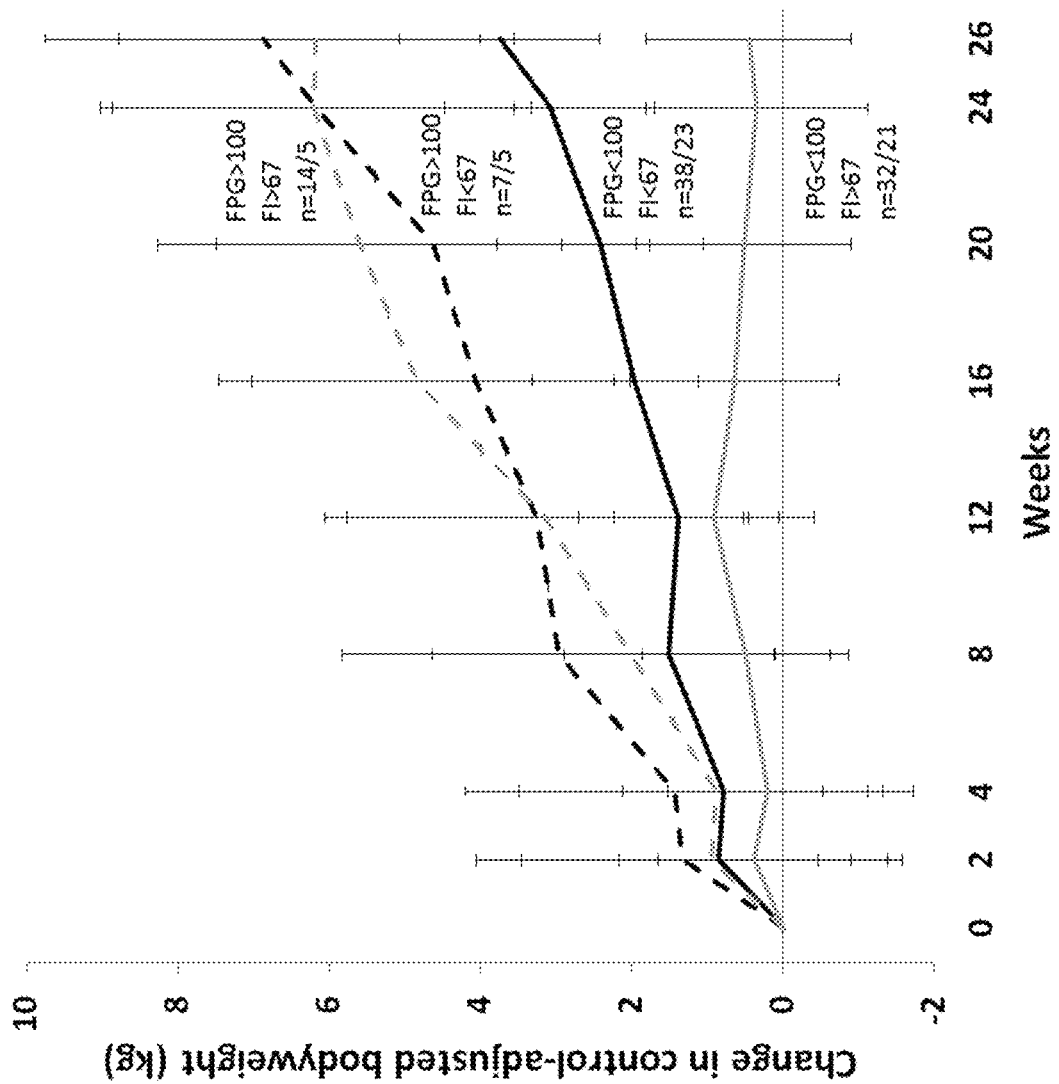

FIG. 15 is a line graph showing differences in bodyweight change between NND and Control (ADD) diets in four distinct groups of individuals based on FPG and FI. Abbreviations: FI, Fasting insulin; FPG, Fasting plasma glucose; NND, New Nordic Diet. Data are presented as estimated means and 95% confidence intervals using a linear mixed model adjusted for age, gender, baseline BMI as fixed effects and subject as random effect. The Zero line indicates no difference between diets. Above the zero line favors the NND diet and below the zero line favors the Control diet.

Figure 16:
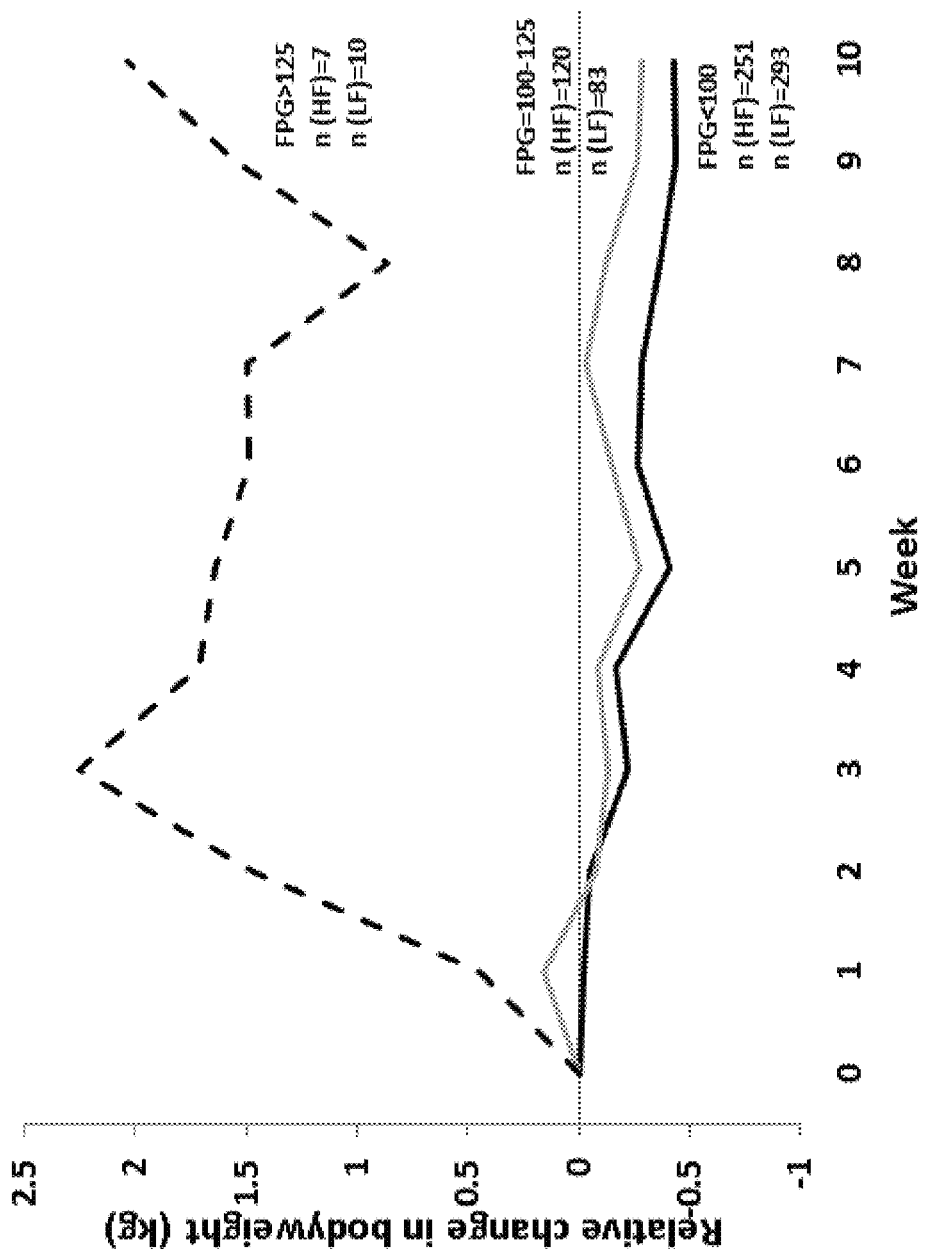

FIG. 16 is a line graph showing differences in bodyweight change between low fat and high fat diets in three distinct groups of individuals based on FPG. Abbreviations: FPG, Fasting plasma glucose; HF, High fat; LF, Low fat. Data are presented as estimated means using a linear mixed model adjusted for age, gender, baseline BMI as fixed effects and subject and study center as random effect. The Zero line indicates no difference between diets. Above the zero line favors the high fat diet and below the zero line favors the low fat diet. Individuals having FPG<100 have larger weight loss on a low fat diet compared to a high fat diet (−0.43 kg, P=0.034).

Figure 17:
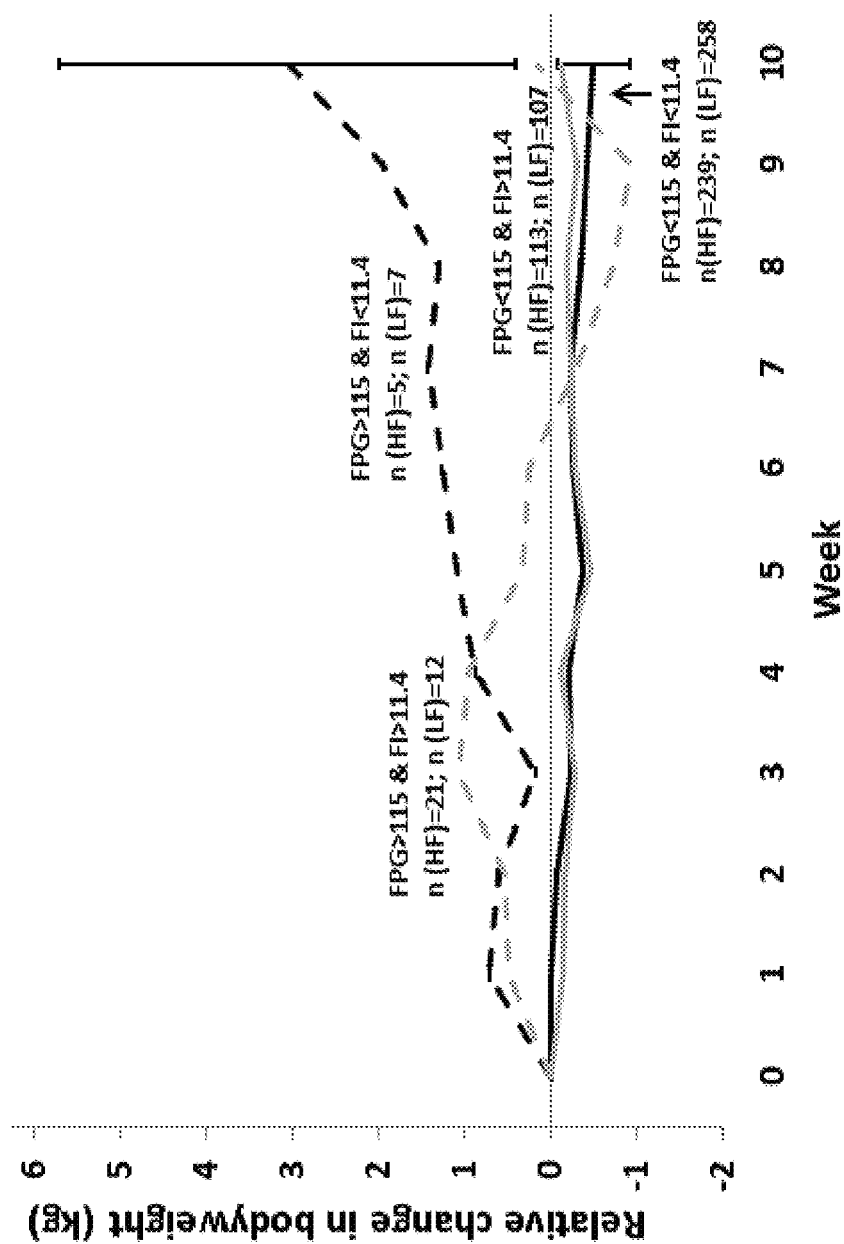

FIG. 17 is a line graph showing: Differences in bodyweight change between low fat and high fat diets in four distinct groups of individuals based on FPG and FI. Abbreviations: FI, Fasting insulin; FPG, Fasting plasma glucose; HF, High fat; LF, Low fat. Data are presented as estimated means and 95% confidence intervals using a linear mixed model adjusted for age, gender, baseline BMI as fixed effects and subject and study center as random effect. The Zero line indicates no difference between diets. Above the zero line favors the high fat diet and below the zero line favors the low fat diet.

Figure 18:
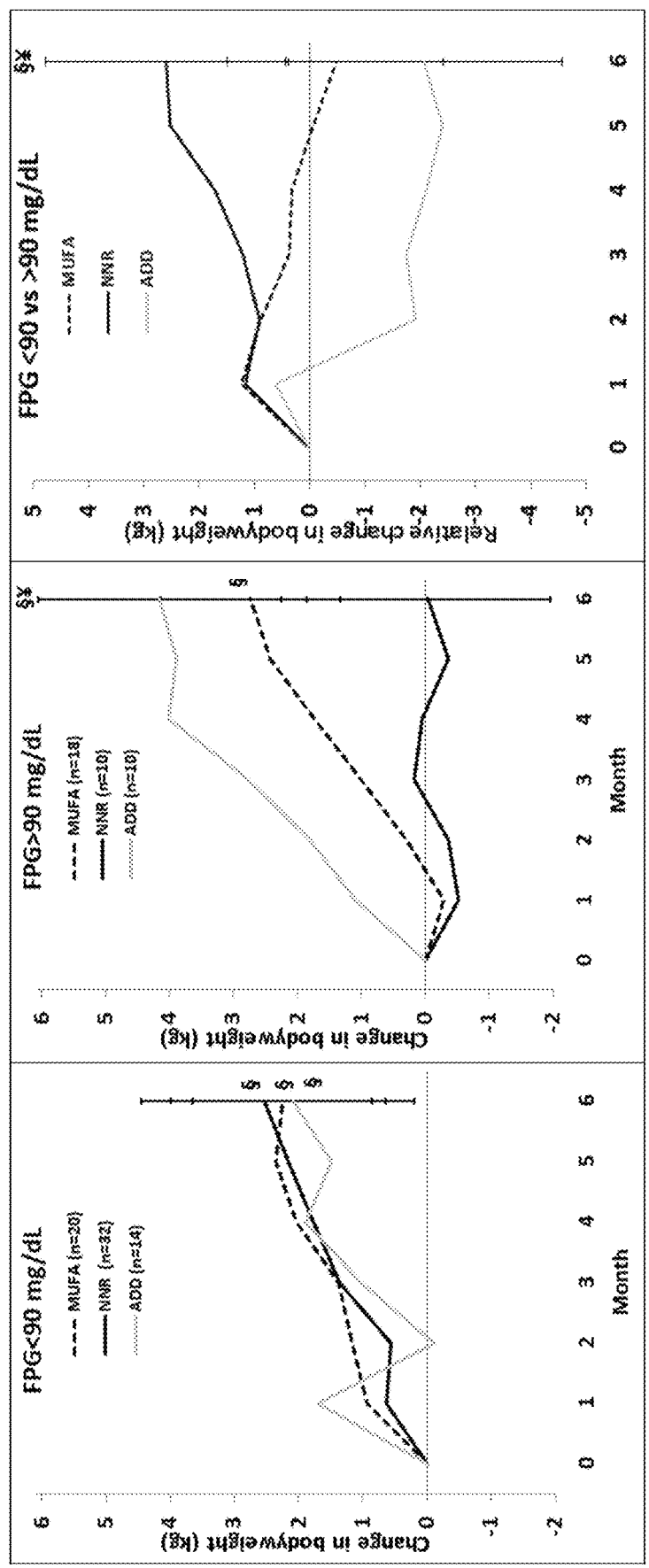

FIG. 18 shows change in body weight among participants <90 mg/dL, >90 mg/dL and the relative difference between these two phenotypes on MUFA, NNR and ADD. Abbreviations: FPG, Fasting plasma glucose. Data are presented as estimated mean weight change from baseline and 95% confidence intervals for each combination of the diet-time-FPG strata interaction in the linear mixed models, which were additionally adjusted for age, gender, BMI, and LCD weight loss, and subjects. ¥ indicate significant difference between the diets (P<0.05); § indicate significant difference from zero (P<0.05).

Figure 19:
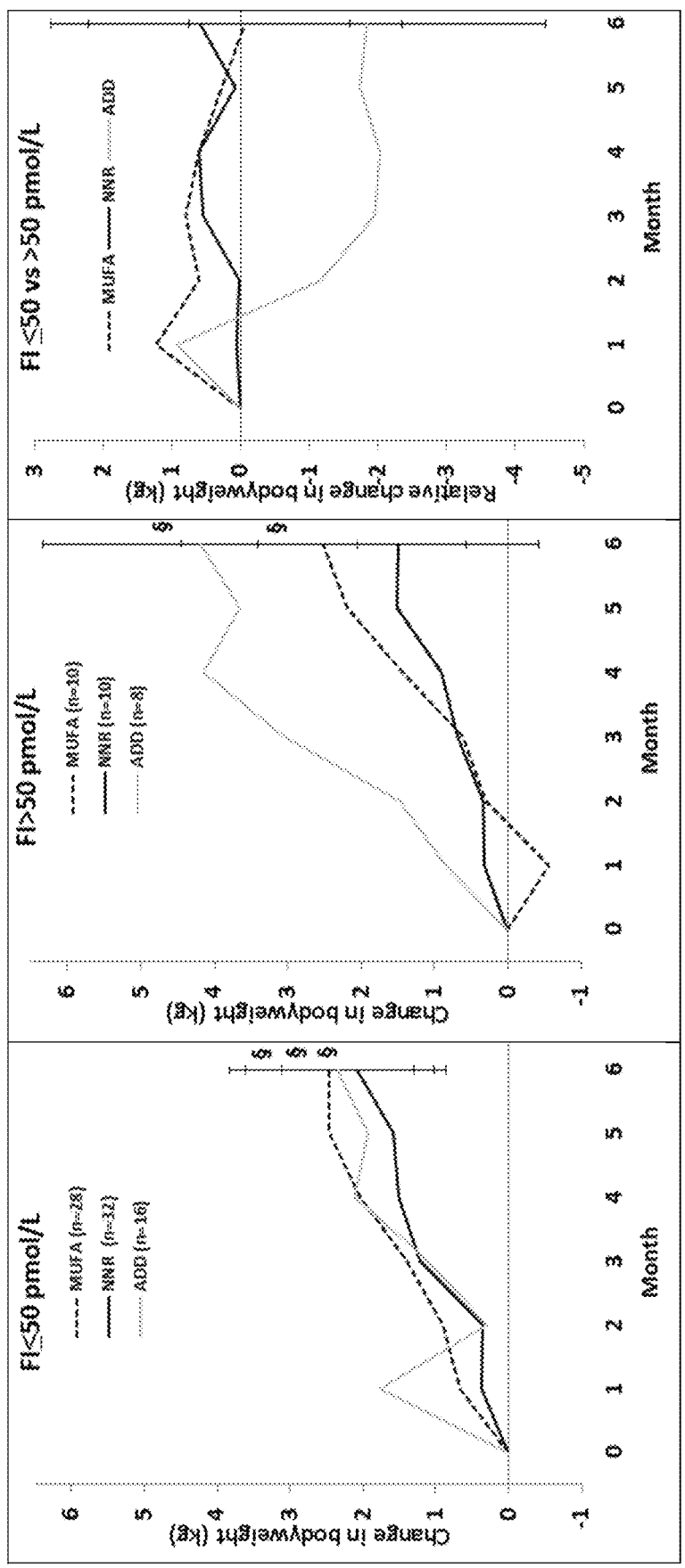

FIG. 19 shows changes in body weight among participants ≤50 pmol/L, >50 pmol/L and the relative difference between these two phenotypes on MUFA, NNR and ADD. Abbreviations: FI, Fasting insulin. Data are presented as estimated mean weight change from baseline and 95% confidence intervals for each combination of the diet-time-FPG strata interaction in the linear mixed models, which were additionally adjusted for age, gender, BMI, and LCD weight loss, and subjects. ¥ indicate significant difference between the diets (P<0.05); § indicate significant difference from zero (P<0.05).

Figure 20:
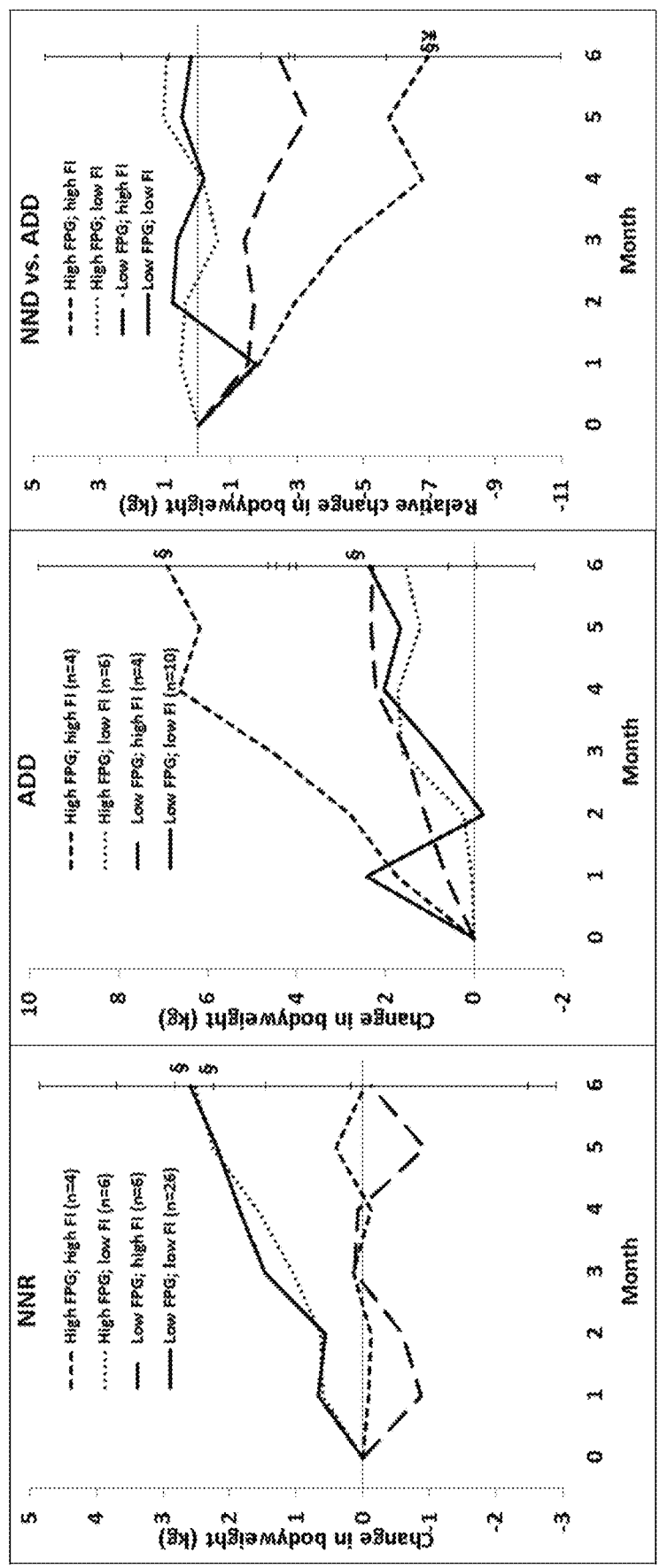

FIG. 20 shows change in body weight among participants with the four phenotypes of FPG and FI on NNR, ADD and the relative difference between NND and ADD. Abbreviations: FI, Fasting insulin; FPG, Fasting plasma glucose. Data are presented as estimated mean weight change from baseline and 95% confidence intervals for each combination of the diet-time-FPG strata interaction in the linear mixed models (except for the MUFA-diet as n=1 in one of the four phenotypes), which were additionally adjusted for age, gender, BMI, and LCD weight loss, and subjects. ¥ indicate significant difference between the diets (P<0.05); § indicate significant difference from zero (P<0.05).

DEFINITIONS

The term "weight loss" as used herein refers to a reduction of the total body mass, due to a mean loss of fluid, body fat or adipose tissue and/or lean mass, namely bone mineral deposits, muscle, tendon, and other connective tissue. In the context of the present disclosure, weight loss is at least partly due to a "loss of fat mass" also called "reduction of body fat".

The term "determining" as it is used with regard to determining a patient's glucose levels including fasting plasma glucose and/or fasting insulin of a subject includes testing a sample from the patient and measuring the glucose levels using standard techniques known in the art including but not limited to drawing blood samples from a fasting patient, using finger prick tests. Other non-invasive tests may also be used to determine glucose levels of a patient. The term "determining" also covers those instances where the subject's fasting plasma glucose and fasting insulin are already known and additional testing of a sample from the subject is not required.

The terms "f-BG" or "fasting blood glucose" or "fasting blood sugar" or "fasting plasma glucose" or "FPG" are all equivalent and as used herein they refer to the amount of glucose (sugar) present in the blood of a human or animal. The fasting blood glucose level is measured after a fast of approximately 8 hours.

The term "low GL/low GI diet" or "low CHO/low GI diet" as used herein refers to a low-glycemic diet, which is a diet based on food selected because of their minimal alteration of circulating glucose levels. Such diets in principle also include various specific diets characterized by a reduction of total carbohydrate load, for example low-carb diets and Atkin's diets. The reduction of carbohydrates load may be achieved by increasing the fat content, for example in the low-carbohydrate high fat (LCHF) diet, or by increasing the protein content, for example high-protein diets and Paleolithic diets, or by increasing both the fat content and the protein content. In addition, all low-GI diets are examples of low GL/low GI diet. Similarly, the term "high GL/high GI diet" or "high CHO/high GI diet" as used herein refers to high-glycemic diet, which is a diet comprising food that causes a substantial increase of circulating glucose levels.

Glycemic index (GI) and glycemic load (GL) are measures of the effect on blood glucose level after a food containing carbohydrates is consumed. Glucose has a glycemic index of 100 units, and all foods are indexed against that number. Low GI foods affect blood glucose and insulin levels less and have a slower rate of digestion and absorption. A food's GI value can be determined experimentally. For example, a measured portion of the food containing 50 grams of available carbohydrate (or 25 grams of available carbohydrate for foods that contain lower amounts of carbohydrate) is fed to 10 healthy people after an overnight fast. Finger-prick blood samples are taken at 15-30 minute intervals over the next two hours. These blood samples are used to construct a blood sugar response curve for the two hour period. The incremental area under the curve (iAUC) is calculated to reflect the total rise in blood glucose levels after eating the test food. The GI value is calculated by dividing the iAUC for the test food by the iAUC for the reference food (same amount of glucose) and multiplying by 100 (see FIG. 1). The use of a standard food is essential for reducing the confounding influence of differences in the physical characteristics of the subjects. The average of the GI ratings from all ten subjects is published as the GI for that food.

The glycemic load (GL) of food is a number that estimates how much the food will raise a person's blood glucose level after eating it. One unit of glycemic load approximates the effect of consuming one gram of glucose. Glycemic load accounts for how much carbohydrate is in the food and how much each gram of carbohydrate in the food raises blood glucose levels. Glycemic load is based on the glycemic index (GI), and is calculated by multiplying the grams of available carbohydrate in the food times the food's GI and then dividing by 100. Throughout the present application, the glycemic load is indicated as grams/day.

A reduction in GL of the diet can be achieved by various means, for example by increasing the dietary fiber content in food and meals, and/or by increasing the fat content in food or meals and/or by increasing protein content in food or meals.

In some embodiments the GL of a diet is reduced by selecting foods with low GI and without increasing dietary fiber or fat content of the diet.

The term "fasting insulin" "FI or "f-insulin" or fasting plasma insulin (FPI) as used herein are interchangeable and refer to the amount of insulin present in the blood of a human or animal. The fasting insulin level is measured after a fast of approximately 8 hours and can be measured at the same time as the FPG is measured.

The term "30-minutes insulin response" as used herein refers to the insulin levels measured during an Oral Glucose Tolerance Testing (OGTT), 30 minutes after the subject intakes a dose of a simple sugar, for example glucose or dextrose.

The terms "ad libitum diet" as used herein refer to a diet where the amount of daily calories intake of a subject is not restricted to a particular value. A subject following an ad libitum diet is free to eat till satiety.

As used herein a "calorie restricted (CR)" diet provides, for example, about 1200 to about 2000 kcal per day.

As used herein a "low calorie diet (LCD)" provides, for example, from about 800 to 1200 kcal per day.

As used herein a "very low calorie diet (VLCD)" provides, for example, about 800 or fewer kcal per day.

The terms "subject" or "patient" as used herein refer to an individual of one of the species of mammals disclosed herein. A patient is a subject, which has been diagnosed with a particular disorder.

DETAILED DESCRIPTION OF THE INVENTION

Some aspects of the present disclosure relate to methods for predicting dietary weight loss success of a subject, for classifying responsiveness of a subject to a predetermined diet, for selecting a successful weight loss diet for a subject and for maintaining weight or preventing weight re-gain of a subject.

Another aspect of the present disclosure relates to a method for selecting a weight gain diet for a subject in need thereof.

Some other aspects of the present disclosure also relate to methods for inducing weight loss and for treating overweight or obesity in a subject in need thereof.

The methods of the present disclosure are all based on administering a predetermined diet to a subject, based on the subject's fasting blood glucose (FPG) and/or fasting insulin (f-insulin). The invention is also contemplates changing a subject's predetermined diet based on fluctuations or improvements in a subject's fasting blood glucose and/or fasting insulin.

The inventors found that subjects with a high FPG are prone to lose more weight, such as maintain their weight when following a low GL/low GI diet compared to subjects having low FPG and also compared to following a high GL/high GI diet. The inventors also found that subjects with a high FPG are more prone to gain or re-gain weight compared to subjects having low FPG when following a normal diet, i.e. a diet with high GL/high GI.

One aspect of the present disclosure relates to a method for predicting dietary weight loss success of a subject comprising determining the FPG of said subject and classifying the subject as high FPG or low FPG:
  wherein a subject having a high FPG is prone to lose more weight on a low GL/low GI diet than a subject having a normal FPG;
  wherein a subject having a high FPG is prone to lose more weight on a low GL/low GI diet than on a high GL/high GI diet;
  thereby predicting the dietary loss success of said subject.

Another aspect of the present disclosure relates to a method for classifying responsiveness of a subject to a low GL/low GI diet comprising determining the FPG of said subject and classifying the subject as high FPG or low FPG:
  wherein a subject having a high FPG is prone to gain weight on an ad libitum diet with high GL/high GI;
  wherein a subject having a high FPG is prone to maintain or lose weight on an ad libitum diet with low GL/low GI;
thereby classifying responsiveness of said subject to said low GL/low GI diet.

Another aspect of the present disclosure relates to a method for selecting a weight loss diet for a subject comprising:
  determining the FPG of said subject, and
  selecting a libitum diet with low GL/low GI when said subject has a high FPG.

Another aspect of the present disclosure relates to a method for maintaining weight or preventing weight re-gain of a subject comprising determining the fasting blood glucose of said subject and administering to said subject a low GL/low GI ad libitum diet if the FPG of said subject is high.

Another aspect of the present disclosure relates to a method for selecting a weight gain diet for a subject comprising:
  determining the FPG of said subject;
  optionally determining the BMI of said subject; and
  selecting a libitum diet with high GL/high GI when said subject has a high FPG.

In some embodiments, the FPG of a subject is determined and the subject is classified as:
  normal FPG,
  high FPG, or
  very high FPG.

In some embodiments, the f-insulin of a subject is determined and the subject is classified as:
  low f-insulin, or
  high f-insulin.

In some embodiments, the FPG and the f-insulin of a subject is determined and the subject is classified as:
  normal FPG and low f-insulin,
  normal FPG and high f-insulin,
  high FPG and low f-insulin,
  high FPG and high f-insulin,
  very high FPG and low f-insulin,
  very high FPG and high f-insulin.

The methods of the present disclosure relate to the administration of a predetermined diet to a subject in need thereof, based on the FPG and/or f-insulin of said subject. The diets to be administered are any one of the following:
  an ad libitum low GI/low GL diet,
  an ad libitum high GI/high GL diet,
  a low fat diet,
  a high fat diet,
  an ad libitum low fiber diet,
  an ad libitum high fiber diet,
  an ad libitum low GI/low GL diet and an ad libitum low fiber diet,
  an ad libitum low GI/low GL diet and an ad libitum high fiber diet,
  an ad libitum high GI/high GL diet and an ad libitum low fiber diet, or
  an ad libitum high GI/high GL diet and an ad libitum high fiber diet.

Preferably, in all the above-described methods of the invention, an ad libitum diet may be replaced with a calorie restricted diet for further improvement in weight loss.

The diets are described more in detailed in the section below "Diets".

Diets

The present disclosure relates to different types of diets, which are described in detail in the sections below "High GI/high GL and low GI/low GL diets", "High fat diet and low fat diet" and "High fiber diet and low fiber diet". A subject may be provided with any one of the diets disclosed herein based on the subject's FPG and/or f-insulin and/or BMI. The diets may also be combined, for example a subject may be provided with a low GI/low GL diet and a low fiber diet, or with a low GI/low GL diet and high fiber diet, or with a high GI/high GL diet and a low fiber diet, or with a high GI/high GL diet and a high fiber diet.

Preferably, in all the diets described herein, an ad libitum diet may be replaced with a calorie restricted diet for further improvement in weight loss.

High GI/high GL and low GI/low GL diets.

In some embodiments, the diet is a low GI/low GL diet and has a glycemic index (GI) of at least 4 units lower than the GI of the diet the subject was previously following, such as of a diet without low GL/low GI.

In some embodiments, the diet is a low GI/low GL diet and has a glycemic index (GI) of at least 5 units lower, such as of at least 6 units lower, such as of at least 7 units lower, such as of at least 8 units lower, such as of at least 9 units lower, such as of at least 10 units lower than the diet the subject was previously following, such as of a diet without low GL/low GI.

In some embodiments, the diet is a low GI/low GL diet and has a glycemic index (GI) between 20 and 58 units.

In some embodiments, the diet is a low GI/low GL diet and has a glycemic index (GI) between 20 and 30 units, such as between 20 and 40 units, such as between 20 and 50 units, such as between 20 and 55 units, such as between 20 and 58 units.

In some embodiments, the diet is a low GI/low GL diet and has a glycemic index (GI) between 54 and 58 units.

In some embodiments, the diet is a low GI/low GL diet and has a GI of 20 units, such as of 25 units, such as of 30 units, such as of 35 units, such as of 40 units, such as of 45 units, such as of 50 units.

In some embodiments, the diet is a low GI/low GL diet and has a GI of 54 units, such as a GI of 55 units, such as a GI of 56 units, such a GI of 57 units, such as a GI of 58 units.

In some embodiments, the diet is a low GI/low GL diet and has reduced carbohydrate content compared to the carbohydrate content of the diet the subject was previously following, such as of a diet without low GL/low GI.

In some embodiments, the diet is a low GI/low GL diet and has a carbohydrate content accounting for between 0% and 45% of the daily energy intake, such as between 10% and 45% of the daily energy intake, such as between 15% and 45% of the daily energy intake, such as between 20% and 45% of the daily energy intake, such as between 25% and 45% of the daily energy intake, such as between 30% and 45% of the daily energy intake, such as between 35% and 45% of the daily energy intake, such as between 40% and 45% of the daily energy intake.

In some embodiments, the diet is a low GI/low GL diet and has a carbohydrate content accounting for less than 50% of the daily energy intake, such as less than 45% of the daily energy intake, such as less than 40% of the daily energy intake.

In some embodiments, the diet is a low GI/low GL diet and has low carbohydrate content, such as a carbohydrate content accounting for between 40% and 45% of the daily energy intake of a subject.

In some embodiments, the diet is a low GI/low GL diet and has a carbohydrate content accounting for 40% of the daily energy intake of a subject, such as for 41% of the daily energy intake of a subject, such as for 42% of the daily energy intake of a subject, such as for 43% of the daily energy intake of a subject, such as for 44% of the daily energy intake of a subject, such as for 45% of the daily energy intake of a subject.

By reducing the carbohydrate content of a diet and/or by reducing the GI of a diet, the GL is also reduced.

Thus, in some embodiments, the diet is a low GI/low GL diet and has a GL lower than the GL of the diet the subject was previously following, such as of a diet without low GL/low GI.

In some embodiments, the diet is a low GI/low GL diet and has a GL of at least 25 grams/day lower than the GL of the diet the subject was previously following, such as of a diet without low GL/low GI.

In some embodiments, the diet is a low GI/low GL diet and has a GL of at least 30 grams/day lower, such as of at least 35 grams/day lower, such as of at least 40 grams/day lower than the GL of the diet the subject was previously following, such as of a diet without low GL/low GI.

In some embodiments, the diet is a low GI/low GL diet and has a low GL, such as a GL between 10 grams/day and 110 grams/day, such as a GL between 20 grams/day and 110 grams/day, such as a GL between 30 grams/day and 110 grams/day, such as a GL between 40 grams/day and 110 grams/day, such as a GL between 50 grams/day and 110 grams/day, such as a GL between 60 grams/day and 110 grams/day, such as a GL between 70 grams/day and 110 grams/day, such as a GL between 80 grams/day and 110 grams/day, such as a GL between 90 grams/day and 110 grams/day, such as a GL between 100 grams/day and 110 grams/day.

In some embodiments, the diet is a low GI/low GL diet and has a low GL, such as a GL between 100 grams/day and 110 grams/day.

A high GL/high GI diet is characterized by having high carbohydrate content, high GI and thus high GL.

In some embodiments, a high GL/high GI diet is characterized by having a carbohydrate content accounting for at least 50% of the daily energy intake of a subject.

In some embodiments, a high GL/high GI diet is characterized by having a carbohydrate content accounting for between 50% and 55% of the daily energy intake of a subject.

In some embodiments, a high GL/high GI diet is characterized by having a GI of at least 60 units.

In some embodiments, a high GL/high GI diet is characterized by having a GI comprised between 60 and 64 units.

In some embodiments, a high GL/high GI diet is characterized by having a GL of at least 135 grams/day.

In some embodiments, a high GL/high GI diet is characterized by having a GL comprised between 135 grams/day and 140 grams/day.

The skilled person is able to design a low GL/low GI diet and a high GL/high GI diet based on information present in the literature. For example, the "Diogenes Project" has published information on the GI of a plurality of food and can be used to design a low GL/low GI diet. Other sources of information regarding the GI and the GL of a food include the online database Glycemic Index (www.glycemicindex.com) and a table published by Foster-Powell and colleagues (Am J Clin Nutr 2002, 76:5-56).

The GI of a diet can be therefore easily determined. A method for determining the GI of a diet may comprise the following steps:
- determine the amount of carbohydrates in each portion of a meal;
- determine the proportion of carbohydrates of each meal component: divide the amount of carbohydrate of each component by the total amount of carbohydrates of the meal;
- multiply the proportion of carbohydrates of each meal component by the predetermined GI of that component; sum the result of each meal component to obtain the GI of the meal;
- repeat for every meal and make a weighted average to obtain the GI of the diet of a day/week.

According to the methods of the present disclosure, subjects classified as high FPG are prone to lose weight when administered with a low GL/low GI diet.

In contrast, subjects classified as high FPG are less prone to lose weight when administered with a high GL/high GI diet than subjects classified as normal FPG. Moreover, subjects classified as high FPG are prone to gain weight or re-gain weight when following a high GL/high GI diet.

High Fat Diet and Low Fat Diet

In some embodiments the method of the present disclosure relates to a low fat diet or a high fat diet, wherein the low fat diet or the high fat diet is a diet limited by up to 600 kcal/day, such as the daily energy content of the diet is up to 600 kcal lower than the daily energy requirement of the subject. For example, if a subject usually intakes 2000 kcal/day, according to the high fat or low fat diet of the present disclosure the subject should intake at least 1400 kcal/day, such as up to 600 kcal/day less relative to the 2000 kcal/day. The subject following a high fat diet or a low fat diet as disclosed herein may intake between 1400 and 2000 kcal/day, preferably less than 2000 kcal/day and at least 1400 kcal/day.

A low fat diet of the present disclosure is a diet characterized by a fat content between 15 and 30% of the daily energy.

The fat content of a low fat diet is below 30% of the daily energy, such as between 15 and 30% of the daily energy, such as between 15 and 25% of the daily energy, such as between 20 and 25% of the daily energy, such as between 20 and 30% of the daily energy.

In some embodiments, the method of the present disclosure relates to a high fat diet, which is a diet limited by up to 600 kcal/day, such as the daily energy content of the diet is up to 600 kcal lower than the daily energy requirement of the subject, and comprising a fat content between 35 and 50% of the daily energy.

The fat content of a high fat diet is above 35% of the daily energy, such as between 35 and 50% of the daily energy, such as between 40 and 50% of the daily energy, such as between 40 and 45% of the daily energy, such as between 35 and 45% of the daily energy.

High Fiber Diet and Low Fiber Diet

In some embodiments the, method of the present disclosure relates to an ad libitum high fiber diet, which is a diet comprising a fiber intake higher than 3.5 g/kcal, preferably higher than 4 g/kcal and low energy density, such as energy density below 115 kcal/100 g, wherein g are grams of food.

The fiber content of the high fiber diet is above 20 to 45 g/10 MJ or 25 to 45 g/10 MJ.

The energy density of the high fiber diet is below 115 kcal/100 g, such as below 112 kcal/100 g, such as below 110 kcal/100 g, such as below 105 kcal/100 g, such as below 100 kcal/100 g, such as below 95 kcal/100 g, such as below 90 kcal/100 g.

The energy density of the high fiber diet may be comprised between 90 and 115 kcal/100 g, such as between 90 and 112 kcal/100 g, such as between 90 and 110 kcal/100 g, such as between 90 and 105 kcal/100 g, such as between 90 and 100 kcal/100 g.

The high fiber diet is also a diet rich in whole grains.

In some embodiments, the method of the present disclosure relates to an ad libitum low fiber diet, which is a diet comprising a fiber intake lower than 3.5 g/kcal, preferably lower than 3 g/kcal.

The fiber content of the low fiber diet is below 3.5 g/kcal, such as below 3 g/kcal, such below 2.5 g/kcal, such as below 2 g/kcal.

Fasting Plasma Glucose (FPG)

The methods disclosed herein comprise determining the fasting plasma glucose concentration (FPG) of a subject and classifying that subject as normal FPG, high FPG or very high FPG. The measurement of FPG is simple and non-demanding, it is in fact already widely used in combination with other tests for diagnosing diabetes, and subjects with an FPG higher than 125 mg/dl are diabetics, whereas the normal value of FPG is below 100 mg/dl. It is sufficient to collect a small amount of blood from a finger or a vein and so measure the glucose concentration. It measures blood glucose levels after a period of fasting, usually at least eight hours without food or liquid (except water).

Thus, in some embodiments of the present disclosure the normal FPG is an FPG below 100 mg/dl, for example an FPG of 100 mg/dl, or an FPG of 99 mg/dl, or an FPG between 90 and 100 mg/dl, or an FPG between 80 and 100 mg/dl, or an FPG below 90 mg/dl, or an FPG below 80 mg/dl.

In some embodiments of the present disclosure the high FPG is an FPG higher than 100 mg/dl, preferably an FPG between 100 and 115 mg/dl, preferably an FPG between 100 and 125 mg/dl. For example, a high FPG is an FPG higher than 105 mg/dl, such as an FPG higher than 110 mg/dl, such as an FPG between 100 and 105 mg/dl, such as an FPG between 100 and 110 mg/dl, such as an FPG between 100 and 115 mg/dl, such as an FPG between 100 and 120 mg/dl, such as an FPG between 100 and 125 mg/dl.

In some embodiments, the high FPG is higher than 115 mg/dl, such as higher than 125 mg/dl and it is therefore called "very high FPG".

In some embodiments of the present disclosure the very high FPG is an FPG higher than 115 mg/dl, preferably an FPG higher than 125 mg/dl. For example, the very high FPG is an FPG between 115 and 130 mg/dl, such as between 115 and 140 mg/dl, such as between 115 and 150 mg/dl, such as between 115 and 160 mg/dl, such as between 115 and 180 mg/dl.

In some embodiments FPG of a subject may be measured before a weight loss diet or after a weight loss before a weight maintenance diet.

In some embodiments, 120-minutes glucose levels and/or fructosamine levels and/or glycated hemoglobin (HgbA1c) are determined in addition to FPG or instead of FPG.

120-minutes glucose levels are determined by performing a glucose tolerance test (GTT), for example an oral glucose tolerance test (OGTT). An OGTT is performed usually by administering to a subject 75 g dextrose and then blood sampling the subject at −10, −5, 0, 10, 20, 30, 60, 90, and 120 min. The glucose concentration at 120 min after glucose consumption can be used to classify a subject as normoglycemic, prediabetic or diabetic.

Fructosamine levels can be determined by simple tests, similarly to FPG, and they vary following a similar pattern as the blood glucose levels. Therefore, Fructosamine levels can be monitored for a better diabetes management.

Another alternative parameter to blood glucose is glycated hemoglobin (HgbA1c), which, similarly to fructosamine, can be monitored as an indicator of an integrated longer term BG value, and used clinically for a better diabetes management.

Other tests that are useful for determining FPG could be, but not limited to, finger prick blood tests for blood glucose or any wearable or external, blood glucose measurement devices.

Fasting Insulin (f-Insulin or FI)

The methods disclosed herein comprise determining the f-insulin of a subject and classifying the subject as high f-insulin or low f-insulin.

Thus, in some embodiments of the present disclosure the low f-insulin is an f-insulin value below the median for the population having high FPG.

Similarly, the high f-insulin is an f-insulin value above the median for the population having high FPG.

In some embodiments of the present disclosure the low f-insulin is an f-insulin value lower than 13 μIU/ml, such as lower than 11 μIU/ml, such as lower than 10 μIU/ml.

The f-insulin concentration can be easily determined by a test similar to the test for determination of FPG. It is thus sufficient to collect a small amount a blood from a finger or a vein after a fasting period of usually 8 hours and so measure the insulin content. A subject having a fasting serum insulin level greater than 25 μIU/mL is considered insulin resistant.

Other tests that are useful for determining insulin sensitivity which can be used in addition to, or instead of, f-insulin include, but are not limited to: insulin AUC or insulin levels at different time points during glucose tolerance test (OGTT).

Predetermined Diets Based on FPG and FI.

Preferred recommended predetermined diets of the invention include Diet 1, Diet 2, Diet 3, Diet 4, Diet 5, Diet 6, Diet 7, Diet 8, Diet 9 and Diet 10 as set forth in Table 1. Table 1 also sets forth the preferred predetermined diet for a subject based on the subject's fasting glucose and fasting insulin. The values in the table for each macronutrient represent the fraction of total dietary energy, in percent, provided by the macronutrient.

TABLE 1

|  | Below FI of 9.5 uU/mL or optional if FI is between 9.5 to 13 uU/mL* | Above FI of 13 uU/mL or optional if FI is between 9.5 to 13 uU/mL* |
|---|---|---|
| **FPG >125 mg/dL | Diet 9<br>Carbohydrate: 34 (32-36)%<br>Protein: 21 (19-23)%<br>Fat: 45 (43-47)%<br>AL<br>Fiber: >20 g/10 MJ<br>Added sugar: <5E % | Diet 10<br>Carbohydrate: 30 (28-32)%<br>Protein: 25 (23-27)%<br>Fat: 45 (43-47)%<br>AL<br>Fiber: >20 g/10 MJ<br>Added sugar: <5E % |
| FPG 115-125 mg/dL | Diet 7<br>Carbohydrate: 39 (37-41)%<br>Protein: 21 (19-23)%<br>Fat: 40 (38-42)%<br>AL<br>Fiber: >25 g/10 MJ<br>(preferably >35)<br>Added sugar: <10E %<br>(preferably <5E %) | Diet 8<br>Carbohydrate: 33 (31-35)%<br>Protein: 25 (23-27)%<br>Fat: 42 (40-44)%<br>AL<br>Fiber: >20 g/10 MJ<br>Added sugar: <5E % |
| FPG 100-115 mg/dL | Diet 5<br>Carbohydrate: 44 (42-46)%<br>Protein: 21 (19-23)%<br>Fat: 35 (33-37)%<br>AL<br>Fiber: >25 g/10 MJ<br>(preferably >35)<br>Added sugar: <10E %<br>(preferably <5E %) | Diet 6<br>Carbohydrate: 37 (35-39)%<br>Protein: 25 (23-27)%<br>Fat: 38 (36-40)%<br>CR<br>Fiber: >25 g/10 MJ<br>Added sugar: <10E %<br>(preferably <5E %) |
| FPG 90-100 mg/dL | Diet 3<br>Carbohydrate: 49 (47-51)%<br>Protein: 21 (19-23)%<br>Fat: 30 (28-32)%<br>AL<br>Fiber: >25 g/10 MJ<br>(preferably >35)<br>Added sugar: <15E %<br>(preferably <5E %) | Diet 4<br>Carbohydrate: 40 (38-42)%<br>Protein: 25 (23-27)%<br>Fat: 35 (33-37)%<br>CR<br>Fiber: >25 g/10 MJ<br>Added sugar: <10E %<br>(preferably <5E %) |
| FPG <90 mg/dL | Diet 1<br>Carbohydrate: 54 (52-56)%<br>Protein: 21 (19-23)%<br>Fat: 25 (23-27)%<br>CR<br>Fiber: >25 g/10 MJ<br>(preferably >35)<br>Added sugar: <15E %<br>(preferably <5E %) | Diet 2:<br>Carbohydrate: 30 (28-32)%<br>Protein: 25 (23-27)%<br>Fat: 45 (43-47)%<br>AL<br>Fiber: >20 g/10 MJ<br>Added sugar: <5E % |

AL—Ad Libitum diet is optional as an alternative to caloric restriction, especially for the long term
CR—Caloric restricted diet would be preferable
*For individuals having FI between 9.5 to 13 uU/mL there are two optional diets as described above. For example, an individual having FPG of 130 mg/dL and FI of 11 uU/mL could be assigned to different diet combinations with a range of carbohydrate between 28% and 36%, which is the combined range of the diets on the two FI ranges.
**Individuals treated with diabetes medication such as Metformin or others should be treated as if their FPG is greater than 125 mg/dL, regardless of what their tested FPG is due to normalization of FPG by the medication.
Note:
The energy percentage from carbohydrates is available carbohydrates and therefore do not include fibers. For example: an individual consumes 10 MJ. If consuming 40, 40, and 20E % from available carbohydrates, fats and proteins, respectively you would immediately think that 4, 4, and 2 MJ of energy comes from these macronutrients. However, if fibers contribute with 0.5 MJ these is only 9.5 MJ to split between the three macronutrients-.comes from these macronutrients. This method could be optionally simplified by averaging the parameters of the following diets:
Diet 1 with Diet 3 for normoglycemic individuals, as well as Diet 2 with Diet 4
Diet 5 with Diet 7 for Prediabetics individuals, as well as Diet 6 with diet 8
Normoglycemic, Prediabetic and Diabetic status could be defined by other methods instead of FPG, including by standard acceptable methods such as HbA1C or OGTT criteria.
High and Low Fasting Insulin levels (the right versus the left columns of the table) could be replaced by the median level of the population of different insulin resistance measurements, such as Insulin AUC or insulin levels at different time points during glucose tolerance test.

Therefore the invention provides methods for predicting dietary weight loss success of a subject comprising, determining the fasting plasma glucose (FPG) and the fasting insulin (FI) of said subject, classifying the subject with respect to the level of FPG and/or f-insulin, and predicting the dietary weight loss success of said subject in view of a predetermined diet wherein the predetermined diet associated with subject's determined levels of FPG and/or F-insulin are selected from the group consisting of: when the subject's FPG is less than about 90 mg/dL and the subject's FI is below about 9.5 uU/mL or optionally the subject's FI is between about 9.5 to about 13 uU/mL, the predetermined diet comprises Diet 1; when the subject's FPG is less than about 90 mg/dL and the subject's FI is above about 13 uU/mL or optionally the subject's FI is between about 9.5 to about 13 uU/mL, the predetermined diet comprises Diet 2; when the subject's FPG is between about 90-100 mg/dL and the subject's FI is below about 9.5 uU/mL or optionally the subject's FI is between about 9.5 to about 13 uU/mL, the predetermined diet comprises Diet 3; when the subject's FPG is between about 90-100 mg/dL and the subject's FI is above about 13 uU/mL or optionally the subject's FI is between about 9.5 to about 13 uU/mL, the predetermined diet comprises Diet 4; when the subject's FPG is between about 100-115 mg/dL and the subject's FI is below about 9.5 uU/mL or optionally the subject's FI is between about 9.5 to about 13 uU/mL, the predetermined diet comprises Diet 5; when the subject's FPG is between about 100-115 mg/dL and the subject's FI is above about 13 uU/mL or optionally the subject's FI is between about 9.5 to about 13 uU/mL, the predetermined diet comprises Diet 6; when the subject's FPG is between about 115-125 mg/dL and the subject's FI is below about 9.5 uU/mL or optionally the subject's FI is between about 9.5 to about 13 uU/mL, the predetermined diet comprises Diet 7; when the subject's FPG is between about 115-125 mg/dL and the subject's FI is above about 13 uU/mL or optionally the subject's FI is between 9.5 to 13 uU/mL, the predetermined diet comprises Diet 8; when the subject's FPG is greater than about 125 mg/dL and the subject's FI is below about 9.5 uU/mL or optionally the subject's FI is between about 9.5 to about 13 uU/mL, the predetermined diet comprises Diet 9; and when the subject's FPG is between greater than about 125 mg/dL and the subject's FI is above about 13 uU/mL or optionally the subject's FI is between about 9.5 to about 13 uU/mL, the predetermined diet comprises Diet 10.

The invention further provides methods for promoting weight loss in a subject comprising administering a predetermined diet to a subject based on the subject's fasting plasma glucose (FPG) in combination with the subject's fasting insulin (FI) wherein the predetermined diet associated with subject's FPG and f-insulin is selected from the group consisting of: when the subject's FPG is less than about 90 mg/dL and the subject's FI is below about 9.5 uU/mL or optionally the subject's FI is between about 9.5 to about 13 uU/mL, the predetermined diet comprises Diet 1; when the subject's FPG is less than about 90 mg/dL and the subject's FI is above about 13 uU/mL or optionally the subject's FI is between about 9.5 to about 13 uU/mL, the predetermined diet comprises Diet 2; when the subject's FPG is between about 90-100 mg/dL and the subject's FI is below about 9.5 uU/mL or optionally the subject's FI is between about 9.5 to about 13 uU/mL, the predetermined diet comprises Diet 3; when the subject's FPG is between about 90-100 mg/dL and the subject's FI is above about 13 uU/mL or optionally the subject's FI is between about 9.5 to about 13 uU/mL, the predetermined diet comprises Diet 4; when the subject's FPG is between about 100-115 mg/dL and the subject's FI is below about 9.5 uU/mL or optionally the subject's FI is between about 9.5 to about 13 uU/mL, the predetermined diet comprises Diet 5; when the subject's FPG is between about 100-115 mg/dL and the subject's FI is above about 13 uU/mL or optionally the subject's FI is between about 9.5 to about 13 uU/mL, the predetermined diet comprises Diet 6; when the subject's FPG is between about 115-125 mg/dL and the subject's FI is below about 9.5 uU/mL or optionally the subject's FI is between about 9.5 to about 13 uU/mL, the predetermined diet comprises Diet 7; when the subject's FPG is between about 115-125 mg/dL and the subject's FI is above about 13 uU/mL or optionally the subject's FI is between 9.5 to 13 uU/mL, the predetermined diet comprises Diet 8; when the subject's FPG is greater than about 125 mg/dL and the subject's FI is below about 9.5 uU/mL or optionally the subject's FI is between about 9.5 to about 13 uU/mL, the predetermined diet comprises Diet 9; and when the subject's FPG is greater than about 125 mg/dL and the subject's FI is above about 13 uU/mL or optionally the subject's FI is between about 9.5 to about 13 uU/mL, the predetermined diet comprises Diet 10.

The invention also provides changing a subject's predetermined diet based on fluctuations or improvements in the patient's FPG and FI for to optimize weight loss in the patient. For example, if a patient's original FPG is greater than about 125 mg/dL and after following predetermined Diet 10 for a period of time (e.g. days, weeks or months) the patient's FPG is determined to be less than about 9.5, the patient may be moved to predetermined Diet 1 or Diet 2 depending on the patient's FI.

Preferably, for those patients whom the fiber intake before the treatment was the same or above the amount which is recommended based on Table 1, the recommended carbohydrate intake should be reduced by 10 to 20%, and the protein and fat intake should be increased instead in equal amounts to balance the diet for at least a period of at least 1 week, preferably at least 2 weeks, preferably at least 3 weeks, preferably at least 4 weeks preferably at least 5 weeks, preferably at least 6 weeks preferably at least 7 weeks preferably at least 8 weeks or more prior to commencing a diet of Table 1.

Preferably, patients who receive a prediction for optimized weight loss and a recommendation to follow a particular diet in accordance with Table 1 are Caucasian patients.

Preferably, patients taking medications to treat diabetes (e.g. metformin, glimepride, glipizide) should be classified as having an FPG of greater than 125 mg/dL regardless of their actual FPG due to potential FPG normalization by the medications. Therefore, the invention provides methods for promoting weight loss in patients taking diabetes medications comprising administering to the patient Diet 9 or Diet 10 of Table 1.

Underweight, Overweight and Obese Subject

In some embodiments, the methods disclosed herein are directed to obese or overweight subjects.

In some embodiments, the FPG of a subject is measured and the subject is classified as high FPG or normal FPG. Both high FPG subjects and normal FPG subjects lose weight when they undergo a low calorie diet, although high FPG subjects lose weight to a lower extent compared to normal FPG subjects. However, some subjects are prone to quickly regain weight as soon as they interrupt the low calorie diet. The methods of the present disclosure solve this problem by identifying the high FPG subjects as those that regain weight as soon as they interrupt a low calorie diet. Moreover, the disclosed methods allow the selection of a targeted diet, i.e., a low GL/low GI diet, for the high FPG subjects so that these subjects will maintain weight or lose more weight even when following an ad libitum diet.

In some embodiments, the FPG of a subject is determined and the subject is classified as normal or normoglycemic if the FPG is lower than 100 mg/dl. If the FPG is comprised between 100 mg/dl and 125 mg/dl, the subject is classified as prediabetic. If the FPG is higher than 125 mg/dl, the subject is classified as likely to be diabetic.

Thus, in some embodiments, the subjects classified as high FPG are affected by prediabetes or diabetes.

In some embodiments, the subjects classified as high FPG are diabetics, for example the subjects having high FPG are affected by type 2 diabetes.

Prediabetes is the precursor stage to diabetes mellitus in which none or only few of the symptoms required to label a subject as diabetic are present, but blood glucose is abnormally high. A subject with prediabetes may develop diabetes in the future.

Usually prediabetic subjects do not present distinct signs or symptoms. They may present symptoms typical of type 2 diabetes mellitus such as:
  constant hunger,
  weight gain,
  flu-like symptoms, including weakness and fatigue,
  blurred vision,
  slow healing of cuts or bruises,
  tingling or loss of feeling in hands or feet,
  recurring gum or skin infections,
  recurring vaginal or bladder infections, and
  high BMI (Body Mass Index) result.

In some embodiments, the methods disclosed herein are directed to subjects affected by overweight.

In some embodiments, the methods disclosed herein are directed to subjects affected by obesity.

In some embodiments the subject in need of the disclosed methods has BMI of 25 or more, such as 30 or more, for example 35 or more, such as 40 or more. In another embodiment, the subject in need of the disclosed methods has a waist/hip ratio of at least 0.80, for example 0.80-0.84, such as at least 0.85 (female) or at least 0.90, for example 0.9-0.99, such as above 1.00 (male).

The subject in need of the disclosed methods may present one or more of the following symptoms:
  Elevated blood pressure: ≥140/90 mmHg;
  Dyslipidemia: triglycerides (TG): ≥1.695 mmol/L and high-density lipoprotein cholesterol (HDL-C)≤0.9 mmol/L (male), ≤1.0 mmol/L (female);
  Central obesity: waist:hip ratio >0.90 (male); >0.85 (female), or body mass index >30 kg/m2; and
  Microalbuminuria: urinary albumin excretion ratio ≥20 μg/min or albumin:creatinine ratio ≥30 mg/g.

In some embodiments, the subjects have high FPG and are underweight, such as severely underweight. Subjects with a BMI below 18.5, such as below 18, such as below 16 are classified as underweight.

In some embodiments, the methods disclosed herein are directed to underweight subjects, who have difficulties in gaining weight and reach a normal weight, preferably the underweight subject has a BMI below 18.5.

Thus, in some embodiments the subjects having high FPG and being underweight have difficulties in gaining weight and reach a normal weight.

In some embodiments, a subject having high FPG is also affected by inherited, acquired and iatrogenic insulin resistance.

In some embodiments, the inherited, acquired and iatrogenic insulin resistance may be associated with polycystic ovary syndrome (PCOS), glucocorticoid treatment, psychotropic drugs, insulin treatment or other diseases.

Methods for Inducing Weight Loss One aspect of the present disclosure relates to a method for predicting dietary weight loss success of a subject comprising:
  determining the fasting blood glucose (FPG) and/or the fasting insulin (f-insulin) of said subject,
  classifying the subject with respect to the level of FPG and/or f-insulin, and
  predicting the dietary weight loss success of said subject in view of a predetermined diet.

In one embodiment, the method for predicting dietary weight loss success of a subject comprises determining the FPG of a subject and classifying said subject as normal FPG, high FPG or very high FPG:
  wherein a subject having a high or very high FPG is prone to lose more weight on a low GL/low GI diet than a subject having a normal FPG;
  wherein a subject having a high or very high FPG is prone to lose more weight on a low GL/low GI diet than on a high GL/high GI diet;
  wherein a subject having a high or normal FPG is prone to lose more weight on a high fiber diet and/or on a high fat diet than a subject having a very high FPG; and
  wherein a subject having a high or normal FPG is prone to lose more weight on a high fiber diet and/or on a high fat diet than on a low fiber and/or on a low fat diet.

In some embodiments, subjects classified as high FPG and having f-insulin below the median value, for example below 13 µIU/mL, are more prone to lose weight when administered with a low GL/low GI diet than subjects classified as high FPG and having f-insulin above the median, for example above 13 µIU/mL.

In some embodiments, overweight or obese subjects classified as high FPG are recommended to follow a low GL/low GI diet, such as to reduce the glycemic load (GL) of their diet.

In some embodiments, subjects classified as high FPG and having f-insulin below the median value, for example below 13 µIU/mL, are more prone to lose weight when administered with a low GL/low GI diet than subjects classified as normal FPG.

In some embodiments, subjects classified as high FPG and having f-insulin below the median value, for example below 13 µIU/mL, are more prone to lose weight when administered with a low GL/low GI diet than when administered a high GL/high GI diet.

In one embodiment, the method for predicting dietary weight loss success of a subject comprises determining the f-insulin of a subject and classifying said subject as low f-insulin or high f-insulin:
  wherein a subject having a low f-insulin is prone to lose more weight on a high fat diet and/or on a high fiber diet than a subject having a high f-insulin, and
  wherein a subject having a low f-insulin is prone to lose more weight on a high fat diet and/or on a high fiber diet than on a low fiber diet and/or on a low fat diet.

In one embodiment, the method for predicting dietary weight loss success of a subject comprises determining the FPG and the f-insulin of a subject and classifying said subject as normal FPG low f-insulin, normal FPG high f-insulin, high FPG low f-insulin, high FPG high f-insulin, very high FPG low f-insulin, or very high FPG high f-insulin:
  wherein a subject having a normal FPG and a low f-insulin is prone to lose more weight on a low fat low calorie diet and/or on a high fiber low calorie diet than a subject having very high FPG and low f-insulin or than a subject having normal FPG and high f-insulin,
  wherein a subject having a normal FPG and a low f-insulin is prone to lose more weight on a low fat low calorie diet and/or on a high fiber low calorie diet than on a high fat low calorie diet and/or on a low fiber low calorie diet,
  wherein a subject having a high FPG and a low f-insulin is prone to lose more weight on a high fat low calorie diet and/or on a high fiber low calorie diet and/or on a low GI/low GL diet than a subject having normal FPG and low f-Insulin or than a subject having normal FPG and high f-insulin,
  wherein a subject having a high FPG and a low f-insulin is prone to lose more weight on a high fat low calorie diet and/or on a high fiber low calorie diet than on a low fat low calorie diet and/or on a low fiber low calorie diet and/or on a high GI/high GL diet;
  wherein a subject having a very high FPG and a low f-insulin is prone to lose more weight on a high fat low calorie diet and/or on a low GI/low GL diet than a subject having normal FPG and low f-Insulin, and
  wherein a subject having a very high FPG and a low f-insulin is prone to lose more weight on a high fat low calorie diet and/or on a low GI/low GL diet than on a low fat low calorie diet and/or on a high GI/high GL diet.

One aspect of the present disclosure relates to a method for classifying responsiveness of a subject to a predetermined diet comprising determining the FPG and/or the f-insulin of said subject and classifying the subject with respect to the level of FPG and/or f-insulin.

In one embodiment the method for classifying responsiveness of a subject to a predetermined diet comprises determining the FPG of said subject and classifying said subject as normal FPG, high FPG or very high FPG:
  wherein a subject having a high or a very high FPG is prone to gain weight on an ad libitum diet with high GL/high GI,
  wherein a subject having a high or a very high FPG is prone to maintain or lose weight on an ad libitum diet with low GL/low GI,
  wherein a subject having a very high FPG is prone to maintain or lose weight on a high fat low calorie diet,
  wherein a subject having a high FPG or normal FPG is prone to maintain or lose weight on a low fat low calorie diet and/or on a high fiber low calorie diet, and
  wherein a subject having a low f-insulin is prone to gain weight on an ad libitum diet with high GL/high GI.

In one embodiment the method for classifying responsiveness of a subject to a predetermined diet comprises determining the-insulin of a subject and classifying said subject as low f-insulin or high f-insulin wherein a subject having a low f-insulin is prone to maintain or lose weight on an ad libitum diet with high GL/high GI or on a high fat low calorie diet and/or on a high fiber low calorie diet.

In one embodiment the method for classifying responsiveness of a subject to a predetermined diet comprises determining the FPG and the f-insulin of a subject and classifying said subject as normal FPG low f-insulin, normal FPG high f-insulin, high FPG low f-insulin, high FPG high f-insulin, very high FPG low f-insulin, or very high FPG high f-insulin:
  wherein a subject having a high or a very high FPG and a low f-insulin is prone to gain weight on an ad libitum diet with high GL/high GI,
  wherein a subject having a high or a very high FPG and a low f-insulin is prone maintain or lose weight on an ad libitum diet with high GL/high GI, wherein a subject having a normal or a high FPG and a low f-insulin is prone to maintain or lose weight on a low fat low calorie diet and/or on a high fiber low calorie diet, and wherein a subject having a very high FPG and a low f-insulin is prone maintain or lose weight on a high fat low calorie diet.

One aspect of the present disclosure relates to a method for selecting a weight loss and/or a maintenance diet for a subject comprising:

determining the FPG and/or the f-insulin of said subject; and selecting a diet based on the level of FPG and/or f-insulin of said subject.

In one embodiment the method for selecting a weight loss and/or a maintenance diet for subject in need thereof comprises determining the FPG of said subject:

wherein an ad libitum high GI/high GL diet or a low fat low calorie diet and/or a high fiber low calorie diet is selected for a subject having normal FPG, wherein an ad libitum low GI/low GL diet or a low fat low calorie diet and/or a high fiber low calorie diet is selected for a subject having high FPG, and wherein an ad libitum low GI/low GL diet or a high fat low calorie diet and/or a high fiber low calorie diet is selected for a subject having very high FPG.

In one embodiment the method for selecting a weight loss and/or a maintenance diet for subject in need thereof comprises determining the f-insulin of said subject:

wherein an ad libitum low GI/low GL diet or a low fat low calorie diet and/or a high fiber low calorie diet is selected for a subject having low f-insulin, and wherein an ad libitum low GI/low GL diet or a high fat low calorie diet and/or a high fiber low calorie diet is selected for a subject having high f-insulin.

In one embodiment the method for selecting a weight loss and/or a maintenance diet for subject in need thereof comprises determining the FPG and the f-insulin of said subject:

wherein a low GI/low GL diet and/or a low fat low calorie diet and/or a high fiber low calorie diet is selected for a subject having normal FPG and low f-insulin, and wherein a low GI/low GL diet and/or a high fat low calorie diet and/or a high fiber low calorie diet is selected for a subject having high or very high FPG and low f-insulin.

One aspect of the present disclosure relates to a method for maintaining weight or preventing weight re-gain of a subject comprising determining the FPG and/or the f-insulin of said subject and providing to said subject a predetermined diet, thereby maintaining weight or preventing weight re-gain of said subject.

In one embodiment the method for maintaining weight or preventing weight re-gain of a subject in need thereof comprises determining the FPG of said subject:

wherein an ad libitum high GI/high GL diet or a low fat low calorie diet and/or a high fiber low calorie diet is provided to a subject having normal FPG, wherein an ad libitum low GI/low GL diet or a low fat low calorie diet and/or a high fiber low calorie diet is provided to a subject having high FPG, and wherein an ad libitum low GI/low GL diet or a high fat low calorie diet and/or a high fiber low calorie diet is provided to a subject having very high FPG.

In one embodiment the method for maintaining weight or preventing weight re-gain of a subject in need thereof comprises determining the f-insulin of said subject:

wherein an ad libitum low GI/low GL diet or a low fat low calorie diet and/or a high fiber low calorie diet is provided to a subject having low f-insulin, and wherein an ad libitum low GI/low GL diet or a high fat low calorie diet and/or a high fiber low calorie diet is provided to a subject having high f-insulin.

In one embodiment the method for maintaining weight or preventing weight re-gain of a subject in need thereof comprises determining the FPG and f-insulin of said subject:

wherein a low GI/low GL diet and/or a low fat low calorie diet and/or a high fiber low calorie diet is provided to a subject having normal FPG and low f-insulin, and wherein a low GI/low GL diet and/or a high fat low calorie diet and/or a high fiber low calorie diet is provided to a subject having high or very high FPG and low f-insulin.

One aspect of the present disclosure relates to a method of inducing weight loss in a subject in need thereof, the method comprising administering a predetermined diet to said subject, wherein the diet is chosen based on the FPG and/or f-insulin of said subject, thereby inducing weight loss in said subject.

One aspect of the present disclosure relates to a method of inducing weight loss and particularly fat-loss in a subject in need thereof, the method comprising administering a predetermined diet to said subject, wherein the diet is chosen based on the FPG and/or f-insulin of said subject, thereby inducing weight loss and particularly fat loss in said subject.

A further aspect of the present disclosure relates to method of treating overweight or obesity in a subject in need thereof, the method comprising administering a predetermined diet to said subject, wherein the diet is chosen based on the FPG and/or f-insulin of said subject, thereby treating overweight or obesity in said subject.

In some embodiments, the method of inducing weight loss and the method of treating overweight or obesity comprise administering an ad libitum diet with low GI/low GL to a subject having:

high or very high FPG, or high or very high FPG and low f-insulin.

In some embodiments, the method of inducing weight loss and the method of treating overweight or obesity comprise administering an ad libitum diet with high GI/high GL to a subject having:

normal FPG, or normal FPG and low f-insulin.

In some embodiments, the method of inducing weight loss and the method of treating overweight or obesity comprise administering a low fat low calorie diet to a subject having:

normal or high FPG, or normal or high FPG and low f-insulin.

In some embodiments, the method of inducing weight loss and the method of treating overweight or obesity comprise administering a high fat low calorie diet to a subject having:

very high FPG, or very high FPG and low f-insulin.

In some embodiments, the method of inducing weight loss and the method of treating overweight or obesity comprise administering a high fiber low calorie diet to a subject having:

high FPG, or normal or very high FPG and low f-insulin.

The diets, in particular the diet with low GI/low GL, the diet with high GI/high GL, the low fat low calorie diet, the high fat low calorie diet and the high fiber low calorie diet are described in detail in the section above "Diets".

In some embodiments, the methods disclosed herein further comprise administering a therapeutic agent that stimulates insulin secretion and/or a therapeutic agent that reduces insulin resistance to a subject having high FPG and affected by inherited, acquired and iatrogenic insulin resistance so that the weight loss success or the weight maintenance success of the low GL/low GI ad libitum diet is increased.

Therefore, in some embodiments a subject classified as high FPG follows a low GL/low GI ad libitum diet or a high fiber low calorie diet and/or a high fat low calorie diet and is administered with a therapeutic agent that stimulates insulin secretion and/or a therapeutic agent that reduces insulin resistance.

In some embodiments, the therapeutic agent that stimulates insulin secretion and/or a therapeutic agent that reduces insulin resistance may be GLP-1 analogues, metformin, sodium-glucose co-transporter type 2 (SGLT2) inhibitors or other therapeutic agents that the skilled person finds suitable.

In some embodiments, subjects classified as high FPG and following a low GL/low GI diet lose fat mass in addition to weight.

The subjects following any of the diets disclosed herein and so losing weight, lose also fat mass.

Thus, in some embodiment the weight loss is at least in part due to a loss of a fat mass.

The predictive power of the methods disclosed herein can be further increased by determining the f-insulin and the 30-minutes insulin response of the subjects classified as high FPG.

The 30-minutes insulin response is measured via a conventional OTTG. Following an overnight fast, an oral glucose tolerance test (OGTT) is performed usually by administering to a subject 75 g dextrose and then blood sampling the subject at −10, −5, 0, 10, 20, 30, 60, 90, and 120 min. The insulin concentration at 30 min after glucose consumption is used as a measure of insulin response (insulin-30) (Ebbeling et al. 2007).

There is no significant correlation between subjects classified as high FPG and subjects having 30-min insulin response above the median, for example above 57.5 µIU/mL (Ebbeling et al. 2007). Moreover, 30-min insulin response and f-insulin are also scarcely correlated. Therefore, it is possible to classify subjects with high FPG in even smaller groups and so offer them a more targeted diet for losing weight such as for maintaining weight.

In some embodiments, a subject classified as high FPG and further having 30-min insulin response above the median is prone to lose more weight than a subject having high FPG and 30-min insulin response below the median.

In some embodiments, a subject classified as high FPG and 30-min insulin response above the median is prone to lose more weight on a low GL/low GI diet than a subject having a normal FPG.

In some embodiments, a subject classified as high FPG, having f-insulin below the median and further having 30-min insulin response above the median is prone to lose more weight on a low GL/low GI diet than on a high GL/high GI diet.

In some embodiments, a subject classified as high FPG, having f-insulin below the median and further having 30-min insulin response above the median is prone to lose more weight than a subject having high FPG, f-insulin below the median and 30-min insulin response below the median.

In some embodiments, a subject classified as high FPG, having f-insulin below the median and further having 30-min insulin response above the median is prone to lose more weight on a low GL/low GI diet than a subject having a normal FPG.

In some embodiments, a subject classified as high FPG, having f-insulin below the median and further having 30-min insulin response above the median is prone to lose more weight on a low GL/low GI diet than on a high GL/high GI diet.

A 30-minutes insulin response lower than 57.5 µIU/mL is considered herein as being below the median (Ebbeling et al. 2007). A 30-minutes insulin response higher than 57.5 µIU/mL is considered herein as being above the median (Ebbeling et al. 2007).

Method for Selecting a Weight Gain Diet

One aspect of the present disclosure relates to a method for selecting a weight gain diet for a subject comprising:
  determining the FPG and/or the f-insulin of said subject;
  determining the BMI of said subject; and
  selecting a diet based on the level of FPG and/or f-insulin of said subject, thereby selecting a weight gain diet for said subject.

In some embodiments a subject having high or very high FPG, BMI below 18 and following a high GL/high GI diet is more prone to gain weight than a subject having high or very high FPG, BMI below 18 and following a low GL/low GI diet.

In some embodiments a subject having high f-insulin, BMI below 18 and following a high GL/high GI diet is more prone to gain weight than a subject having high f-insulin, BMI below 18 and following a low GL/low GI diet.

In some embodiments a subject having high or very high FPG and low f-insulin, BMI below 18 and following a high GL/high GI diet is more prone to gain weight than a subject having high or very high FPG and low f-insulin, BMI below 18 and following a low GL/low GI diet.

In some embodiments, subjects with a high FPG and being underweight are provided with an ad libitum high GL/high GI diet as disclosed herein.

In some embodiments, underweight subjects with a high FPG and following a high GL/high GI diet are more prone to gain weight than underweight subjects with a high FPG and following a low GL/low GI diet.

EXAMPLES

Example 1: Pre-Treatment Fasting Plasma Glucose and Insulin Modify Dietary Weight Loss Success: Results from Three Randomized Clinical Trials The purpose of this study was to investigate fasting plasma glucose (FPG) and FI as prognostic markers for weight loss and weight loss maintenance when allocated to pairs of diets varying in macronutrient content, glycaemic load and fibre/wholegrain from three randomized clinical trials. This was done in order to find the best weight loss and weight loss maintenance diet for patients with different glycaemic and insulinemic status.

Subjects and Methods

Figure 1:
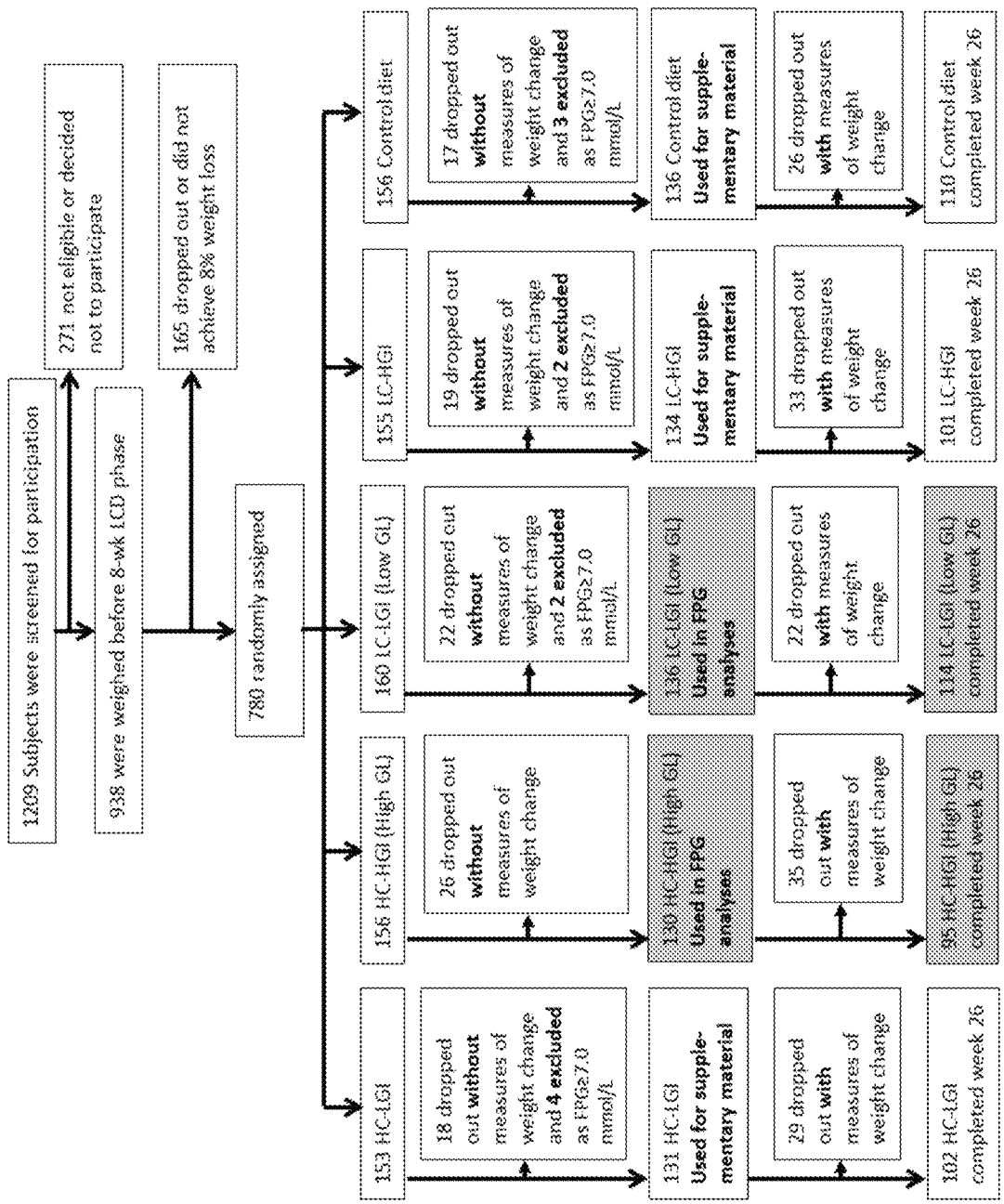
FIG. 1 is a participant flow diagram for participants in the DiOGenes study.
Figure 2:
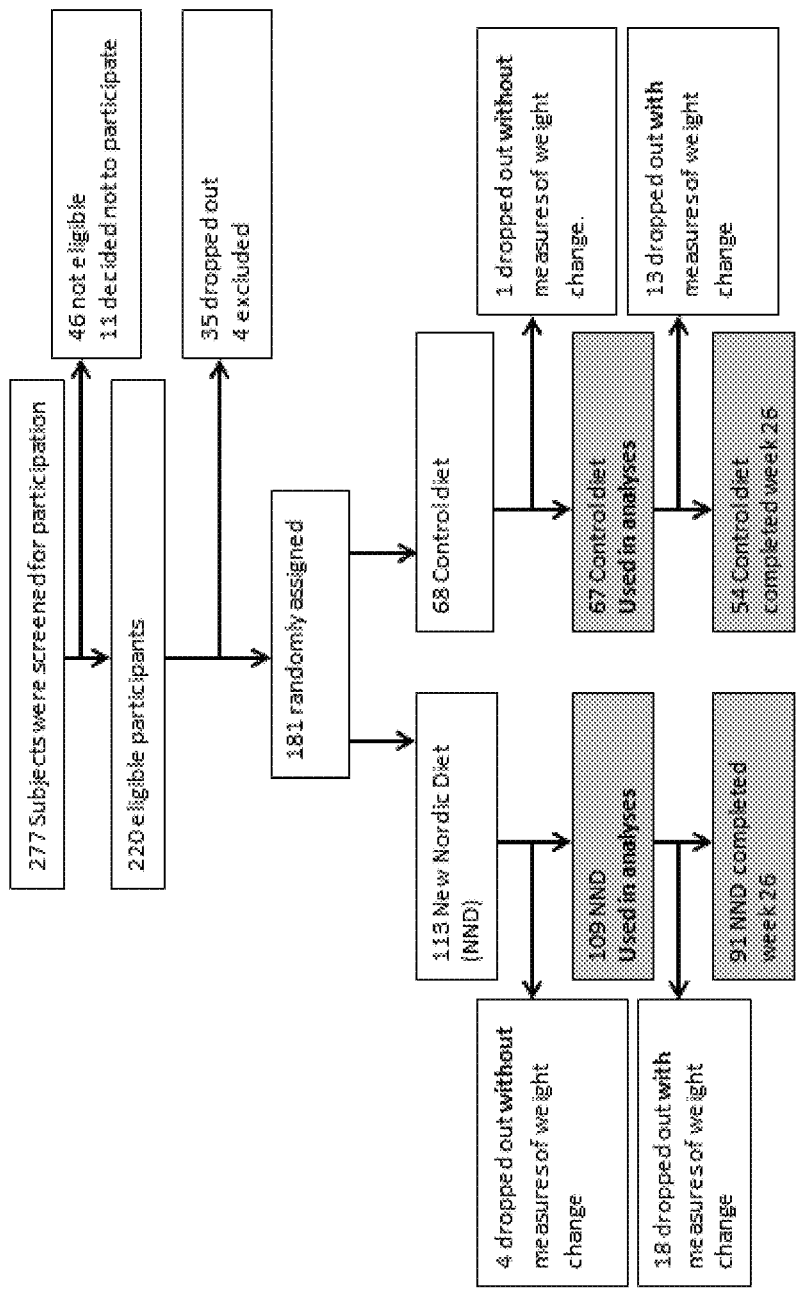
FIG. 2 is a participant flow diagram for participants in the SHOPUS study.
Figure 3:
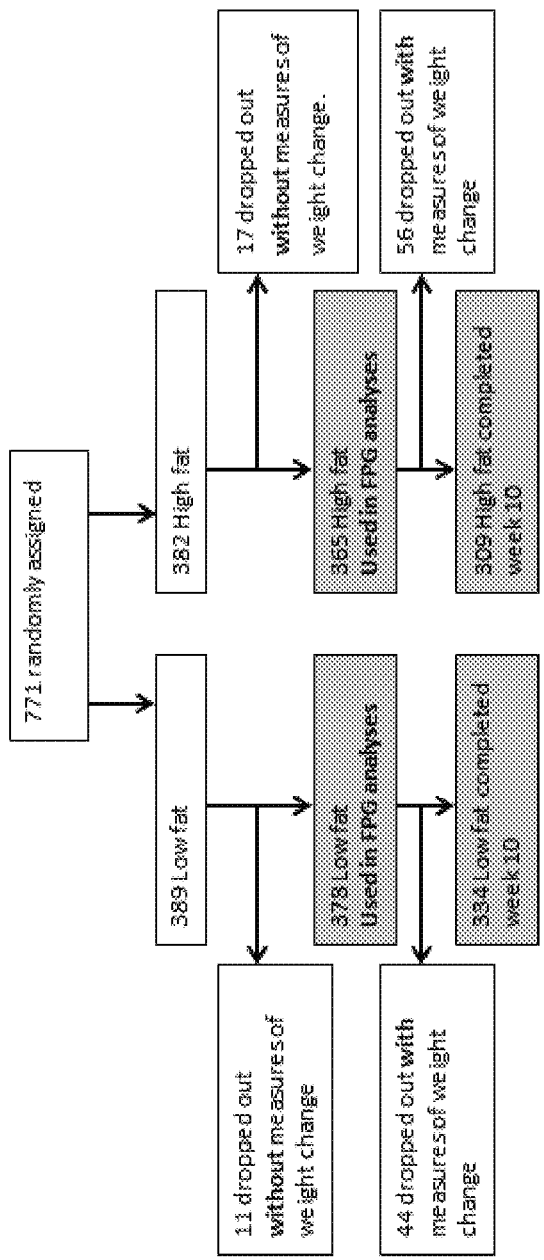
FIG. 3 is a participant diagram for participants in the NUGENBOG study.

We reanalyzed three randomized clinical trials—the Diet, Obesity, and Genes (DiOGenes) conducted in eight European countries (9, 10), the OPUS Supermarket intervention (SHOPUS) conducted in Denmark (11), and the Nutrient-gene interactions in human obesity (NUGENOB) conducted in seven European countries (12). Participant flow diagram of the three studies can be found in supplementary material (FIGS. 1-3). The research protocols were approved by the ethics committees and all human participants gave written informed consent.

Figure 7:
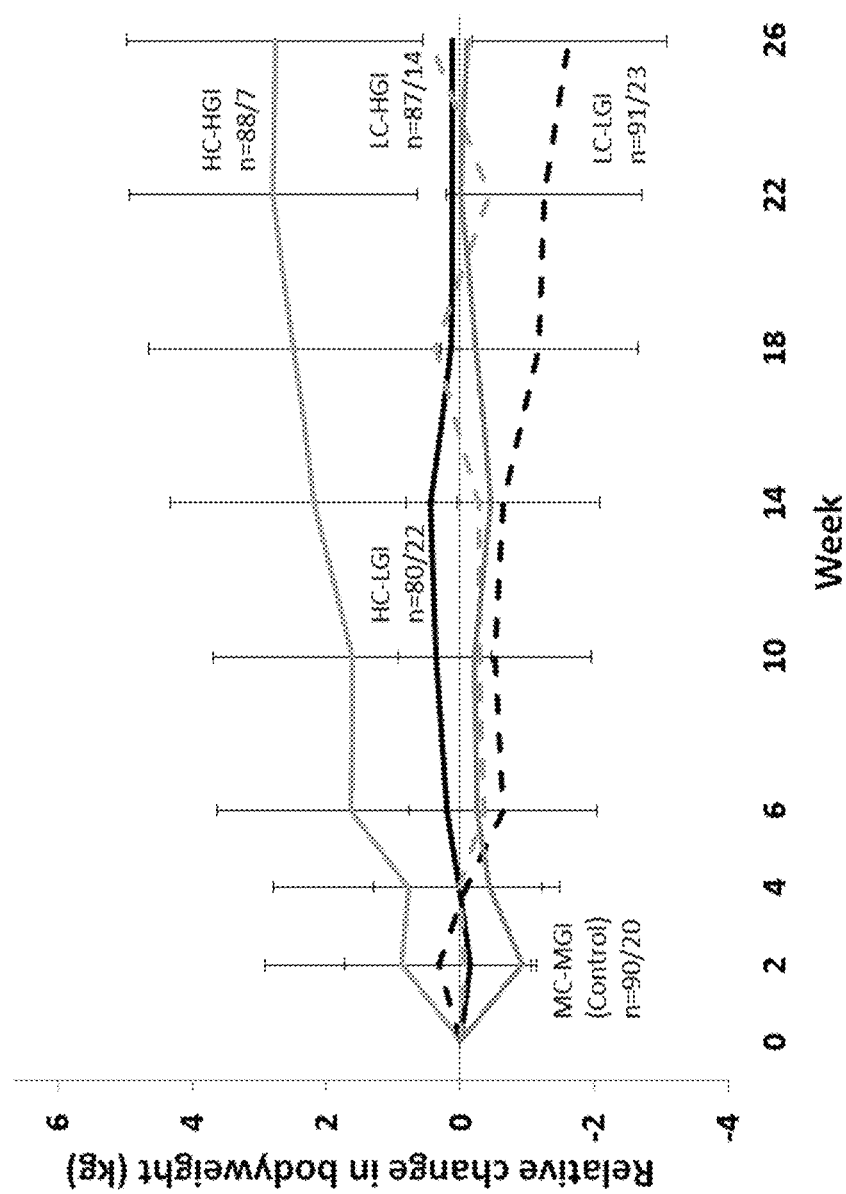
FIG. 7 is a line graph showing change in body weight between prediabetic and normo-glycaemic participants according to the five different ad libitum weight maintenance diets in DiOGenes. HC-HGI, high carbohydrate-high glycaemic index (also called high Glycaemic-load diet); HC-LGI, high carbohydrate-low glycaemic index; LC-HGI, low carbohydrate-high glycaemic index; LC-LGI, low carbohydrate-low glycaemic index (also called low Glycaemic-load diet); MC-MGI, medium carbohydrate-medium glycaemic index. Data are presented as unstandardized regression coefficients (β) and 95% confidence intervals using linear mixed models comprised fixed effects including age, gender, BMI, and LCD weight loss, as well as random effects for subjects and sites. Number of observations (n="FPG<5.6 mmol/L/FPG≥5.6-6.9 mmol/L") on the figure is completers. No difference in weight regain could be predicted using FPG on the HC-LGI, LC-HGI or MC-MGI diets (the three remaining diets from DiOGenes being intermediate in glycaemic load which is not presented in the main paper) (P≥0.63).

As part of the larger dietary weight maintenance trial DiOGenes, a total of 316 overweight and obese participants (Table 2), following successful loss of ≥8% body mass during an 8-week low-calorie weight-loss phase, were randomly assigned to an ad libitum low glycaemic-load (low carbohydrate and low glycaemic index) or high glycaemic-load (high carbohydrate and high glycaemic index) weight maintenance diet for 26 weeks (three other dietary regimens of the study are described in FIG. 7). Dietary fat content was held constant (~30 Energy %) between the two diets. Before the initial weight loss phase blood samples were drawn fasted from where FPG and FI were analysed. Furthermore, study participants completed weighed food diaries for three consecutive days at the end of the intervention. Height and weight were measured before the initial weight loss phase. During the weight maintenance period body weight was measured at randomization and week 2, 4, 6, 10, 14, 18, 22, and 26.

TABLE 2

Baseline characteristics of the study populations stratified by fasting plasma glucose

|  | FPG <5.6 mmol/L | FPG ≥5.6-6.9 mmol/L | FPG ≥7.0 mmol/L |
|---|---|---|---|
| DiOGenes | (n = 225) | (n = 41) |  |
| Age | 41.0 ± 6.1$^a$ | 43.3 ± 7.0$^b$ |  |
| Gender (% female/male) | 65.3/34.7 | 65.9/34.2 |  |
| Body weight (kg) | 96.6 (87.7; 109.3) | 98.9 (88.7; 115.6) |  |
| Weight loss during 8-week LCD (kg) | 10.3 (8.7; 12.4) | 10.3 (8.2; 12.8) |  |
| BMI (kg/m$^2$) | 33.1 (30.7; 36.8)$^a$ | 35.3 (32.0; 40.9)$^b$ |  |
| BMI category (% normal/overweight/obese) | 0.0/20.4/79.6 | 0.0/9.8/90.2 |  |
| Fasting glucose (mmol/L) | 4.9 (4.6; 5.2)$^a$ | 5.9 (5.7; 6.2)$^b$ |  |
| Fasting insulin (pmol/L) | 60 (42; 90)$^a$ | 89 (62; 108)$^b$ |  |
| SHOPUS | (n = 139) | (n = 37) |  |
| Age | 37.2 (29.2; 49.8)$^a$ | 51.5 (44.9; 57.8)$^b$ |  |
| Gender (% female/male) | 74.1/25.9$^a$ | 54.1/46.0$^b$ |  |
| Body weight (kg) | 85.0 (75.3; 100.6)$^a$ | 94.9 (86.8; 101.6)$^b$ |  |
| BMI (kg/m$^2$) | 28.9 (26.4; 31.9) | 30.7 (28.9; 33.9) |  |
| BMI category (% normal/overweight/obese) | 13.0/45.3/41.7 | 5.4/32.4/62.2 |  |
| Fasting glucose (mmol/L) | 5.1 (4.8; 5.3)$^a$ | 5.8 (5.6; 6.0)$^b$ |  |
| Fasting insulin (pmol/L) | 64 (41; 90) | 73 (46; 116) |  |
| NUGENOB | (n = 529) | (n = 197) | (n = 17) |
| Age | 36 (29; 42)$^a$ | 42 (36; 46)$^b$ | 41 (37; 47)$^b$ |
| Gender (% female/male)$^3$ | 83.7/16.3 | 53.8/46.2 | 52.9/47.1 |
| Body weight (kg) | 96.5 (88.1; 107.8)$^a$ | 103.0 (93.8; 111.0)$^b$ | 103.6 (92.6; 120.4)$^c$ |
| BMI (kg/m$^2$) | 34.6 (31.8; 38.0)$^a$ | 34.7 (31.9; 37.9)$^a$ | 34.9 (34.0; 40.4)$^b$ |
| BMI category (normal/overweight/obese) | 0.0/6.1/94.0 | 0.0/2.5/97.5 | 0.0/0.0/100 |
| Fasting glucose (mmol/L) | 5.1 (4.9; 5.3)$^a$ | 5.8 (5.7; 6.1)$^b$ | 7.4 (7.1; 9.2)$^c$ |
| Fasting insulin (pmol/L) | 57 (40; 81)$^a$ | 80 (60; 112)$^b$ | 122 (69; 176)$^c$ |

Abbreviations:
BMI, Body mass index;
FPG, Fasting plasma glucose;
LCD, low calorie diet.
Different alphabets within a row (a, b, c) indicate significant differences (P < 0.05).
$^3$Overall difference between groups tested by chi-squared, P < 0.001

In the SHOPUS study a total of 181 participants (Table 2) with increased waist circumference were randomly assigned to receive an ad libitum New Nordic Diet (NND) or a control diet for 26 weeks. The macronutrient composition of the NND was based on Nordic Nutrition Recommendations (13), but with slightly higher protein content, whereas the control diet was designed to match the macronutrient composition of the average consumed diet in Denmark (14) meaning a slightly higher fat content. The NND is a whole food approach characterized by being very high in dietary fibre, wholegrain, fruit, berries, and vegetables (11). Glycaemic index of the diets was not assessed. For both groups, food and beverages were provided from a study shop free of charge throughout the intervention period (11). Fasting blood samples were drawn at screening and baseline, respectively, from where FPG and FI were analysed. Height was measured at baseline and body weight was measured at randomization and week 2, 4, 8, 12, 16, 20, 24, and 26.

In the NUGENOB study a total of 771 primarily obese participants (Table 2) were randomly assigned to receive a low-fat/high-carbohydrate or high-fat/low-carbohydrate hypocaloric diet (−600 kcal/day) for 10 weeks. Dietary protein content was held constant (aiming at 15 Energy % and achieved ~17 Energy %) between the two diets. Glycaemic index of the diets was not assessed. Blood samples were drawn at baseline from where FPG and FI were analysed. Dietary intake during the intervention was calculated from six days of weighed food records during the intervention. Height was measured at baseline and body weight was measured weekly throughout the intervention.

Using the pre-treatment FPG participants were categorized as normo-glycaemic (FPG<5.6 mmol/L), prediabetic (FPG≥5.6-6.9 mmol/L), and diabetic (FPG≥7.0 mmol/L) using the FPG cut-offs by the American Diabetes Association (15). Only the NUGENOB trial included diabetic participants on both diets; hence, the DiOGenes and SHOPUS trial does not include analysis of diabetic participants. No similar categorization of individuals exists based on absolute values of FI. Previous studies have categorized differently and have not included intermediate values (4, 5). However, previous studies using measures of insulin secretion have used median split (6-8). We used the median value among the prediabetic participants as cut-offs (in each of the three studies separately) to categorize participants into having low or high FI. Finally, the dichotomized categorization of FPG and FI was also combined into four groups of individuals. As the number of diabetic participants was low in the NUGENOB trial, we lowered the FPG cut-off to 6.4 mmol/L when combined with FI.

Statistics

Baseline characteristics of the three studies were summarized as mean±standard deviation (SD), median (interquartile range [IQR]), or as proportions. Differences in baseline characteristics between glycaemic groups were assessed using two-sample t-tests or one-way ANOVA (variables possibly transformed before analysis) or Pearson's chi-squared tests. Pearson correlations were carried out between FPG and FI, and between FPG and weight change.

TABLE 3

Dietary composition of the six diets

| | Study | | |
|---|---|---|---|
| | DiOGenes[1] | | SHOPUS[2] |
| | Diet | | |
| | High GL (n = 71) | Low GL (n = 100) | NND (n = 91) |
| Protein (Energy %) | 16.8 (14.3; 19.6) | 21.3 (18.4; 24.2) | 17.9 (17.2; 18.6) |
| Carbohydrate (Energy %) | 50.8 (42.3; 57.6)[4] | 45.5 (40.0; 51.0)[4] | 54.3 (52.7; 56.0)[6] |
| Added sugar (Energy %) | 16.9 (13.0; 21.7)[5] | 16.5 (11.9; 20.1)[5] | 5.3 (4.0; 6.5) |
| Starch (Energy %) | 26.9 (18.6; 34.8) | 21.7 (16.2; 26.9) | |
| Fibre (Energy %) | 2.3 (1.8; 2.8) | 2.2 (1.6; 2.8) | 3.5 (3.3; 3.7) |
| Total fat (Energy %) | 30.3 (24.6; 36.5) | 30.3 (26.0; 38.1) | 30.0 (28.7; 31.1) |
| SFA (Energy %) | 9.9 (7.6; 12.8) | 9.7 (7.5; 11.9) | 7.8 (7.0; 8.6) |
| MUFA (Energy %) | 8.8 (6.0; 10.8) | 8.1 (6.4; 11.7) | 12.0 (11.0; 12.5) |
| PUFA (Energy %) | 5.5 (4.4; 9.9) | 5.5 (3.6; 9.0) | 7.8 (6.7; 8.7) |
| Alcohol (Energy %) | 0.0 (0.0; 2.0) | 0.0 (0.0; 1.9) | 1.1 (0.5; 2.4) |
| Dietary fibre (g/10 MJ) | 28 (22; 35) | 28 (20; 36) | 44 (41; 46) |
| Wholegrain (g/10 MJ) | | | 157 (138; 175) |
| Fruit (g/10 MJ) | 222 (49; 442) | 170 (73; 353) | 408 (356; 447) |
| Berries (g/10 MJ) | | | 87 (74; 101) |
| Vegetable (g/10 MJ) | 255 (140; 416) | 311 (176; 561) | 755 (662; 845) |
| Potato (g/10 MJ) | 77 (0; 159) | 30 (0; 78) | 118 (104; 143) |
| Milk products (g/10 MJ) | 231 (127; 412) | 377 (191; 668) | 338 (263; 429) |
| Meat and fish (g/10 MJ) | 167 (112; 233) | 259 (188; 370) | 199 (177; 219) |
| Nuts (g/10 MJ) | 0 (0; 0) | 0 (0; 0) | 35 (31; 39) |

TABLE 3-continued

Dietary composition of the six diets

| | | | |
|---|---|---|---|
| Salt (g/10 MJ) | 3.2 (2.7; 4.4) | 3.2 (2.4; 4.2) | 3.1 (2.8; 3.7) |
| Energy density (kJ/g) | | | 4.7 (4.5; 5.0) |
| Glycaemic index | 60.5 (57.1; 65.3) | 55.9 (52.4; 59.5) | |
| Glycaemic load (g/10 MJ) | 181 (154; 209) | 151 (134; 164) | |

| | Study | | |
|---|---|---|---|
| | SHOPUS[2] | NUGENOB[3] | |
| | | Diet | |
| | Control diet (n = 54) | High fat (n = 347) | Low fat (n = 366) |
| Protein (Energy %) | 16.5 (15.7; 17.3) | 16.9 (15.5; 18.5) | 17.6 (16.2; 19.6) |
| Carbohydrate (Energy %) | 50.8 (48.7; 52.1)[6] | 42.0 (38.8; 45.8)[4] | 57.3 (53.7; 60.8)[4] |
| Added sugar (Energy %) | 11.8 (10.3; 13.1) | | |
| Starch (Energy %) | | | |
| Fibre (Energy %) | 2.3 (2.1; 2.4) | 2.3 (1.8; 2.8) | 2.8 (2.3; 3.4) |
| Total fat (Energy %) | 33.9 (32.8; 35.1) | 40.4 (37.1; 43.6) | 24.6 (22.1; 27.4) |
| SFA (Energy %) | 13.2 (12.6; 13.9) | 12.9 (10.6; 15.8) | 7.6 (6.2; 9.1) |
| MUFA (Energy %) | 12.6 (12.2; 13.7) | 14.6 (12.9; 17.5) | 8.1 (6.4; 10.3) |
| PUFA (Energy %) | 5.1 (4.7; 5.7) | 7.0 (5.2; 9.2) | 4.2 (3.4; 5.5) |
| Alcohol (Energy %) | 1.3 (0.5; 2.2) | 0.0 (0.0; 0.0) | 0.0 (0.0; 0.0) |
| Dietary fibre (g/10 MJ) | 28 (26; 30) | 19 (15; 23) | 22 (18; 27) |
| Wholegrain (g/10 MJ) | 43 (38; 51) | | |
| Fruit (g/10 MJ) | 190 (173; 215) | | |
| Berries (g/10 MJ) | 6 (4; 8) | | |
| Vegetable (g/10 MJ) | 239 (210; 262) | | |
| Potato (g/10 MJ) | 79 (54; 97) | | |
| Milk products (g/10 MJ) | 379 (335; 468) | | |
| Meat and fish (g/10 MJ) | 181 (162; 204) | | |
| Nuts (g/10 MJ) | 8 (6; 10) | | |
| Salt (g/10 MJ) | 3.5 (2.9; 4.1) | | |
| Energy density (kJ/g) | 5.8 (5.3; 6.1) | | |
| Glycaemic index | | | |
| Glycaemic load (g/10 MJ) | | | |

Abbreviations: MUFA, Mono unsaturated fatty acids; NND, New Nordic diet; PUFA, Poly unsaturated fatty acids; SFA, Saturated fatty acids; FPG, Fasting plasma glucose.
[1]Median (IQR) intake from a 3-day weighed food record by the end of the 26 week intervention period.
[2]Median (IQR) intake during the 26 week intervention period. Intake was calculated as foods collected in the shop subtracted by the foods not consumed plus consumption of foods from elsewhere.
[3]Median (IQR) intake from weighted food records during the intervention (1-day weighted food record at week 2, 5 and 7 and a 3-day weighed food record at week 10).
[4]Total carbohydrates (including fibre). Energy % of available carbohydrates is unknown.
[5]Total sugars
[6]Available carbohydrates (not including fibre) were 47.1 (45.1; 48.7) and 45.8 (44.2; 47.2) Energy %, respectively.

In each of the three studies separately, the differences in weight change between glycaemic and insulinemic groups (and the combination of the two) were analysed by means of linear mixed models using all available weight measurements (also from non-completers). The linear mixed models included the diet x time x glycaemic and/or insulinemic strata and comprised fixed effects including age, gender, BMI, and initial weight loss (for DiOGenes only), as well as random effects for subjects and sites (not for SHOPUS). Results are shown as mean weight change with 95% confidence interval (CI). For each study, differences in weight change between diets were compared within and between each blood marker group through pairwise comparisons using post hoc t-tests. The level of significance was set at P<0.05 with no adjustments for the number of tests done and statistical analyses were conducted using STATA/SE 14.1 (Houston, USA).

Results

In all three trials individuals with prediabetes were older and had a higher baseline body weight and/or BMI compared to the normo-glycaemic individuals (P<0.05) (Table 2). Description of the dietary intake can be found in Table 3. The correlations between FPG and FI in the three trials were low but significant ($r^2$=0.04 to 0.08; P≤0.005).

Figure 4:
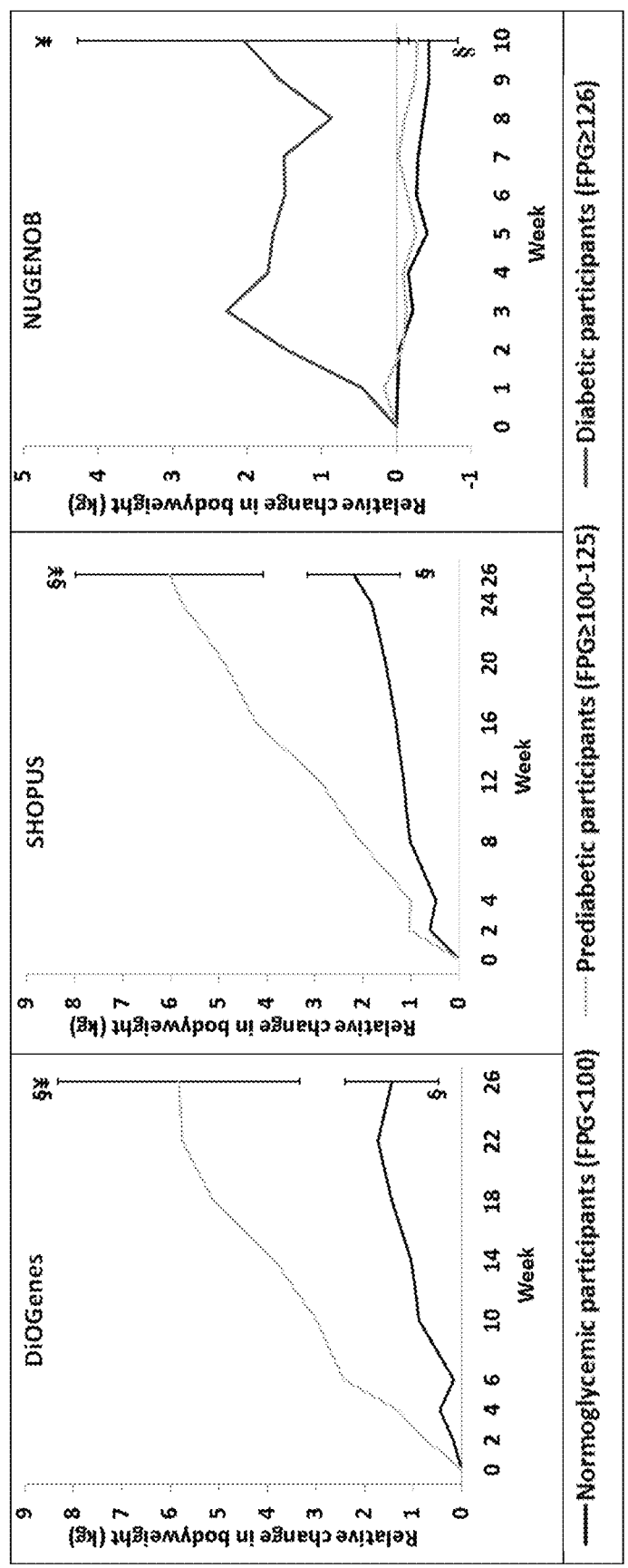
FIG. 4 shows the relative change in body weight between diets within each of the three studies when stratified on pre-treatment fasting plasma glucose. Abbreviations: FPG, Fasting plasma glucose (unit: mmol/L). Data are presented as estimated mean weight change from baseline and 95% confidence intervals for each combination of the diet-time-FPG strata interaction in the linear mixed models, which were additionally adjusted for age, gender, BMI, and LCD weight loss (for DiOGenes only), subjects, and sites (not for SHOPUS). The zero line indicates no difference between diets. Above the zero line favours the low glycaemic-load diet (DiOGenes), the New Nordic Diet (SHOPUS), and the high-fat/low-carbohydrate diet (NUGENOB). The confidence interval for prediabetic participants in the NUGENOB trial was omitted from the figure. ¥ indicate significant difference between the glycaemic groups (P<0.05). § indicate significant difference from zero (P<0.05).

After a median weight loss of 10.3 kg in the DiOGenes study, prediabetic participants regained 5.83 (95% CI, 3.34, 8.32; P<0.001) kg more on the 26 week ad libitum high than low glycaemic-load diet, whereas normo-glycaemic participants regained only 1.44 (95% CI, 0.48, 2.41; P=0.003) kg more (FIG. 4 & Table 4).

TABLE 4

Change in body weight on different diets when stratified on pre-treatment fasting plasma glucose

DiOGenes study

| | Cut-off | | | |
|---|---|---|---|---|
| | FPG < 5.6 mmol/L | | FPG ≥ 5.6-6.9 mmol/L | |
| Diets | Low GL diet (n = 91) | High GL diet (n = 88) | Low GL diet (n = 23) | High GL diet (n = 7) |
| ΔWeight (kg) | 0.28 (−0.41; 0.98)$^a$ | 1.73 (1.15; 2.40)$^b$ | −1.34 (−2.63; −0.05)$^c$ | 4.49 (2.35; 6.63)$^d$ |

SHOPUS study

| | Cut-off | | | |
|---|---|---|---|---|
| | FPG < 5.6 mmol/L | | FPG ≥ 5.6-6.9 mmol/L | |
| Diets | NND (n = 70) | Control diet (n = 44) | NND (n = 21) | Control diet (n = 10) |
| ΔWeight (kg) | −3.91 (−4.53; −3.29)$^a$ | −1.71 (−2.49; −0.94)$^b$ | −6.80 (−7.97; −5.63)$^c$ | −0.77 (−2.41; 0.87)$^b$ |

NUGENOB study

| | Cut-off | | | | | |
|---|---|---|---|---|---|---|
| | FPG < 5.6 mmol/L | | FPG ≥ 5.6-6.9 mmol/L | | FPG ≥ 7.0 mmol/L | |
| Diets | High fat (n = 205) | Low fat (n = 255) | High fat (n = 97) | Low fat (n = 71) | High fat (n = 7) | Low fat (n = 8) |
| ΔWeight (kg) | −6.45 (−6.91; −5.99)$^a$ | −6.88 (−7.33; −6.44)$^b$ | −6.54 (−7.10; −5.98)$^{ab}$ | −6.82 (−7.45; −6.20)$^b$ | −6.50 (−8.21; −4.78)$^{abc}$ | −4.45 (−5.97; −2.93)$^c$ |

Abbreviations: ADA, American Diabetes Association; FPG, Fasting plasma glucose.
Data are presented as unstandardized regression coefficients (β) and 95% confidence intervals using linear mixed models comprised fixed effects including age, gender, BMI, and LCD weight loss (for DiOGenes only), as well as random effects for subjects and sites (not for SHOPUS).
Number of observations (n) is completers.
Different alphabets within a row (a, b, c, d) indicate significant differences (P < 0.05).

Figure 5:
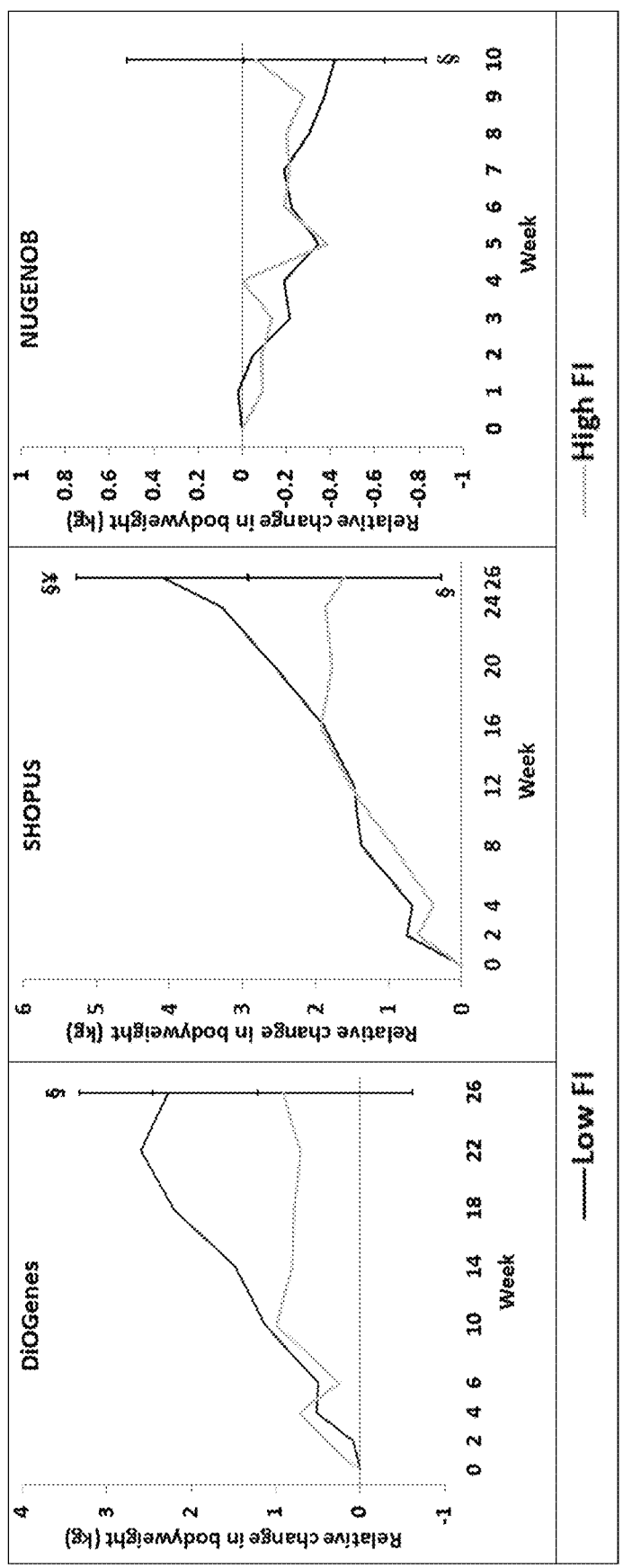
FIG. 5 shows the relative change in body weight between diets within each of the three studies when stratified on pre-treatment fasting insulin. Abbreviations: FI, Fasting insulin. Data are presented as estimated mean weight change from baseline and 95% confidence intervals for each combination of the diet-time-FI strata interaction in the linear mixed models, which were additionally adjusted for age, gender, BMI, and LCD weight loss (for DiOGenes only), subjects, and sites (not for SHOPUS). The zero line indicates no difference between diets. Above the zero line favours the low glycaemic-load diet (DiOGenes), the New Nordic Diet (SHOPUS), and the high-fat/low-carbohydrate diet (NUGENOB). Cut-offs were 90.3 pmol/L (DiOGenes), 72.9 pmol/L (SHOPUS), and 79.2 pmol/L (NUGENOB), representing the median FI of prediabetic participants within each study. ¥ indicate significant difference between the insulinemic groups (P<0.05). § indicate significant difference from zero (P<0.05).

Consequently, a 4.39 kg (95% CI, 1.76, 7.02; P=0.001) difference in responsiveness to the diets were found between normo-glycaemic and prediabetic participants. Participants with low FI regained 2.27 (95% CI, 1.22, 3.32; P<0.001) kg more on the high than low glycaemic-load diet, whereas no difference was observed for participants with high FI (P=0.24). Consequently, no difference in responsiveness to the diets were found between participants with high and low FI (P=0.14) (FIG. 5 & Table 5).

SUPPLEMENTAL TABLE 5

Change in body weight on different diets when stratified on pre-treatment insulinemic status

DiOGenes study

| Cut-off | FI <90.3 pmol/L | | FI >90.3 pmol/L | |
|---|---|---|---|---|
| Diets | Low GL diet (n = 86) | High GL diet (n = 70) | Low GL diet (n = 32) | High GL diet (n = 22) |
| ΔWeight (kg) | −0.64 (−1.37; 0.08)$^a$ | 1.63 (0.86; 2.40)$^b$ | 0.60 (−0.43; 1.63)$^b$ | 1.52 (0.37; 2.67)$^b$ |

SHOPUS study

| Cut-off | FI <72.9 pmol/L | | FI >72.9 pmol/L | |
|---|---|---|---|---|
| Diets | NND (n = 51) | Control diet (n = 31) | NND (n = 40) | Control diet (n = 23) |
| ΔWeight (kg) | −5.30 (−6.03; −4.57)$^a$ | −1.21 (−2.17; −0.25)$^b$ | −3.63 (−4.47; −2.79)$^c$ | −2.01 (−3.08; −0.95)$^b$ |

SUPPLEMENTAL TABLE 5-continued

Change in body weight on different diets when stratified on pre-treatment insulinemic status

| | NUGENOB study | | | |
|---|---|---|---|---|
| Cut-off | FI <79.2 pmol/L | | FI >79.2 pmol/L | |
| Diets | High fat diet (n = 198) | Low fat diet (n = 230) | High fat diet (n = 111) | Low fat diet (n = 102) |
| ΔWeight (kg) | −6.63 (−7.11; −6.15)$^a$ | −7.05 (−7.51; −6.58)$^b$ | −6.20 (−6.75; −5.65)$^a$ | −6.26 (−6.83; −5.69)$^a$ |

Abbreviations:
FI, Fasting insulin.
Data are presented as unstandardized regression coefficients (β) and 95% confidence intervals using linear mixed models comprised fixed effects including age, gender, BMI, and LCD weight loss (for DiOGenes only), as well as random effects for subjects and sites (not for SHOPUS).
Number of observations (n) is completers.
Different alphabets within a row (a, b, c) indicate significant differences (P < 0.05).
Cut-offs for FI represented the median FI of prediabetic participants within each study.

Figure 6:
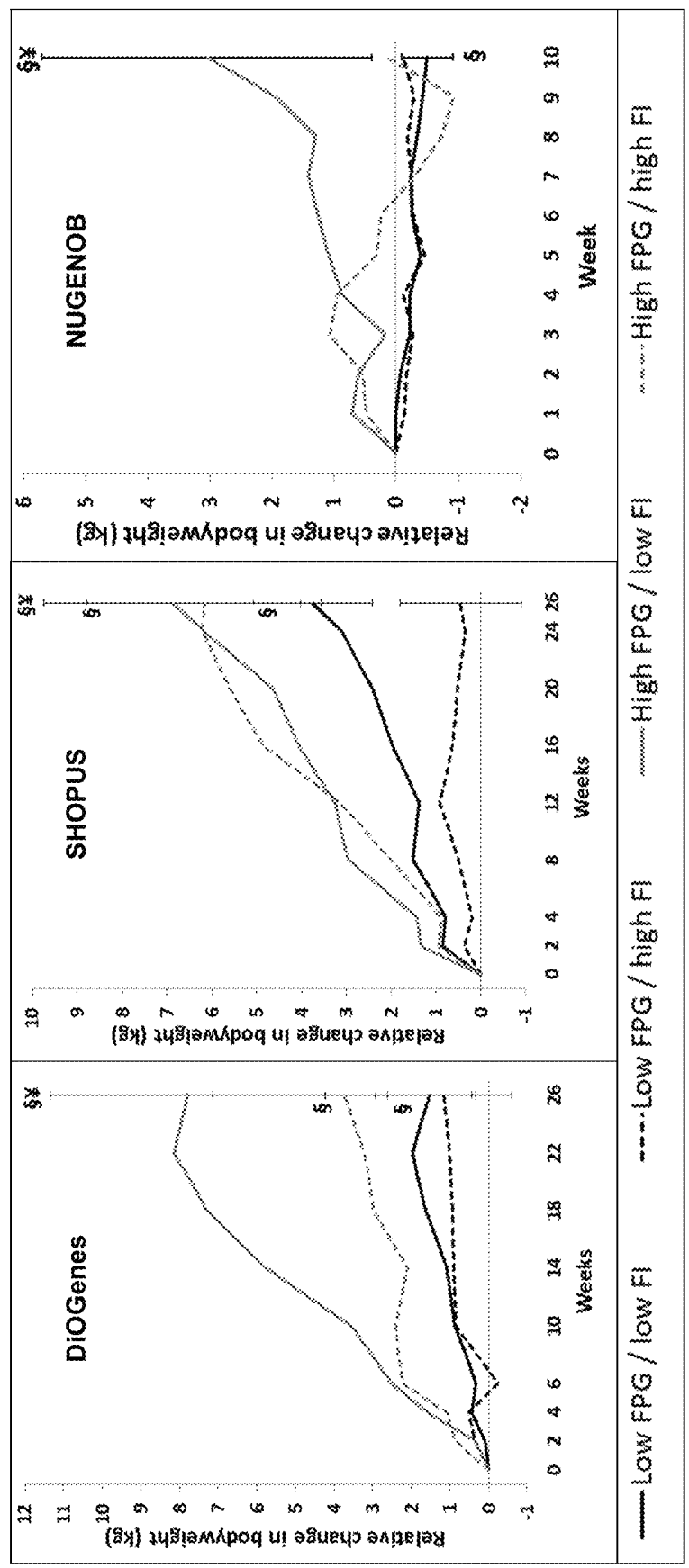
FIG. 6 shows the relative change in body weight between diets within each of the three studies when stratified on pre-treatment fasting plasma glucose and insulin. Abbreviations: FI, Fasting insulin; FPG, Fasting plasma glucose. Data are presented as estimated mean weight change from baseline and 95% confidence intervals for each combination of the diet-time-FPG-FI strata interaction in the linear mixed models, which were additionally adjusted for age, gender, BMI, and LCD weight loss (for DiOGenes only), subjects, and sites (not for SHOPUS). The zero line indicates no difference between diets. Above the zero line favours the low glycaemic-load diet (DiOGenes), the New Nordic Diet (SHOPUS), and the high-fat/low-carbohydrate diet (NUGENOB). Confidence interval for the high FI groups in the NUGENOB trial was omitted from the figure. Cut-offs for FPG and FI were 5.6 mmol/L and 90.3 pmol/L (DiOGenes), 5.6 mmol/L and 72.9 pmol/L (SHOPUS), and 6.4 mmol/L and 79.2 pmol/L (NUGENOB). ¥ indicate significant difference between the glycaemic/insulinemic groups (P<0.05). § indicate significant difference from zero (P<0.05).

Prediabetes participants with low FI regained 7.78 kg (95% CI, 4.39, 11.18; P<0.001) more on the high than low glycaemic-load diet, whereas no difference was observed for normo-glycaemic participants with high FI [1.17 kg (95% CI, −0.59, 2.93; P=0.19)] (FIG. 6 & Table 6). The correlation between FPG and weight gain during the intervention was −0.14 (P=0.14) on the low glycaemic-load diet and 0.22 (P=0.028) on the high glycaemic-load diet.

TABLE 6

Change in body weight on different diets when stratified on pre-treatment fasting plasma glucose and insulin

| | DiOGenes study | | | |
|---|---|---|---|---|
| Cut-offs | FPG <5.6 & FI <90.3 | FPG ≥5.6-6.9 & FI <90.3 | FPG <5.6 & FT >90.3 | FPG ≥5.6-6.9 & FT >90.3 |
| | Low Glycaemic-load diet | | | |
| | (n = 69) | (n = 12) | (n = 22) | (n = 11) |
| ΔWeight (kg) | 0.13 (−0.65; 0.90)$^a$ | −3.12 (−4.87; −1.38)$^b$ | 0.75 (−0.54; 2.03)$^a$ | 0.56 (−1.25; 2.37)$^a$ |
| | High Glycaemic-load diet | | | |
| | (n = 65) | (n = 4) | (n = 23) | (n = 3) |
| ΔWeight (kg) | 1.66 (0.89; 2.42)$^a$ | 4.66 (1.75; 7.58)$^b$ | 1.92 (0.70; 3.13)$^{ab}$ | 4.29 (1.21; 7.37)$^{ab}$ |
| | SHOPUS study | | | |
| Cut-offs | FPG <5.6 & FI <72.9 | FPG ≥5.6-6.9 & FI <72.9 | FPG <5.6 & FT >72.9 | FPG ≥5.6-6.9 & FT >72.9 |
| | New Nordic Diet | | | |
| | (n = 42) | (n = 9) | (n = 28) | (n = 12) |
| ΔWeight (kg) | −4.69 (−5.47; −3.91)$^a$ | −8.04 (−9.68; −6.39)$^b$ | −2.75 (−3.71; −1.79)$^c$ | −5.83 (−7.36; −4.30)$^a$ |
| | Control diet | | | |
| | (n = 26) | (n = 5) | (n = 18) | (n = 5) |
| ΔWeight (kg) | −1.04 (−2.07; −0.01)$^{ab}$ | −1.77 (−3.99; 0.45)$^{ab}$ | −2.65 (−3.81; −1.49)$^a$ | 0.32 (−1.92; 2.56)$^b$ |
| | NUGENOB study | | | |
| Cut-offs[3] | FPG <6.4 & FI <79.2 | FPG ≥6.4 & FT <79.2 | FPG <6.4 & FT >79.2 | FPG ≥6.4 & FT >79.2 |

TABLE 6-continued

Change in body weight on different diets when stratified on pre-treatment fasting plasma glucose and insulin

| | Low fat diet | | | |
|---|---|---|---|---|
| | (n = 223) | (n = 7) | (n = 93) | (n = 9) |
| ΔWeight (kg) | −7.06 (−7.52; −6.60)$^a$ | −6.78 (−8.50; −5.07)$^{ab}$ | −6.27 (−6.85; −5.69)$^b$ | −6.25 (−7.69; −4.82)$^{ab}$ |

| | High fat diet | | | |
|---|---|---|---|---|
| | n = 194) | (n = 4) | (n = 92) | (n = 19) |
| ΔWeight (kg) | −6.56 (−7.04; −6.09)$^a$ | −9.84 (−11.93; −7.75)$^b$ | −6.15 (−6.72; −5.58)$^a$ | −6.41 (−7.49; −5.33)$^a$ |

Abbreviations:
FI, Fasting insulin (unit: pmol/L);
FPG, Fasting plasma glucose (unit: mmol/L).
Data are presented as unstandardized regression coefficients (β) and 95% confidence intervals using linear mixed models comprised fixed effects including age, gender, BMI, and LCD weight loss (for DiOGenes only), as well as random effects for subjects and sites (not for SHOPUS).
Number of observations (n) is completers.
Different alphabets within a row (a, b, c) indicate significant differences (P < 0.05).
Cut-offs for FI represented the median FI of prediabetic participants within each study.

In the SHOPUS study prediabetic participants lost 6.04 (95% CI 4.05, 8.02; P<0.001) kg more on the 26 week ad libitum NND than the control diet, whereas normo-glycaemic participants lost only 2.20 (95% CI 1.21, 3.18; P<0.001) kg more. Consequently, a 3.84 kg (95% CI, 1.62, 6.06; P=0.001) difference in responsiveness to the diets were found between normo-glycaemic and prediabetic participants (FIG. 4 & Table 4). Participants with low FI lost 4.09 (95% CI 2.91, 5.27; P<0.001) kg more on NND than the control diet, whereas participants with high FI lost only 1.61 (95% CI 0.28, 2.94; P=0.02) kg more. Consequently, a 2.48 kg (95% CI, 0.70, 4.26; P=0.006) kg difference in responsiveness to the diets were found between participants with high and low FI (FIG. 5 & Table 5). Prediabetic participants with low FI lost 6.27 kg (95% CI, 3.51, 9.02; P<0.001) more on the NND than the control diet, whereas no difference was observed for normo-glycaemic participants with high FI [0.10 kg (95% CI, −1.37, 1.57; P=0.89)] (FIG. 6 & Table 6). The correlation between FPG and weight gain was −0.29 (P=0.005) on the NND and 0.01 (P=0.92) on the control diet.

In the NUGENOB study normo-glycaemic participants lost 0.43 (95% CI, 0.03, 0.83; P=0.03) kg more on the 10 week hypocaloric low-fat/high-carbohydrate than high-fat/low-carbohydrate diet, whereas no difference was observed for prediabetic participants (P=0.41) and diabetic participants tended to lose 2.04 (95% CI, −0.20, 4.28; P=0.07) more on the high-fat/low-carbohydrate diet. Consequently, a 2.47 kg (95% CI, 0.20, 4.75; P=0.03) difference in responsiveness to the diets were found between normo-glycaemic and diabetic participants (FIG. 4 & Table 4). Participants with low FI lost 0.42 (95% CI, 0.01, 0.83; P=0.046) kg more on the low-fat/high-carbohydrate than high-fat/low carbohydrate diet, whereas no difference was observed for participants with high FI (P=0.84). Consequently, no difference in responsiveness to the diets were found between participants with high and low FI (P=0.33) (FIG. 5 & Table 5). Participants with FPG≥6.4 mmol/L and low FI lost 3.06 kg (95% CI, 0.40, 5.71; P=0.02) more on the high-fat/low carbohydrate than the low-fat/high-carbohydrate diet. Participants with FPG<6.4 mmol/L and low FI lost 0.49 kg (95% CI, 0.08, 0.91; P=0.02) kg more on the low-fat/high-carbohydrate diet (FIG. 6 & Table 6). The correlation between FPG and weight gain was 0.06 (P=0.30) on the low-fat/high-carbohydrate diet and −0.03 (P=0.55) on the high-fat/low carbohydrate diet.

DISCUSSION

We identified fasting plasma glucose as an important biomarker that is associated with dietary weight loss and weight loss maintenance success on a range of different hypocaloric and ad libitum diets. Thus, overweight and obese participants with elevated fasting blood glucose, i.e. prediabetic individuals, are extremely susceptible to weight gain (re-gain) on a high glycaemic load diet, but can, on the other hand achieve substantial weight loss on a diet with a reduced glycaemic load, or a diet high in fibre and wholegrain even without prescribing calorie restriction per se.

We have previously reported in the Diogenes trial a relative modest difference in weight regain of 2.0 kg between the high and low glycaemic load diets after 26 weeks of weight maintenance (9). However, we now report that this difference in weight maintenance between the diets was more than four times larger in prediabetic than in normo-glycaemic participants (5.8 vs. 1.4 kg). Likewise, we have previously reported the overall difference between the NND and control diet to be 3.2 kg (11). This difference was almost three times larger in prediabetic than in normo-glycaemic participants (6.0 vs 2.2 kg). Furthermore, we have previously reported a non-significant difference of 0.3 kg between a 10-week hypocaloric (−600 kcal/day) low-fat/high-carbohydrate and high-fat/low-carbohydrate diet (12). Stratifying on FPG revealed a difference in response between the two diets of 2.5 kg between normo-glycaemic and diabetic participants resulting in a small but significantly larger weight loss among normo-glycaemic participants on the low-fat/high-carbohydrate diet and borderline larger weight loss among diabetic participants on the high-fat/low-carbohydrate diet.

Pre-treatment FI was a modest biomarker on its own; however, adding FI as a biomarker in combination with FPG further strengthened the associations and revealed interesting phenotypes. Participants with low FPG and high FI responded equally on all three pair of diets, whereas participants with high FPG and low FI did better on diets lower in glycaemic-load and higher in fibre/wholegrain. Furthermore, individuals with low FPG and low FI did better on a caloric restricted low-fat/high-carbohydrate diet.

The dietary interventions were carefully controlled to avoid undesirable differences in the dietary composition within each of the studies. This resulted in a fat energy percent within the targeted interval in the NUGENOB trial (12) and a diet fully in accordance with the NND principles in the SHOPUS trial (11). However, glycaemic index was not registered in the SHOPUS and NUGENOB trials and we cannot rule out that differences in glycaemic load could be partly responsible for the differences observed in weight change in the present analyses. However, the large difference in the carbohydrate content of the diets in NUGENOB could be used as a proxy of glycaemic load. The targeted differences of 12 Energy % protein (at the expense of carbohydrates) and 15 glycaemic-index units in DiOGenes were not fully achieved and were instead 5.4 Energy % and 4.7 glycaemic-index units, respectively (9). Nevertheless, the obtained differences in dietary intake were large enough to detect differences in weight management when stratifying on glycaemic status.

While it appears that FPG is responsible for the different effects of the diets it is also possible that FPG is a marker for something else that we did not measure. However, without being limited to any theory, mechanistic explanation for a direct role of FPG is plausible as an increased FPG reflects insulin resistance that is not overcome by enhanced insulin secretion. To act as a satiety signal, glucose needs to be taken up by cells in liver, muscle, adipose tissue and the brain, tissues that are supposed to deliver feed-back to the brain centres that control appetite and energy intake. We hypothesize that elevated FPG concentrations reflect that less glucose is taken up by the cells due to the impaired glucose metabolism, and that, in part, can be responsible for a weaker satiating effect of carbohydrates in prediabetic individuals as contrasted to the insulin sensitive normo-glycaemic obese individuals. However, no matter the mechanisms, FPG may serve as a unique and easily accessible biomarker that could be used to predict future weight loss success on different diets.

Over the past several decades, numerous randomized controlled trials have compared various diets for the treatment of obesity based on the assumption that one diet fits all without being able to provide strong evidence for one or the other (2, 3, 9, 11, 12). From our results it appears that failure to stratify on glycaemic status is likely to underestimate (9, 11) or overlook (12) specific effects among prediabetic and diabetic individuals, whereas it may mask (12) or overestimate (9, 11) the effects of a specific diet among the normo-glycaemic individuals. Therefore, we strongly encourage investigation of FPG as a modifier of weight loss/maintenance in other large dietary clinical trials to help find the most appropriate diet for individuals with differing glycaemic status.

Generating evidence to support precision medicine is challenging but interaction testing in randomized clinical trials of intervention effectiveness provides potential efficient means especially when replicated in more studies (15). We used the most widely accepted FPG cut-offs advised by the American Diabetes Association to present the most transparent results (16). When stratifying on FPG the randomized study designs that should balance out known and unknown confounders are weakened, and we therefore adjusted for age, sex and initial BMI as these differed or tended to differ between the glycaemic groups. A weakness is that the three studies were not designed to examine for differences in responsiveness between normo-glycaemic and prediabetic obese individuals, and it is a matter of chance that we had enough in each group to provide statistical power for analyses. However, the post-hoc approach can also be looked upon as strength as all three studies were double-blinded with respect to the glycaemic status of the participants, and the identified difference in dietary responsiveness cannot have been influenced by knowledge of the participants or investigators. Moreover, although some of the analyses, especially those for diabetic individuals, are based on relatively small numbers our findings seem to be quite consistent across three different studies, which suggest robustness of the findings.

In conclusion, elevated pre-treatment FPG predicts success in dietary weight loss and maintenance of weight loss among overweight patients on hypocaloric and ad libitum diets low in glycaemic-load or with high fibre and wholegrain. This easily accessible biomarker could potentially help stratifying patients in personalize dietary guidance for overweight and obesity in order to magnify weight loss and optimize weight maintenance.

REFERENCES

1. Freedhoff Y, Hall K D. Weight loss diet studies: we need help not hype. The Lancet. 2016; 388(10047):849-51.
2. Sacks F M, Bray G A, Carey V J, Smith S R, Ryan D H, Anton S D, McManus K, Champagne C M, Bishop L M, Laranjo N et al. Comparison of weight-loss diets with different compositions of fat, protein, and carbohydrates. N Engl J Med. 2009; 360(9):859-73.
3. Foster G D, Wyatt H R, Hill J O, Makris A P, Rosenbaum D L, Brill C, Stein R I, Mohammed B S, Miller B, Rader D J et al. Weight and metabolic outcomes after 2 years on a low-carbohydrate versus low-fat diet: a randomized trial. Ann Intern Med. 2010; 153(3):147-57.
4. Cornier M, Donahoo W T, Pereira R, Gurevich I, Westergren R, Enerback S, Eckel P J, Goalstone M L, Hill J O, Eckel R H et al. Insulin sensitivity determines the effectiveness of dietary macronutrient composition on weight loss in obese women. Obes Res. 2005; 13(4):703-9.
5. McClain A D, Otten J J, Hekler E B, Gardner C D. Adherence to a low-fat vs. low-carbohydrate diet differs by insulin resistance status. Diabetes, Obesity and Metabolism. 2013; 15(1):87-90.
6. Gardner C D, Offringa L C, Hartle J C, Kapphahn K, Cherin R. Weight loss on low-fat vs. low-carbohydrate diets by insulin resistance status among overweight adults and adults with obesity: A randomized pilot trial. Obesity. 2016; 24(1):79-86.
7. Pittas A G, Das S K, Hajduk C L, Golden J, Saltzman E, Stark P C, Greenberg A S, Roberts S B. A low-glycaemic load diet facilitates greater weight loss in overweight adults with high insulin secretion but not in overweight adults with low insulin secretion in the CALERIE Trial. Diabetes Care. 2005 December; 28(12):2939-41.
8. Ebbeling C B, Leidig M M, Feldman H A, Lovesky M M, Ludwig D S. Effects of a low-glycaemic load vs low-fat diet in obese young adults: a randomized trial. JAMA. 2007; 297(19):2092-102.
9. Larsen T M, Dalskov S, van Baak M, Jebb S A, Papadaki A, Pfeiffer A F, Martinez J A, Handjieva-Darlenska T, Kunesova M, Pihlsgård M et al. Diets with high or low protein content and glycaemic index for weight-loss maintenance. N Engl J Med. 2010; 363(22):2102-13.
10. Larsen T M, Dalskov S, Van Baak M, Jebb S, Kafatos A, Pfeiffer A, Martinez J A, Handjieva-Darlenska T, Kunesova M, Holst C et al. The Diet, Obesity and Genes (Diogenes) Dietary Study in eight European countries—a comprehensive design for long-term intervention. Obesity reviews. 2010; 11(1):76-91.

11. Poulsen S K, Due A, Jordy A B, Kiens B, Stark K D, Stender S, Holst C, Astrup A, Larsen T M. Health effect of the New Nordic Diet in adults with increased waist circumference: a 6-mo randomized controlled trial. Am J Clin Nutr. 2014 January; 99(1):35-45.
12. Petersen M, Taylor M, Saris W, Verdich C, Toubro S, Macdonald I, Rossner S, Stich V, Guy-Grand B, Langin D et al. Randomized, multi-center trial of two hypo-energetic diets in obese subjects: high-versus low-fat content. Int J Obes. 2006; 30(3):552-60.
13. Nordic Council of Ministers. Nordic Nutrition Recommendations 2004: Integrating Nutrition and Physical Activity. Nordic Council of Ministers; 2005.
14. Pedersen A N, Fagt S, Groth M V, Christensen T, Biltoft-Jensen A P, Matthiessen J, Andersen N L, Kørup K, Hartkopp H B, Ygil K H et al. Danskernes kostvaner 2003-2008: hovedresultater. DTU Fødevareinstituttet; 2010.
15. Pletcher M J, McCulloch C E. The Challenges of Generating Evidence to Support Precision Medicine. JAMA Intern Med. 2017. doi:10.1001/jamainternmed.2016.9138.
16. American Diabetes Association. 2. Classification and Diagnosis of Diabetes. Diabetes Care. 2016 January; 39 Suppl 1:S13-22.

Example 2. Low GI/Low GL Diet and High GI/High GL Diet

The Diogenes database was used with the aim of finding an accurate measurement for classification of individuals as insulin resistant/sensitive.

The prediabetic obese subjects (FPG 100-125 mg/dl) were slightly older, consisted of relatively more males and had a slightly higher BMI compared to the non-diabetic obese subjects (FPG<100 mg/dl) (P≤0.016) (Table 1).

TABLE 7

Baseline characteristics of the overweight/obese study population stratified by glycemic status

|  | Non-diabetic subjects (n = 617) | Prediabetic subjects (n = 118) | P-value |
| --- | --- | --- | --- |
| Age | 41.1 6.2 | 43.3 6.2 | 0.001 |
| Gender (male/female) | 33%/67% | 45%/55% | 0.016 |
| Height (cm) | 170.4 ± 9.1 | 169.6 ± 10.3 | 0.44 |

TABLE 7-continued

Baseline characteristics of the overweight/obese study population stratified by glycemic status

|  | Non-diabetic subjects (n = 617) | Prediabetic subjects (n = 118) | P-value |
| --- | --- | --- | --- |
| Body weight (kg) | 99.5 ± 16.9 | 102.6 ± 19.5 | 0.069 |
| Fat-free mass (kg) | 58.5 (50.9; 70.6)[1] | 56.8 (50.0; 68.2)[2] | 0.16[3] |
| Fat-mass (kg) | 38.4 (32.1; 46.5)[1] | 39.7 (31.5; 49.4)[2] | 0.90[3] |
| BMI | 34.2 ± 4.7 | 35.5 ± 4.9 | 0.007 |

Data are presented as mean ± standard deviation, median (interquartile range) or proportions.
Differences were tested using a two-sample t-test or Pearson's chi squared Test.
[1]n = 532,
[2]n = 103,
[3]Log-transformed before analyses Subjects were classified as high FPG/low FPG (same as high/low FPG) before they started the low calorie diet (LCD). Weight loss during the 8-week low calorie diet was lower among prediabetics compared to non-diabetic obese subjects [−0.76 (−1.20; −0.31) kg; P=0.001] and fat loss tended to be lower [−0.98 (−2.00; 0.03) P=0.058]. FIG. 8 presents absolute weight loss during the LCD-period among these two groups.

During the subsequent 6 month ad libitum diet phase the high CHO-high GI diet (same as high GL/high GI diet) resulted in a greater weight regain [3.85 (1.37; 6.33) kg; (p=0.002)] among prediabetics compared to the non-diabetic subjects, whereas the weight regain was lower among prediabetics compared to non-diabetic subjects (−1.71 (−3.22; −0.21)] kg (p=0.026) for those randomized to the low CHO/low GI diet. No difference in weight regain was observed among the three other diets (P≤0.47).

Consequently, prediabetic subjects on the high CHO-high GI diet regained 6.95 (4.23; 9.68) kg more body weight (P<0.001) and 4.41 (−0.09; 8.74) kg (P=0.045) more fat mass than the prediabetics on the low CHO-low GI diet. The non-diabetic subjects allocated to the high CHO-high GI diet regained only 1.39 (0.40; 2.38) kg more body weight (P=0.006) than the non-diabetic subjects on the low CHO-low GI diet (FIG. 9). FIG. 9 also shows that prediabetic subjects lost ca. 2 kg during the 26 weeks low CHO-low GI diet. Furthermore, subjects with FPG between 100-125 g/dl and f-insulin <13 μIU/mL lost ca. 4 kg during the same time (Table 8) and subjects with FPG between 100-125 g/dl, f-insulin <13 μIU/mL and 30-minutes insulin >57.5 μIU/mL lost ca. 8 kg during the same 26 weeks.

TABLE 8

Weight loss after 26 weeks low CHO/low GI diet or high CHO/high GI diet based on subjects FPG, f-insulin and 30-minutes insulin.

| FPG | F-Insulin (below/above median) | Week no. | Weight | P-value | 95% CL (lower) | 95% CL (upper) |
| --- | --- | --- | --- | --- | --- | --- |
| Low CHO/low GI diet | | | | | | |
| FPG < 100 | F-Insulin < 13 | 26 | 0.37 | 0.372 | −0.443 | 1.184 |
| FPG < 100 | F-Insulin > 13 | 26 | 1.021 | 0.126 | −0.287 | 2.33 |
| FPG 100-125 | F-Insulin < 13 | 26 | −4.096 | 0 | −6.075 | −2.117 |
| FPG 100-125 | F-Insulin > 13 | 26 | −0.264 | 0.825 | −2.599 | 2.072 |
| High CHO/high GI diet | | | | | | |
| FPG < 100 | F-Insulin < 13 | 26 | 1.898 | 0 | 1.094 | 2.702 |
| FPG < 100 | F-Insulin > 13 | 26 | 1.786 | 0.01 | 0.428 | 3.144 |

TABLE 8-continued

Weight loss after 26 weeks low CHO/low GI diet or high CHO/high GI diet based on subjects FPG, f-insulin and 30-minutes insulin.

| FPG | F-Insulin | Week no. | Weight | P-value | 95% CL (lower) | 95% CL (upper) |
|---|---|---|---|---|---|---|
| FPG 100-125 | F-Insulin < 13 | 26 | 3.684 | 0.037 | 0.229 | 7.14 |
| FPG 100-125 | F-Insulin > 13 | 26 | 6.731 | 0.007 | 1.819 | 11.643 |

| FPG | Insulin-30 (below/above median) | Week no. | Weight | P-value | 95% CL (lower) | 95% CL (upper) |
|---|---|---|---|---|---|---|
| *Low CHO/low GI diet* | | | | | | |
| FPG < 100 | Insulin-30 < 57.5 | 26 | 1.045 | 0.023 | 0.145 | 1.945 |
| FPG < 100 | Insulin-30 > 57.5 | 26 | −0.803 | 0.177 | −1.968 | 0.362 |
| FPG 100-125 | Insulin-30 < 57.5 | 26 | 0.479 | 0.600 | −1.312 | 2.269 |
| FPG 100-125 | Insulin-30 > 57.5 | 26 | −3.748 | 0.000 | −5.691 | −1.805 |
| *High CHO/high GI diet* | | | | | | |
| FPG < 100 | Insulin-30 < 57.5 | 26 | 1.800 | 0.000 | 0.904 | 2.697 |
| FPG < 100 | Insulin-30 > 57.5 | 26 | 2.091 | 0.000 | 0.978 | 3.203 |
| FPG 100-125 | Insulin-30 < 57.5 | 26 | 6.190 | 0.002 | 2.306 | 10.075 |
| FPG 100-125 | Insulin-30 > 57.5 | 26 | 5.496 | 0.000 | 2.455 | 8.538 |

*Low CHO/low GI diet*

| FPG | F-Insulin (below/above median) | Week no. | Weight | P-value | 95% CL (lower) | 95% CL (upper) |
|---|---|---|---|---|---|---|
| FPG < 100 | F-Insulin < 13 & Insulin-30 > 57.5 | 26 | −1.600 | 0.055 | −3.232 | 0.033 |
| FPG < 100 | F-Insulin > 13 & Insulin-30 < 57.5 | 26 | 1.251 | 0.403 | −1.681 | 4.184 |
| FPG < 100 | F-Insulin < 13 & Insulin-30 < 57.5 | 26 | 0.910 | 0.064 | −0.052 | 1.873 |
| FPG < 100 | F-Insulin > 13 & Insulin-30 > 57.5 | 26 | 0.602 | 0.479 | −1.067 | 2.272 |
| FPG 100-125 | F-Insulin < 13 & Insulin-30 > 57.5 | 26 | −8.555 | 0.000 | −11.697 | −5.413 |
| FPG 100-125 | F-Insulin > 13 & Insulin-30 < 57.5 | 26 | 2.262 | 0.129 | −0.655 | 5.179 |
| FPG 100-125 | F-Insulin < 13 & Insulin-30 < 57.5 | 26 | −0.197 | 0.865 | −2.471 | 2.077 |
| FPG 100-125 | F-Insulin > 13 & Insulin-30 > 57.5 | 26 | −0.899 | 0.482 | −3.402 | 1.604 |

*High CHO/high GI diet*

| FPG | F-Insulin (bolow/above median) | Week no. | Weight | P-value | 95% CL (lower) | 95% CL (upper) |
|---|---|---|---|---|---|---|
| FPG < 100 | F-Insulin < 13 & Insulin-30 > 57.5 | 26 | 1.789 | 0.020 | 0.286 | 3.292 |
| FPG < 100 | F-Insulin > 13 & Insulin-30 < 57.5 | 26 | 2.118 | 0.113 | −0.505 | 4.741 |
| FPG < 100 | F-Insulin < 13 & Insulin-30 < 57.5 | 26 | 1.778 | 0.000 | 0.803 | 2.753 |
| FPG < 100 | F-Insulin > 13 & Insulin-30 > 57.5 | 26 | 2.773 | 0.002 | 1.051 | 4.495 |
| FPG 100-125 | F-Insulin < 13 & Insulin-30 > 57.5 | 26 | 5.058 | 0.009 | 1.256 | 8.860 |
| FPG 100-125 | F-Insulin > 13 & Insulin-30 < 57.5 | 26 | 7.095 | 0.012 | 1.590 | 12.600 |
| FPG 100-125 | F-Insulin < 13 & Insulin-30 < 57.5 | 26 | 5.596 | 0.051 | −0.023 | 11.215 |
| FPG 100-125 | F-Insulin > 13 & Insulin-30 > 57.5 | 26 | 6.289 | 0.020 | 0.992 | 11.586 |

Results:

The results show that simple fasting blood glucose (f-BS) is better than insulin measured in response to an insulin-30 OGTT to characterize individuals as insulin resistant/sensitive and more importantly to predict the weight loss success of pre-diabetic subjects following a low GI/low GL diet or a high GI/high GL diet.

Example 3. Low GI/Low GL Diet and High GI/High GL Diet, More Patients

This analysis was performed on the Diogenes database as in Example 1.

Analysis Based on FPG

Subjects were classified as high FPG/low FPG (same as high/low FPG) before they started the low calorie diet (LCD). Weight loss during the 8-week low calorie diet was lower among prediabetics compared to non-diabetic obese subjects [−0.76 (−1.20; −0.31) kg; P=0.001] and fat loss tended to be lower [−0.98 (−2.00; 0.03) P=0.058]. FIG. 8 presents absolute weight loss during the LCD-period among these two groups.

During the subsequent 6 month ad libitum diet phase the high CHO-high GI diet resulted in a greater weight regain [2.76 (0.55; 4.98) kg; (p=0.014)] among prediabetics compared to the normoglycemic subjects, whereas the weight regain was lower among prediabetics compared to normoglycemic subjects (−1.62 (−3.07; −0.18)] kg (p=0.027) when allocated to the low CHO/low GI diet. No difference in weight regain was observed among the three other diets (P≤0.63). Consequently, prediabetic subjects allocated to the high CHO-high GI diet regained 5.83 (3.34; 8.32) kg bodyweight (P<0.001) more compared to the prediabetics on the low CHO-low GI diet. The normoglycemic subjects allocated to the high CHO-high GI diet regained only 1.44 (0.48; 2.41) kg bodyweight (P=0.003) compared to the normoglycemic subjects on the low CHO-low GI diet (FIG. 10). Prediabetics on the low CHO-low GI diet compared to the high CHO-high GI diet therefore experienced a 4.39 (1.76; 7.02) lower (P=0.001) weight regain compared to normoglycemic subjects.

Prediabetic subjects (measured after LCD and before randomization) allocated to the high CHO-high GI diet regained 7.61 (3.40; 11.81) kg bodyweight (P<0.001) more compared to the prediabetics on the low CHO-low GI diet. The normoglycemic subjects allocated to the high CHO-high GI diet regained only 1.49 (0.56; 2.42) kg bodyweight (P=0.002) compared to the normoglycemic subjects on the low CHO-low GI diet (FIG. 4). Prediabetics on the low CHO-low GI diet compared to the high CHO-high GI diet therefore experienced a 6.11 (1.83; 10.40) kg lower (P=0.001) weight regain compared to normoglycemic subjects. As seen from FIG. 11, FPG measured after the LCD (before randomization) can also predict the weight loss success on high and low glycemic load diets.

Analysis Based on f-Insulin

Fasting insulin cannot by it selves identify different groups of weight loss on the high CHO/high GI diet but can on the low CHO/low GI diet. Subjects with lower compared to higher FI have a better weight maintenance (1.24 kg) while on the low CHO/low GI diet.

Analysis Based on FPG and f-Insulin

The results are shown in FIG. 12. Combining FI and FPG can identify the hyper-responsive obese with large weight loss on low CHO/low GI diets. Delta weight between the prediabetics (FPG=100-125) with low FI (<13) on a low CHO/low GI diet vs. a high CHO/high GI diet was 7.78 (4.36; 11.21) kg (P<0.001).

Example 4. High Fiber Low Calorie Diet

A total of 181 centrally obese men and women, with a mean (range) age of 42 y (20-66 y), body mass index (in kg/m (2)) of 30.2 (22.6-47.3), and waist circumference of 100 cm (80-138 cm) were randomly assigned to receive either the new Nordic diet (NND, or high fiber low calorie diet, high in fruit, vegetables, whole grains, and fish) or an average Danish diet (ADD) for 26 wk. Participants received cookbooks and all foods ad libitum and free of charge by using a shop model. The primary endpoint was the weight change analyzed by both completer and intention-to-treat analyses.

Analysis Based on FPG

Weight loss was significantly greater in subgroups with high FPG, compared with low FPG groups. In contrast to the NND diet, weight loss was higher in the subgroups with lower FPG. Overall, the NND diet resulted in greater weight loss compared to control (ADD) diets. The relative weight loss (NND vs ADD diets) was much more pronounced in subjects with elevated FPG compared to subjects with lower FPG (−6.04 kg vs −2.20 kg in the case of prediabetics vs. normoglycemic), as shown in FIG. 13.

Analysis Based on f-Insulin

The results are shown in FIG. 14. The sensitivity analysis across a range of FI cutoffs demonstrates that weight loss on the NND diet was consistently greater in subjects with lower FI levels. In contrast to the observed greater weight loss in low FI subjects consuming the NDD diet, weight loss in the group consuming the control (ADD) diet was unrelated to FI levels across a range of cutoffs. Individuals with a low FI have a greater "control-adjusted" weight loss (NND—control) compared to those with the high FI (2.15-3.99 kg dependent on the FI cut-off).

Analysis Based on FPG and f-Insulin

The results are shown in FIG. 15. The combination of FI and FPG distinguished between three groups of body weight responders: 1) Prediabetics, where low FI elicits greater weight loss compared to high FI, 2) Normoglycemics with low FI and 3) Normoglycemics with high FI. Individuals that benefit the most from changing their habitual diet to NND are Prediabetics regardless of their FI, followed by Normoglycemic individuals with lower FI. Normoglycemic individuals (FPG<100) with higher FI did not appear to benefit from the NND [0.45 kg, P=0.52]. On the contrary there was a tendency that normoglycemic individuals (FPG<90) with higher FI did better on the control (ADD) compared to the NND diet (−2.45 kg, P=0.072).

Analysis Based on 30-Minutes Insulin

When consuming NND, weight loss was greater in subjects with an Insulin-30 below the median, versus subjects with an Insulin-30 above the median. When consuming the control diet, weight loss was similar regardless of whether subjects Insulin-30 was above or below the median. Individuals with a low Insulin-30 have a larger "control-subtracted" weight loss (NND—control) than those with a high Insulin-30 (2.52 kg). Individuals that benefit the most from changing their habitual diet (ADD) into NND is therefore the once with low Insulin-30.

Example 5. High Fat or Low Fat Low Calorie Diet

This study investigated whether a hypo-energetic low-fat diet is superior to a hypo-energetic high-fat diet for the treatment of obesity.

Design: Open-label, 10-week dietary intervention comparing two hypo-energetic (600 kcal/day) diets with a fat energy percent of 20-25 or 40-45.

The subjects were obese adult subjects (n=771), from eight European centers. Body weight loss, dropout rates, proportion of subjects who lost more than 10% of initial body weight, blood lipid profile, insulin and glucose were measured.

Analysis Based of FPG

The results are shown in FIG. 16. Weight loss during a 10 week low-fat, hypocaloric diet was significantly lower in subjects with the highest FPG (FPG>120 and FPG>125) at baseline, compared to subjects with normal or impaired (100-125 mg/Dl) FPG. In contrast to the observed relationship between FPG and weight loss during the low-fat hypocaloric diet, weight loss during the high-fat diet was unaffected by FPG, and the diabetic subjects weight loss was no lower than the normalglycemic or the impaired subgroups. In the sensitivity analysis of the effect of FPG on weight loss, the groups with the lower FPG (FPG cutoffs <100, <115 and <120) consistently had better weight loss on the low-fat diet compared to the high fat diet. Conversely, the group with FPG>125 tended to have better weight loss on the high-fat diet. There is a significantly smaller weight loss on the low-fat diet than on the high-fat diet for the FPG>125 when compared to both other groups (only borderline for the FPG=100-125 group).

Analysis Based of f-Insulin

The sensitivity analysis of FI demonstrates that weight loss during a 10 week low-fat hypocaloric diet was consistently less in groups with higher FI (FI>11.4 and FI>17.6) compared to groups with lower FI. On the high-fat diet there is no significant difference between the weight losses across the FI groups.

Analysis Based on FPG and f-Insulin

The results are shown in FIG. 17. Individuals having normal to elevated FPG (<115 mg/dL, within pre-diabetic range) and low FI (<11.4 µIU/mL) experienced the greater weight loss when consuming a low fat diet compared to a high fat diet. In subjects with higher FPG (>115 mg/dL) and low FI (<11.4 µIU/mL), the most robust weight loss occurred while consuming a high fat hypocaloric diet, compared to a low fat hypocaloric diet.

REFERENCES

Ebbeling C B, Leidig M M, Feldman H A, Lovesky M M and Ludwig D S, 2007. Effects of a low-glycemic load vs low-fat diet in obese young adults: a randomized trial. JAMA 297(19):2092-102.

Foster-Powell K, Holt S H A and Brand-Miller J C, 2002. International table of glycemic index and glycemic load values: 2002. Am J Clin Nutr 76:5-56.

Example 6: Pre-Treatment Fasting Plasma Glucose Modifies Dietary Weight Loss Maintenance Success: Results from a Stratified RCT The purpose of this study was to investigate fasting plasma glucose (FPG) and fasting insulin (FI) as prognostic markers for weight loss maintenance when allocated to three different diets varying in macronutrient composition and fibre content.

Methods

A total of 125 participants in the MUFOBES study fulfilled the inclusion criteria and qualified for the 26-week weight loss maintenance period as they lost ≥8% of their initial body weight during the initial 8-week low-calorie diet. In this parallel-group block (gender and initial BMI) randomized trial participants were assigned to one of three ad libitum diets: 1) The new Healthy Eating Pyramid being moderate in fat (35-45 E %), high in mono-unsaturated fatty acids (>20 E %), high in fiber (>30 g/10 MJ), and high in energy density [MUFA; n=52], 2) the official Nordic Dietary Guidelines (similar to the USDA Food Pyramid) being low in fat (20-30 E %), high in fiber (>30 g/10 MJ), and low in energy density [NNR; n=48] or 3) the average Danish diet (similar to the Western diet) being high in saturated fatty acids (>15 E %), lower in fiber (<30 g/10 MJ), and high in energy density [ADD; n=25]. Alcohol (<5 E %) and protein (10-20 E %) were kept constant between the three diets. The study participants collected all foods free of charge from a supermarket established at the department during the 6-month dietary intervention. At each shopping session barcodes were scanned to ensure that the foods meet the prescribed macronutrient composition.

Weight, height, age and gender were registered prior to the low calorie diet (LCD). Weight was furthermore registered at the end of the LCD-period (to calculate weight loss during the LCD) and monthly during the 6 month dietary weight maintenance period. Blood samples were drawn after an overnight fast immediately prior to the 6 month dietary weight maintenance period and samples were stored and analyzed for fasting glucose and fasting insulin as previously reported (6). More information about the study can be found elsewhere (6).

Participants were stratified into glycemic categories by pre-treatment FPG (<90 mg/dL and 90-105 mg/dL) after having lost >8% of bodyweight during an 8 weeks LCD-period (no subjects had FPG>105 mg/dL [FPG>5.8 mmol/L]). Insulinemic categories was based on the median fasting insulin value (FI≤50 pmol/L; FI>50 pmol/L) among participants with high FPG (90-105 mg/dL). No glucose and insulin measures exist prior to the 8 week weight loss period as was used in a prior study (8); hence, the FPG cut-off was lowered from 100 mg/dL inspired by the American Diabetes Association (7) to 90 mg/dL in the present study.

Baseline characteristics were summarized as mean±standard deviation (SD), median (interquartile range [IQR]), or as proportions. Differences in baseline characteristics between glycaemic groups were assessed using two-sample t-tests (variables possibly transformed before analysis) or Pearson's chi-squared tests. Pearson correlations were carried out between 6 month weight change and FPG as well as FI at each of the three diets. Differences in weight change between glycaemic and insulinemic groups (and the combination of the two) were analysed by means of linear mixed models using completers. The linear mixed models comprised fixed effects including age, gender, baseline BMI, and LCD weight loss, as well as random effects for subjects. Results are shown as mean weight change with 95% confidence interval (CI). Differences in weight change between diets were compared within and between each blood marker group through pairwise comparisons using post hoc t-tests. The level of significance was set at P<0.05 and statistical analyses were conducted using STATA/SE 14.1 (Houston, USA).

Results

The 104 completers [(MUFA, n=38) (NNR, n=42), (ADD, n=24)] were 28.2±4.7 years old, had a median (IQR) baseline BMI of 31 (29.3; 33.0), consisted of 45% men, and lost a median (IQR) of 12.3 (9.7; 15.2) kg during the LCD period. Participants categorized as having high FPG (n=38) lost 2.0 kg (95% CI 0.5; 3.5, P=0.011) more on the LCD compared to the participants categorized as having low FPG (n=66). Proportionally more males compared to females was categorized as having high FPG (57% vs. 19%, P<0.001) whereas no age (P=0.10) or BMI (P=0.52) difference was observed between glycemic groups. The actual dietary composition was within the prescribed ranges and is reported elsewhere (6).

The correlation between baseline FPG and weight change after 6 month was r=−0.02 (P=0.90) on MUFA, r=−0.27 (P=0.088) on NNR, and r=0.41 (P=0.046) on ADD. The correlation between baseline FI and weight change after 6 month was r=−0.06 (P=0.72) on MUFA, r=0.06 (P=0.71) on NNR, and r=0.25 (P=0.25) on ADD.

Participants with low FPG and randomised to MUFA, NNR and ADD regained 2.26 kg (0.92; 3.59, P=0.001), 2.54 kg (1.50; 3.59, P<0.001) and 2.09 kg (0.50; 3.69, P=0.010)

after 26 weeks, respectively, with no differences between the three diets (all P≥0.64) (FIG. 18). Participants with high FPG and randomised to MUFA, NNR and ADD regained 2.73 kg (1.33; 4.13, P<0.001), −0.05 kg (−1.95; 1.86, P=0.96) and 4.16 kg (2.27; 6.06, P<0.001) after 26 weeks, respectively, resulting in lower weight regain on NNR compared to ADD [−4.21 kg (−6.83; −1.59), P=0.002] and MUFA [−2.77 kg (−5.12; −0.43), P=0.020] (no difference between MUFA and ADD; P=0.23) (FIG. 18). Consequently, participants with high compared to low FPG regained more on ADD compared to NNR [4.66 kg (1.43; 7.88), P=0.005] and MUFA compared to NNR [3.06 kg (0.18; 5.94), P=0.037] (no difference between MUFA and ADD; P=0.31) (FIG. 18).

Participants with low FI and randomised to MUFA, NNR and ADD regained 2.46 kg (1.30; 3.61, P<0.001), 2.07 kg (1.02; 3.12, P<0.001) and 2.35 kg (0.86; 3.83, P=0.002) after 26 weeks, respectively, with no differences between the three diets (all P≥0.63) (FIG. 19). Participants with high FI and randomised to MUFA, NNR and ADD regained 2.52 kg (0.57; 4.46, P=0.011), 1.49 kg (−0.42; 3.40, P=0.13) and 4.19 kg (0.86; 3.83, P=0.002) after 26 weeks, respectively, with no differences between the three diets (all P≥0.061) (FIG. 19). Consequently, no differences in responsiveness to the diets were found between individuals with low and high FI (all P≥0.16) (FIG. 19).

Participants with high FPG and high FI regained 6.95 kg (2.92; 10.98, P=0.001) less on the NNR than the ADD, whereas no difference was observed for the other three phenotypes (P≥0.15) (FIG. 20).

Discussion

We confirmed FPG—with and without the presence of FI—to be an important biomarker that is associated with dietary weight loss maintenance success on ad libitum diets varying in macronutrient and fiber composition. Again we show that overweight and obese participants with slightly elevated fasting blood glucose are extremely susceptible to weight regain on a western diet, but can, on the other hand refrain from weight regain on a diet lower in fat, added sugar, and energy density as well as higher in fiber even without prescribing calorie restriction per se.

We have previously reported no overall difference in weight maintenance between the three diets with a weight regain in MUFA, NNR and ADD of 2.5, 2.2, and 3.8 kg (P for difference between groups 0.31) (6). However, we now report that this insignificant overall 1.6 kg difference between NNR and ADD was due to a more than four kg difference in participants with high FPG and absolutely no difference among participants with low FPG. Further stratifying on FI revealed that the difference between these two diets was driven by an almost 7 kg difference among participants with high FPG and high FI. Recently, the New Nordic Diet, closely resembling the NNR diet of the present study, was also found to be superior among subjects with higher FPG when compared to the ADD (8). Contrary to the present study the subjects with high FPG and either low or high FI, was found to benefit equally (≈6 kg) of the New Nordic Diet compared to the ADD. Possible explanations that make the direct comparison between the two studies somewhat difficult and possibly could explain the slight deviations between the results could, besides the low numbers in each group when stratified on both FPG and FI, be the lower age, larger proportion of males, and the presence of a LCD-period in the MUFOBES study that could affect the actual level and the cut-offs for the two biomarkers, FPG and FI. Finally, according to our recently published study (8) the moderate fat diet high in fiber (MUFA) is likely to be superior among participants with FPG>115 mg/dL. However, no subjects in the current analysis had FPG>105 mg/dL and this MUFA diet warrant further investigation among participants with higher FPG.

In conclusion, slightly elevated pre-treatment FPG predicts success in dietary weight loss maintenance among overweight patients on ad libitum diets differing in fat, carbohydrate, energy density, added sugar and fibre. This easily accessible biomarker could potentially help stratifying patients in personalize dietary guidance for overweight and obesity in order to magnify weight loss and optimize weight maintenance.

REFERENCES

1. Cornier M, Donahoo W T, Pereira R, Gurevich I, Westergren R, Enerback S, et al. Insulin sensitivity determines the effectiveness of dietary macronutrient composition on weight loss in obese women. Obes Res. 2005; 13(4):703-9.
2. McClain A D, tten J J, Hekler E B, Gardner C D. Adherence to a low-fat vs. low-carbohydrate diet differs by insulin resistance status. Diabetes, Obesity and Metabolism. 2013; 15(1):87-90.
3. Gardner C D, Offringa L C, Hartle J C, Kapphahn K, Cherin R. Weight loss on low-fat vs. low-carbohydrate diets by insulin resistance status among overweight adults and adults with obesity: A randomized pilot trial. Obesity. 2016; 24(1):79-86.
4. Pittas A G, Das S K, Hajduk C L, Golden J, Saltzman E, Stark P C, et al. A low-glycemic load diet facilitates greater weight loss in overweight adults with high insulin secretion but not in overweight adults with low insulin secretion in the CALERIE Trial. Diabetes Care. 2005 December; 28(12):2939-41.
5. Ebbeling C B, Leidig M M, Feldman H A, Lovesky M M, Ludwig D S. Effects of a low-glycemic load vs low-fat diet in obese young adults: a randomized trial. JAMA. 2007; 297(19):2092-102.
6. Due A, Larsen T M, Mu H, Hermansen K, Stender S, Astrup A. Comparison of 3 ad libitum diets for weight-loss maintenance, risk of cardiovascular disease, and diabetes: a 6-mo randomized, controlled trial. Am J Clin Nutr. 2008 November; 88(5):1232-41.
7. American Diabetes Association. 2. Classification and Diagnosis of Diabetes. Diabetes Care. 2016 January; 39 Suppl 1:S13-22.
8. Hjorth M F, Ritz C, Blaak E E, Saris W H M, Langin D, Poulsen S K, Larsen T M, Sørensen T I A, Zohar Y, Astrup A (2017) Pre-treatment fasting plasma glucose and insulin modify dietary weight loss success: results from three randomized clinical trials. *Am. J. Clin. Nutr.* (Accepted).

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

The invention claimed is:

1. A method of inducing weight loss in a subject in need thereof, the method comprising administering a diet to said subject which is selected based on the fasting plasma glucose (FPG) and optionally the fasting insulin (f-insulin) of said subject, wherein
   (a) the subject has high or very high FPG and the diet is an ad libitum diet with low GI and low GL, and said diet is characterized by
      (i) a carbohydrate content between 30% and 50% of the daily energy;
      (ii) a GI between 20 and 58 units, and
      (iii) a GL between 10 and 110 grams/day;
   (b) the subject has normal FPG and the diet is an ad libitum diet with high GI and high GL, and said diet is characterized by
      (i) a carbohydrate content between 50% and 55% of the daily energy,
      (ii) a GI between 60 and 64 units, and
      (iii) GL between 135 and 140 grams/day;
   (c) the subject has normal or high FPG and the diet is a low fat diet, and said diet is characterized by a fat content between 15 and 30% of the daily energy;
   (d) the subject has very high FPG and the diet is a high fat diet, and said diet is characterized by a fat content between 35 and 50% of the daily energy;
   (e) the subject has high FPG and the diet is a high fiber diet characterized by a fiber intake higher than 20 to 45 g/10 MJ and an energy density below 115 kcal/100 g;
   (f) the subject has very high FPG and low f-insulin and the diet is a high fiber diet characterized by a fiber intake higher than 20 to 45 g/10 MJ and an energy density below 115 kcal/100 g; or
   (g) the subject has normal FPG and low f-insulin and the diet is a high fiber diet characterized by a fiber intake higher than 20 to 45 g/10 MJ and an energy density below 115 kcal/100 g;
   thereby inducing weight loss in said subject.

2. The method of claim 1, wherein the subject has high or very high FPG and the diet is the ad libitum diet with low GI/low.

3. The method of claim 1, wherein the subject has normal FPG and the diet is the ad libitum diet with high GI/high.

4. The method of claim 1, wherein the subject has normal or high FPG and the diet is the low fat diet.

5. The method of claim 1, wherein the subject has very high FPG and the diet is the high fat diet.

6. The method of claim 1, wherein the subject has high FPG and the diet is the high fiber diet.

7. The method of claim 1, wherein the weight loss is at least in part a loss of fat mass.

8. The method of claim 2, wherein the low GL/low GI diet is characterized by:
   carbohydrate content between 40% and 45% of the daily energy;
   GI between 54 and 58 units, and
   GL between 100 and 110 grams/day.

9. The method of claim 3, wherein the high GL/high GI diet is characterized by:
   carbohydrate content between 50% and 55% of the daily energy,
   GI between 60 and 64 units, and
   GL between 135 and 140 grams/day.

10. The method of claim 4, wherein the low fat diet is limited by up to 600 kcal/day.

11. The method of claim 10, wherein the low fat diet is characterized by a fat content between 20 and 25% of the daily energy.

12. The method of claim 5, wherein the high fat diet is limited by up to 600 kcal/day.

13. The method of claim 12, wherein the high fat diet characterized by a fat content between 40 and 45% of the daily energy.

14. The method of claim 6, wherein the high fiber diet is an ad libitum diet and is characterized by:
   a fiber intake higher than 25 to 45 g/10 MJ.

15. The method of claim 1, wherein:
   the normal FPG is an FPG below 100 mg/dl,
   the high FPG is an FPG between 100 and 125 mg/dl, and
   the very high FPG is an FPG higher than 125 mg/dl.

16. The method of claim 1, wherein the subject having high or very high FPG is affected by prediabetes or type 2 diabetes.

17. The method of claim 1, wherein the subject having high or very high FPG is affected by inherited, acquired or iatrogenic insulin resistance.

18. The method of claim 1, further comprising administering to the subject having high or very high FPG a therapeutic agent that stimulates insulin secretion and/or a therapeutic agent that reduces insulin resistance so that the weight loss success or weight maintenance success of the diet is increased.

19. The method of claim 1, wherein the low f-insulin is an f-insulin value lower than 13 μIU/ml.

20. The method of claim 1, wherein weight loss is primarily fat loss.

21. The method of claim 1, wherein the subject is obese or overweight.

* * * * *